(12) United States Patent
Pitson et al.

(10) Patent No.: US 6,730,480 B1
(45) Date of Patent: May 4, 2004

(54) SPHINGOSINE KINASE ENZYME

(75) Inventors: Stuart Maxwell Pitson, South Australia (AU); Brian Wolff Wattenberg, South Australia (AU); Pu Xia, South Australia (AU); Richard James D'Andrea, South Australia (AU); Jennifer Ruth Gamble, South Australia (AU); Matthew Alexander Vadas, South Australia (AU)

(73) Assignee: Johnson & Johnson Pharmaceutical Research and Development LLC, Raritan, NJ (US)

( * ) Notice: Subject to any disclaimer, the term of this patent is extended or adjusted under 35 U.S.C. 154(b) by 0 days.

(21) Appl. No.: 09/959,897
(22) PCT Filed: May 12, 2000
(86) PCT No.: PCT/AU00/00457
§ 371 (c)(1),
(2), (4) Date: Jan. 24, 2002
(87) PCT Pub. No.: WO00/70028
PCT Pub. Date: Nov. 23, 2000

(30) Foreign Application Priority Data

May 13, 1999 (AU) ............................................ PQ 0339
Jul. 8, 1999 (AU) ............................................ PQ 1504

(51) Int. Cl.$^7$ .......................... C12Q 1/68; C12N 15/00; C12N 1/20; C12N 9/12; C07H 21/04
(52) U.S. Cl. ..................... 435/6; 435/320.1; 435/325; 435/252.3; 435/194; 435/15; 536/23.2
(58) Field of Search .......................... 435/194, 15, 6, 435/252.3, 325, 320.1; 536/23.2

(56) References Cited

FOREIGN PATENT DOCUMENTS

| WO | 99/12533 | * | 3/1999 |
| WO | WO 99/61581 A2 | | 12/1999 |
| WO | WO 00/05365 A1 | | 2/2000 |
| WO | WO 00/52173 A2 | | 9/2000 |
| WO | WO 00/55332 A2 | | 9/2000 |

OTHER PUBLICATIONS

Geneseq Database, Accession No. AAV84490, Mar. 1999.*
SPTREMBL Database, accession No. 088886, 11/98, cited as Kohama et al. J.B.C., 273, 23722–23728, 1998 in the IDS.*
Kohama et al. "Molecular Cloning and Functional Characterization of Murine Sphingosine Kinase", The Journal of Biological Chemistry, vol. 273, No. 37 pp. 23722–23728, 1998.
Su Y et al. "Sphingosine 1–Phosphate, A Novel Signaling Molecule, Stimulates DNA Binding Activity of AP–1 in Quiescent Swiss 3T3 Fibroblasts", The Journal of Biological Chemistry, vol. 269, No. 23 pp. 16512–16517, 1994.
Kolesnick et al. "Characterization of a Ceramide Kinase Activity From Human Leukemia (HL–60) Cells", The Journal of Biological Chemistry, vol. 265, No. 31 pp. 18803–18808, 1990.
Hinkovska–Galcheva et al. "The Formation of Ceramide–1–Phosphate During Neutrophil Phagocytosis and its Role in Liposome Fusion", The Journal of Biological Chemistry, vol. 273, No. 50 pp. 33203–33209, 1998.
Nava et al., "Functional Characterization of Humn Sphingosine Kinase–1" FEBS LETTERS, vol. 473, No. 1, May 4, 2000, pp. 81–84.

* cited by examiner

Primary Examiner—M. Monshipouri
(74) Attorney, Agent, or Firm—Browdy and Neimark, P.L.L.C.

(57) ABSTRACT

The present invention relates generally to novel protein molecules and to derivatives, analogues, chemical equivalents and mimetics thereof capable of modulating cellular activity and, in particular, modulating cellular activity via the modulation of signal transduction. More particularly, the present invention relates to human sphingosine kinase and to derivatives, analogues, chemical equivalents and mimetics thereof. The present invention also contemplates genetic sequences encoding said protein molecules and derivatives, analogues, chemical equivalents and mimetics thereof. The molecules of the present invention are useful in a range of therapeutic, prophylactic and diagnostic application.

9 Claims, 24 Drawing Sheets

```
                                                                    19
  1           gagccgcgggtcgaggtt ATGGATCCAGGCGGGCCCCGGGGCGTGCTGCCGCGGCCCTGCCGTGTGCTGGTG    75
              M D P A G G P R G V L P R P C R V L V 20   L L N P R G G K G K A L Q L F R S H V Q P L L A E              44
  1   CTGCTGAACCCGCGCGGCGGCAAGGGCAAGGCCCTGCAGCTCTTCCGAGTCACGTGCAGCCCCCTTTTGGCTGAG          150

45   A E I S F T L M L T E R R N H A R E L V R S E E L              69
151   GCTGAAATCTCCTTCACGCTGATGCTCACTGAGCGGCGGAACCACGCGCGGGAGCTGGTGCGGTCGGAGGAGCTG          225

70   G R W D A L V V M S G D G L M H E V V N G L M E R              94
226   GGCCGCTGGGACGCTCTGGTGGTCATGTCTGGAGACGGGCTGATGCACGAGGTGGTGAACGGGCTCATGGAGCGG          300

95   P D W E T A I Q K P L C S L P A G S G N A L A A S             119
301   CCTGACTGGGAGACCGCCATCCAGAAGCCCCTGTGTAGCCTCCCAGCAGGTTCTGGCAACGCGCTGGCAGCTTCC          375

120   L N H Y A G Y E Q V T N E D L L T N C T L L L C R             144
376   TTGAACCATTATGCTGGCTATGAGCAGGTCACCAATGAAGACCTCCTGACCAACTGCACGCTATTGCTGTGCCGC          450

145   R L L S P M N L L S L H T A S G L R L F S V L S L             169
451   CGGCTGCTGTCACCCATGAACCTGCTGTCTCTGCACACGGCTTCGGGGCTTCGTCTCTTCTCTGTCTTCAGCCTG          525

170   A W G F I A D V D L E S E K Y R R L G E M R F T L             194
526   GCCTGGGGCTTCATTGCTGATGTGGACCTAGAGAGTGAGAAGTATCGGCGTCTGGGGGAGATGCGCTTCACTCTG          600
```

Figure 7A-1

```
195  G  T  F  L  R  L  A  A  L  R  T  Y  R  G  R  L  A  Y  L  P  V  G  R  V  G    219
601  GGCACTTTCCTGCGTCTGGCAGCCTTGCGCACTTACCGGGCCGACTGGCTTACCTCCCTGTAGGAAGAGTGGGT    675

220  S  K  T  P  A  S  P  V  V  Q  Q  G  P  V  D  A  H  L  V  P  L  E  E  P      244
676  TCCAAGACACCTGCCTCCCCCGTTGTGCCAGCAGGGCCCGTAGATGCACACCTTGTGCCACTGGAGGAGCCA      750

245  V  P  S  H  W  T  V  V  P  D  E  D  F  V  L  V  L  A  L  L  H  S  H  L  G    269
751  GTGCCCTCTCACTGGACAGTGGTGCCCGACGAGGACTTTGTGCTAGTCCTGGCACTGCTGCACTCGGGC         825

270  S  E  M  F  A  A  P  M  G  R  C  A  A  G  V  M  H  L  F  Y  V  R  A  G  V    294
826  AGTGAGATGTTTGCTGCACCCATGGGCCGCTGTGCAGCTGGCGTCATGCATCTGTTCTACGTGCGGGCGGAGTG   900

295  S  R  A  M  L  L  R  L  F  L  A  M  E  K  G  R  H  M  E  Y  E  C  P  Y  L    319
901  TCTCGTGCCATGCTGCTGCGCCTCTTCCTGGCCATGGAGAAGGGCAGGCATATGGAGTATGAATGCCCCTACTTG  975

320  V  Y  P  V  V  A  F  R  L  E  P  K  D  G  K  G  M  F  A  V  D  G  E  L       344
976  GTATATGTGCCCGTGGTCGCCTTTCGCCTTGGAGCCCAAGGATGGGAAAGGTATGTTTGCAGTGGATGGGAATTG  1050

345  M  V  S  E  A  V  Q  G  Q  V  H  P  N  Y  F  W  M  V  S  G  C  V  E  P  P    369
1051 ATGGTTAGCGAGGCCGTGCAGGGCCAGGTGCACCCAAACTACTTCTGGATGGTCAGCGGTTGCGTGGAGCCCCCG  1125

370  P  S  W  K  P  Q  Q  M  P  P  P  E  E  P  L  *                              384
1126 CCCAGCTGGAAGCCCCAGCAGATGCCACCGCCAGAAGAGCCCTTAtga                             1173
```

Figure 7A-2

```
195  G  T  F  L  R  L  A  A  A  L  R  T  Y  R  G  R  L  A  Y  L  P  V  G  R  V  G        219
601  GGCACTTTCCTGCGTCTGGCAGCCTTGCGCACTTACCGGCGGCCGACTTGGCTTACCTCCCTGTAGGAAGAGTGGGT        675

220  S  K  T  P  A  S  P  V  V  Q  Q  G  P  V  D  A  H  L  V  P  L  E  E  P              244
676  TCCAAGACACCTGCCTCCCCCGTGTGGTCCAGCAGGGCCCGGTAGATGCACACCTTGTGCCACTTGAGGAGCCA           750

245  V  P  S  H  W  T  V  V  P  D  E  D  F  V  L  V  L  A  L  L  H  S  H  L  G           269
751  GTGCCCTCTCACTGGACAGTGGTGCCCGACGAGGACTTTGTGCTAGTCCTGGCACTGCTGCACTCGCACCTGGGC        825

270  S  E  M  F  A  A  P  .  M  G  R  C  A  A  G  V  M  H  L  F  Y  V  R  A  G  V        294
826  AGTGAGATGTTTGCTGCACCCATGGGCCGCTGTGCAGCTGGCGTCATGCATCTGTTCTACGTGCGGGCGGAGTG        900

295  S  R  A  M  L  L  R  L  F  L  A  M  E  K  G  R  H  M  E  Y  E  C  P  Y  L           319
901  TCTCGTGCCATGCTGCTGCGCCTCTTCCTGGCCATGGAGAAGGGCAGGCATATGGAGTATGAATGCCCCTACTTG        975

320  V  Y  V  P  V  V  A  F  R  L  E  P  K  D  G  K  G  M  F  A  V  D  G  E  L           344
976  GTATATGTGCCCGTGGTCGCCTTCCGCTTGGAGCCCAAGGATGGGAAAGGTATGTTTGCAGTGGATGGGGAATTG        1050

345  M  V  S  E  A  V  Q  G  Q  V  H  P  N  Y  F  W  M  V  S  G  C  V  E  P  P           369
1051 ATGGTTAGCGAGGCCGTGCAGGGCCAGGTGCACCCAAACTACTTCTGGATGGTCAGCGGTTGCGTGGAGCCCCCG        1125

370  P  S  W  K  P  Q  Q  M  P  P  P  E  E  P  L  •                                       384
1126 CCCAGCTGGAAGCCCCAGCAGATGCCACCGCCAGAAGAGCCCTTAtga                                     1173
```

Figure 7a(ii)

```
hSK         1                                      .......MDPAGGPRGVLRPCRVLLLNPRGGKGKALQLFRSHVQPLAEAEIS
mSK1a       1                                      .......MEPECPRGLLRPCRVLLLNPQGGKGKALQLFQSRVQPFEEAEIT
mSK1b       1                                MWCCVL.FVVECPRGLLRPCRVLLLNPQGGKGKALQLFQSRVQPFEEAEIT
Yeast LCB4  206  NISSGTVEEILEKSYENSKRNRSILVIINPHGGKGTAKNLFLTKARPILVESGCK
Yeast LCB5  252  DL.....VEEILKRSYKNTRRNKSIFVIINPFGGKGKAKKLFMTKAKPLLASRCS
S. pombe    90   .......FCEYLLDVAYKGIKRSRRFIVFINPHGGKGKAKHIWESEAEPVFSSAHSI
C. elegans  63   ENEQLTSVILSRKPPPQEQCRGNLLVFINPNSGTGKSLETFANTVGKLDKSLIR
Consensus         .......................R...**V..*NP.GGKGKA..*F.*...P.L..* hSK         112  SGNALAASLNHYAGYEQVTNEDLLTNCTLLCRR....LLSPMNLLSLHTASGLRL
mSK1a       111  SGNALAASVNHYAGYEQVTNEDLLINCTLLCRR....RLSPMNLLSLHTASGLRL
mSK1b       118  SGNALAASVNHYAGYEQVTNEDLLINCTLLCRR....RLSPMNLLSLHTASGLRL
Yeast LCB4  325  SGNAMSIS................CHWTNNPSYAALCLVKSIETRIDLWCCSQPSYMNEWPR
Yeast LCB5  368  SGNAMSVS................CHWTNNPSYSTLCLIKSIETRIDLWCCSQPSYAREHPK
S. pombe    203  SGNAFSYN......ATGQLKPALTALEILKGRPTSFDLWTFEQ...KGKKA
C. elegans  184  SGNGLLCSV.LSKYGTKMNEKSVMERALEIATSPTAKAESVALYSVKTDNQ.SY
Consensus         SGNA*...S.......................*L.*...........M......
```

Figure 9A

```
hSK          1   .......MDPAGGPRGVLPRPCRVLVLLNPRGGKGKALQLFRSHVQPLLAEAEIS
mSK1a        1   .......MEPECPRGLLPRPCRVLVLLNPQGGKGKALQLFQSRVQPFLEEAEIT
mSK1b        1   MWWCCVL.FVVECPRGLLPRPCRVLVLLNPQGGKGKALQLFQSRVQPFLEEAEIT
Yeast LCB4 206   NISSGTVEEILEKSYENSKRNRSILVIINPHGGKGTAKNLFLTKARPILVESGCK
Yeast LCB5 252   DL.....VEEILKRSYKNTRRNKSIFVIINPFGGKGKAKKLEMTKAKPLLASRCS
S. pombe    90   .......FCEYLLDVAYKGIKRSRRFIVFINPHGGKGKAKHIWESEAEPVFSSAHSI
C. elegans  63   ENEQLTSVILSRKPPPQEQCRGNLLVFINPNSGTKSLETEANTVGKEDKSLIR
Consensus        *........*......R....**V.*NP.GGKGKA..*F.*...P.L..* hSK        112   SGNALAASLNHYAGYEQVTNEDLLTNCTLLLCRR....LLSPMNLLSLHTASGLRL
mSK1a      111   SGNALAASVNHYAGYEQVTNEDLLINCTLLLCRR....RLSPMNLLSLHTASGLRL
mSK1b      118   SGNALAASVNHYAGYEQVTNEDLLINCTLLLCRR....RLSPMNLLSLHTASGLRL
Yeast LCB4 325   SGNAMSIS..........CHWTNNPSYAALCLVKSIETRIDLMCCSQPSYMNEWPR
Yeast LCB5 368   SGNAMSVS..........CHWTNNPSYSTLCLIKSIETRIDLMCCSQPSYAREHPK
S. pombe   203   SGNAFSYN..........ATGQLKPALTALEILKGRPTSFDLMTFEQ....KGKKA
C. elegans 184   SGNGLLCSV..LSKYGTKMNEKSVMERALEIATSPTAKAESVALYSVKTDNQ.SY
Consensus        SGNA*..S...................*L.*........M..........
```

Figure 9(i)

```
hSK         211  .......AYLP.................                                                    VGRVGSKTPASPVVQQGPVD
mSK1a       210  .......AYLP.................                                                    VGTVASKRPAST.LVQKGPVD
mSK1b       217  .......AYLP.................                                                    VGTVASKRPAST.LVQKGPVD
Yeast LCB4  435  ENKDKNKGCLTFEP..NPSPNSSPDLLSKNNINNSTKDE..........
Yeast LCB5  478  EH..KNKGSLEFQHITMNKDNEDCDNYNYENEYETENEDEDEDADADDEDSHLIS
S. pombe    308  ........................EKSKNLAPMSESSDSDK..........
C. elegans  284  .......TYRPYKPKGFHPSSNVFSVYEKTTQQRIDDSKVKTNGSVSDSEEETME
Consensus        .      *                                                                        * hSK         282  AGVMHLFYV..RAGVSRAMLLRLFLAMEKGRHMEYECPYLVYVPVVAFRLEPKDG
mSK1a       280  AGVMHLFYV..RAGVSRAALLRLFLAMQKGKHMELDCPYLVHPVVAFRLEPRSQ
mSK1b       287  AGVMHLFYV..RAGVSRAALLRLFLAMQKGKHMELDCPYLVHPVVAFRLEPRSQ
Yeast LCB4  532  DGTIDLVITDARIPVTR..MTPILLSLDKGSH..VLEPEVIHSKILAYKIIPKVE
Yeast LCB5  586  DGTMDMVITDARTSLTR..MAPILLGLDKGSH..VLQPEVLHSKILAYKIIPKLG
S. pombe    367  DGLIDVVIVYSKQFRKS..LLSMFTQLDNGGF..YYSKHLNYYKVRSFRFTPVNT
C. elegans  388  DNRIHLSYILWKDIGTRVNIAKYLLAIEHETHLDL..BFVKHVEVSSMKLEVISE
Consensus        .G.*  ..          *R.*   *.*.L*..*...G.H......P.*....*......P....
```

Figure 9(ii)

```
FTLMLTERRNHARE.LVRSEELGRWDALVVMSGDGLMHEVVNGLMERPDWETAI.QKPLCSLPAG
FKLILTERKNHARE.LVCAEELGHWDALAVMSGDGLMHEVVNGLMERPDWETAI.QKPLCSLPGG
FKLILTERKNHARE.LVCAEELGHWDALAVMSGDGLMHEVVNGLMERPDWETAI.QKPLCSLPGG
IEIAYTKYARHAID.IAKDLDISKYDTIACASGDGIPYEVINGLYRRPDRVDAFNKLAVTQLPCG
IEVVYTKYPGHAIE.IAREMDIDKYDTIACASGDGIPHEVINGLYQRPDHVKAFNNIAITEIPCG
CEVVLTRRKDHAKS.IAKNLDVGSYDGILSVGGDGLFHEVINGLGERDDYLEAF.KLPVCMIPGG
YEVVVTGPNHARNVLMTKADLGKFNGVLILSGDGLVFEALNGILCREDAFRIFPTLPIGIVPSG
..*...T....HA.*.......*..*.......*D.*....SGDG*...EV*NGL..R.D...A......*.P.G

............
                                                        ............
                                                        ............
                                                        ............
                                                        ............
                                                        ............
                                                        ............

FSVLSLAWGFIADVDLESEKYRR.LGEMRFTLGTFLRLAALRTYRGRL............
YSVLSLSWGFVADVDLESEKYRR.LGEIRFTVGTFFFRLASLRIYQGQL............
YSVLSLSWGFVADVDLESEKYRR.LGEIRFTVGTFFFRLASLRIYQGQL............
LSFLSQTYGVIAESDINTE.FIRWMGPVRFNLGVAFNIIQGKKYPCEVFVKYAAKSKKELKVHFL
LSFLSQTYGLIAETDINTE.FIRWMGPARFELGVAFNIIQKKKYPCEIYVKYAAKSKNELKNHYL
YSFLTANYGIIADCDIGTE.NWRFMGENRAYLGFFLRLFQKPDWKCSIEMDVVSSDRTEIKHMY.
ASFLSIGWGLMADIDIDSEKWRKSLGHHRFTVMGFIRSCNLRSYKGRL............
.S.LS.**G..*A*.D***.E.*.R..*G...RF..*G......Y...........*
```

Figure 9(iii)

```
AHLVPLEEPVPSHW.........TVVPD.................EDFVLVLALLHSHLGSEMFAAPMGRCA
THLVPLEEPVPSHW.........TVVPE.................QDFVLVLLLHTHLSSELFAAPMGRCE
THLVPLEEPVPSHW.........TVVPE.................QDFVLVLVLLHTHLSSELFAAPMGRCE
....LSPNFLNEDNFKLKYPMTEPVPRDWEKMDSELTDNLTIFYTGKMPYIAKDTKFFPAALPA
RDLADSSADQIKEEDFKIKYPLDEGIPSDWERLDPNISNNLGIFYTGKMPYVAADTKFFPAALPS
....................TVSTSPESHLLTFEI.NDLSIFCAGLLPYIAPDAKMFPAASND
TKFQNWTLPDSDETLAVGSSDLEETVVIE.......DNFVNIYAVTLSHIAADGPFAPSAKLE
                                                *****   ..P..
                                                                    identity KG..MFEAVDGELMVSEAVQGQVHPNYFW.MVSGCVEPPPSWKPQQMPPPPEEPL              81%
RG...VFSVDGELMVCEAVQGQVHPNYLW.MVCGSRDAPSGRDSRRGPPPEEP.               80%
RG...VFSVDGELMVCEAVQGQVHPNYLW.MVCGSRDAPSGRDSRRGPPPEEP.               28%
SG...LFSVDGEKFPLEPLQVEIMPMLCKTLLRNGRYIDTEFESM........                30%
NG...LFSVDGEKFPLEPLQVEIMPRLCKTLLRNGRYVDTDFDSM........                30%
GKRHYFALDGESYPLEPFECRVAPKLGTTLSPVAGFQLLDI............                30%
GS..HVVLDGEVDTKTIEVASTKNHIS.VFSSTA...................
.*...F**DGE....E***..*..P............*...
```

Figure 9(iv)

```
hSK         211  ......AYLP............................................VGRVGSKTPASPVVVQQGPVD
mSK1a       210  ......AYLP............................................VGTVASKRPAST.LVQKGPVD
mSK1b       217  ......AYLP................................................VGTVASKRPAST.LVQKGPVD
Yeast LCB4  435  ENKDKNKGCLTFEP..NPSPNSSPDLLSKNNINNSTKDE.............................
Yeast LCB5  478  EH..KNKGSLEFQHITMNKDNEDCDNYNYENEYETENEDEDEDADADDEDSHLIS
S. pombe    308  ....................EKSKNLAPMSESSDSDK.................
C. elegans  284  ........TYRPYKPKGFHPSSNVFSVYEKTTQQRIDDSKVKTNGSVSDSEEETME
Consensus            .            .                  *                  .

hSK         282  AGVMHLFYV..RAGVSRAMLLRLFLAMEKGRHMEYECPYLVVYPVVAFRLEPKDG
mSK1a       280  AGVMHLFYV..RAGVSRAALLRLFLAMQKGKHMELDCPYLVHVPVVAFRLEPRSQ
mSK1b       287  AGVMHLFYV..RAGVSRAALLRLFLAMQKGKHMELDCPYLVHVPVVAFRLEPRSQ
Yeast LCB4  532  DGTIDLVITDARIPVTR..MTPILFSLDKGSH..VLEPEVIHSKILAYKIIPKVE
Yeast LCB5  586  DGTMDMVITDARTSLTR..MAPILEGLDKGSH..VLQPEVLHSKILAYKIIPKLG
S. pombe    367  DGLIDVVIYSKQFRKS.LLSMFTQLDNGGF..YYSKHLNYYKVRSFRFTEVNT
C. elegans  388  DNRIHLSYILWKDIGTRVNIAKYLEAIEHETHLDL..EFVKHVEVSSMKLEVISE
Consensus         .G .*     .*R.*  *L .  .        . L .   G H      P       .P Figure 9B
```

```
FTLMLTERRNHARE.LVRSEELGRWDALVVMSGDGLMHEVVNGLMERPDWETAI.QKPLCSLPAG
FKLILTERKNHARE.LVCAEELGHWDALAVMSGDGLMHEVVNGLMERPDWETAI.QKPLCSLPGG
FKLILTERKNHARE.LVCAEELGHWDALAVMSGDGLMHEVVNGLMERPDWETAI.QKPLCSLPGG
IEIAYTKYARHAID.IAKDLDISKYDTIACASGDGIPYEVINGLYRRPDRVDAFNKLAVTQLPCG
IEVVYTKYPGHAIE.IAREMDIDKYDTIACASGDGIPHEVINGLYQRPDHVKAFNNIAITEIPCG
CEVVLTRRKDHAKS.IAKNLDVGSYDGILSVGGDGLFHEVINGLGERDDYLEAF.KLPVCMIPGG
YEVVVTGPNHARNVLMTKADLGKFNGVLILSGDGLVFEALNGILCREDAFRIFPTLPIGIVPSG
.***..*.*.****.*...*.*..**D..*.****.SGDG*..EV*NGL..R.D...A....*.P.G

FSVLSLAWGFIADVDLESEKYRR.LGEMRFTLGTFLRLAALRTYRGRL........
YSVLSLSWGFVADVDLESEKYRR.LGEIRFTVGTFFRLASLRIYQGQL........
YSVLSLSWGFVADVDLESEKYRR.LGEIRFTVGTFFRLASLRIYQGQL........
LSFLSQTYGVIAESDINTE.FIRWMGPVRFNLGVAFNIIQGKKYPCEVFVKYAAKSKKELKVHFL
LSFLSQTYGLIAETDINTE.FIRWMGPAREELGVAFNIIQKKKYPCEIYVKYAAKSKNELKNHYL
YSFLTANYGIIADCDIGTE.NWRFMGENRAYLGFFLRLFQKPDWKCSIEMDVVSSDRTEIKHMY.
ASFLSIGWGLMADIDIDSEKWRKSLGHHRFTVMGFIRSCNLRSYKGRL........
.S.LS.**G.*A*.D***.E.*.R.*G...RF.*G........Y....*.......

Figure 9C
```

```
AHLVPLEEPVPSHW..........TVVPD..........EDFVLVLALLHSHLGSEMFAAPMGRCA
THLVPLEEPVPSHW..........TVVPE..........QDFVLVLVLLHTHLSSELFAAPMGRCE
THLVPLEEPVPSHW..........TVVPE..........QDFVLVLVLLHTHLSSELFAAPMGRCE
......LSPNFLNEDNFKLKYPMTEPVPRDWEKMDSELTDNLTIFYTGKMPYIAKDTKFFAALPA
RDLADSSADQIKEEDFKIKYPLDEGIPSDWERLDPNISNNLGIFYTGKMPYVAADTKFFAALPS
..........................TVSTSPESHLLTFEI.NDLSIFCAGLLPYIAPDAKMFAASND
TKFQNWTLPDSDETLAVGSSDLEETVVIE..........DNFVNIYAVTLSHIAADGPFAPSAKLE
..........................*..*..........*..*....*...........P
```

```
KG..MFAVDGELMVSEAVQGQVHPNYFW.MVSGCVEPPPSWKPQQMPPPEEPL   identity
RG..VFSVDGELMVCEAVQGQVHPNYLW.MVCGSRDAPSGRDSRRGPPPEEP.   81%
RG..VFSVDGELMVCEAVQGQVHPNYLW.MVCGSRDAPSGRDSRRGPPPEEP.   80%
SG..LFSVDGEKFPLEPLQVEIMPMLCKTLLRNGRYIDTEFESM..........  28%
NG..LFSVDGEKFPLEPLQVEIMPRLCKTLLRNGRYVDTDFDSM..........  30%
GKRHYEALDGESYPLEPFECRVAPKLGTTLSPVAGFQLLDI.............  30%
GS..HVVLDGEVVDTKTIEVASTKNHIS.VFSSTA...................  30%
*...F**DGE....E***...*P.........*
```

Figure 9D

SPHINGOSINE KINASE ENZYME

REFERENCE TO RELATED APPLICATIONS

The present application is the national stage under 35 U.S.C. 371 of international application PCT/AU00/00457, filed May 12, 2000 which designated the United States, and which international application was published under PCT Article 21(2) in the English language.

FIELD OF THE INVENTION

The present invention relates generally to novel protein molecules and to derivatives, analogues, chemical equivalents and mimetics thereof capable of modulating cellular activity and, in particular, modulating cellular activity via the modulation of signal transduction. More particularly, the present invention relates to human sphingosine kinase and to derivatives, analogues, chemical equivalents and mimetics thereof. The present invention also contemplates genetic sequences encoding said protein molecules and derivatives, analogues, chemical equivalents and mimetics thereof. The molecules of the present invention are useful in a range of therapeutic, prophylactic and diagnostic applications.

BACKGROUND OF THE INVENTION

Bibliographic details of the publications referred to by author in this specification are collected alphabetically at the end of the description.

Sphingosine kinase is a key regulatory enzyme in a variety of cellular responses. Its activity can affect inflammation, apoptosis and cell proliferation, and thus it is an important target for therapeutic intervention.

Sphingosine-1-phosphate is known to be an important second messenger in signal transduction (Meyer et al., 1997). It is mitogenic in various cell types (Alessenko, 1998; Spiegel et al., 1998) and appears to trigger a diverse range of important regulatory pathways including; prevention of ceramide-induced apoptosis (Culliver et al., 1996), mobilisation of intracellular calcium by an $IP_3$-independant pathway, stimulation of DNA synthesis, activation of mitogen-activated protein (MAP) kinase pathway, activation of phospholipase D, and regulation of cell motility (for reviews see Meyer et al., 1997; Spiegel et al., 1998; Igarashi., 1997). Recent studies (Xia et al., 1998) have shown that sphingosine-1-phosphate is an obligatory signaling intermediate in the inflammation response of vascular endothelial cells to tumor necrosis factors-α(TNFα). In spite of its obvious importance, very little is known of the mechanisms that control cellular sphingosine-1-phosphate levels. It is known that sphingosine-1-phosphate levels in the cell are mediated largely by its formation from sphingosine by sphingosine kinase, and to a lesser extent by its degradation by endoplasmic reticulum-associated sphingosine-1-phosphate lyase and sphingosine-1-phosphate phosphatase (Spiegel et al., 1998). Basal levels of sphingosine-1-phosphate in the cell are generally low, but can increase rapidly and transiently when cells are exposed to mitogenic agents. This response appears correlated with an increase in sphingosine kinase activity in the cytosol and can be prevented by addition of the sphingosine kinase inhibitory molecules N,N-dimethylsphingosine and DL-threo-dihydrosphingosine. This indicates that sphingosine kinase is an important molecule responsible for regulating cellular sphingosine-1-phosphate levels. This places sphingosine kinase in a central and obligatory role in mediating the effects attributed to sphingosine-1-phosphate in the cell.

Accordingly, there is a need to identify and clone novel sphingosine kinase molecules to facilitate the progression towards the more sensitive control of intracellular signal transduction via, for example, the elucidation of the mechanism controlling the expression and enzymatic activity of sphingosine kinase thereby providing a platform for the development of interventional therapies to regulate the expression or activity of sphingosine kinase. In work leading up to the present invention the inventors have purified and cloned a novel sphingosine kinase molecule.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

One aspect of the present invention provides an isolated nucleic acid molecule or derivative or analogue thereof comprising a nucleotide sequence encoding or complementary to a sequence encoding a novel sphingosine kinase protein or a derivative or mimetic of said sphingosine kinase protein.

Another aspect of the present invention provides an isolated nucleic acid molecule or derivative or analogue thereof comprising a nucleotide sequence encoding or complementary to a sequence encoding a human sphingosine kinase protein or a derivative or mimetic of said sphingosine kinase protein.

Yet another aspect of the present invention provides a nucleic acid molecule or derivative or analogue thereof comprising a nucleotide sequence encoding, or a nucleotide sequence complementary to a nucleotide sequence encoding, an amino acid sequence substantially as set forth in SEQ ID NO:2 or a derivative or mimetic thereof or having at least about 45% or greater similarity to at least 10 contiguous amino acids in SEQ ID NO:2.

Still another aspect of the present invention contemplates a nucleic acid molecule or derivative or analogue thereof comprising a nucleotide sequence substantially as set forth in SEQ ID NO:1 or a derivative thereof or capable of hybridising to SEQ ID NO:1 under low stringency conditions.

Still yet another aspect of the present invention contemplates a nucleic acid molecule or derivative or analogue thereof comprising a nucleotide sequence substantially as set forth in SEQ ID NO:1 or a derivative thereof, or capable of hybridising to SEQ ID NO:1 under low stringency conditions and which encodes an amino acid sequence corresponding to an amino acid sequence set forth in SEQ ID NO:2 or a sequence having at least about 45% similarity to at least 10 contiguous amino acids in SEQ ID NO:2.

A further aspect of the present invention contemplates a nucleic acid molecule comprising a sequence of nucleotides substantially as set forth in SEQ ID NO:1.

Another further aspect of the present invention contemplates a genomic nucleic acid molecule or derivative or analogue thereof capable of hybridising to SEQ ID NO:1 or a derivative thereof under low stringency conditions at 42° C.

Still another further aspect of the present invention provides a cDNA sequence comprising a sequence of nucleotides as set forth in SEQ ID NO:1 or a derivative or analogue thereof including a nucleotide sequence having similarity to SEQ ID NO:1.

Yet another further aspect of the present invention provides an amino acid sequence set forth in SEQ ID NO:2 or a derivative, analogue or chemical equivalent or mimetic thereof as defined above or a derivative or mimetic having an amino acid sequence of at least about 45% similarity to at least 10 contiguous amino acids in the amino acid sequence as set forth in SEQ ID NO:2 or a derivative or mimetic thereof.

Still yet another further aspect of the present invention is directed to an isolated protein selected from the list consisting of:

(i) A novel sphingosine kinase protein or a derivative, analogue, chemical equivalent or mimetic thereof.

(iii) A protein having an amino acid sequence substantially as set forth in SEQ ID NO:2 or a derivative or mimetic thereof or a sequence having at least about 45% similarity to at least 10 contiguous amino acids in SEQ ID NO:2 or a derivative, analogue, chemical equivalent or mimetic of said protein.

(iv) A protein encoded by a nucleotide sequence substantially as set forth in SEQ ID NO:1 or a derivative or analogue thereof or a sequence encoding an amino acid sequence having at least about 45% similarity to at least 10 contiguous amino acids in SEQ ID NO:2 or a derivative, analogue, chemical equivalent or mimetic of said protein.

(v) A protein encoded by a nucleic acid molecule capable of hybridising to the nucleotide sequence as set forth in SEQ ID NO:1 or a derivative or analogue thereof under low stringency conditions and which encodes an amino acid sequence substantially as set forth in SEQ ID NO:2 or a derivative or mimetic thereof or an amino acid sequence having at least about 45% similarity to at least 10 contiguous amino acids in SEQ ID NO:2

(ii) A human sphingosine kinase protein or a derivative, analogue, chemical equivalent or mimetic thereof.

(vi) A protein as defined in paragraphs (i) or (ii) or (iii) or (iv) or (v) in a hormodimeric form.

(vii) A protein as defined in paragraphs (i) or (ii) or (iii) or (iv) or (v) in a heterodimeric form.

Another aspect of the present invention contemplates a method of modulating activity of sphingosine kinase in a mammal, said method comprising administering to said mammal a modulating effective amount of an agent for a time and under conditions sufficient to increase or decrease sphingosine kinase activity.

Still another aspect of the present invention contemplates a method of modulating cellular functional activity in a mammal said method comprising administering to said mammal an effective amount of an agent for a time and under conditions sufficient to modulate the expression of a nucleotide sequence encoding sphingosine kinase or sufficient to modulate the activity of sphingosine kinase.

Yet another aspect of the present invention contemplates a method of modulating cellular functional activity in a mammal said method comprising administering to said mammal an effective amount of sphingosine kinase or sphingosine kinase.

Still yet another aspect of the present invention relates to a method of treating a mammal said method comprising administering to said mammal an effective amount of an agent for a time and under conditions sufficient to modulate the expression of sphingosine kinase or sufficient to modulate the activity of sphingosine kinase wherein said modulation results in modulation of cellular functional activity.

A further aspect of the present invention relates to a method of treating a mammal said method comprising administering to said mammal an effective amount of sphingosine kinase or sphingosine kinase for a time and under conditions sufficient to modulate cellular functional activity.

Yet another further aspect of the present invention relates to the use of an agent capable of modulating the expression of sphingosine kinase or modulating the activity of sphingosine kinase in the manufacture of a medicament for the modulation of cellular functional activity.

A further aspect of the present invention relates to the use of sphingosine kinase or sphingosine kinase in the manufacture of a medicament for the modulation of cellular functional activity.

Still yet another aspect of the present invention relates to agents for use in modulating sphingosine kinase expression or sphingosine kinase activity wherein said modulation results in modulation of cellular functional activity.

Another aspect of the present invention relates to sphingosine kinase or sphingosine kinase for use in modulating cellular functional activity.

In a related aspect of the present invention, the mammal undergoing treatment may be a human or an animal in need of therapeutic or prophylactic treatment.

In yet another further aspect the present invention contemplates a pharmaceutical composition comprising sphingosine kinase, sphingosine kinase or an agent capable of modulating sphingosine kinase expression or sphingosine kinase activity together with one or more pharmaceutically acceptable carriers and/or diluents. Sphingosine kinase, sphingosine kinase or said agent are referred to as the active ingredients.

Yet another aspect of the present invention contemplates a method for detecting sphingosine kinase or sphingosine kinase mRNA in a biological sample from a subject said method comprising contacting said biological sample with an antibody specific for sphingosine kinase or sphingosine kinase mRNA or its derivatives or homologous for a time and under conditions sufficient for an antibody-sphingosine kinase or antibody-sphingosine kinase mRNA complex to form, and then detecting said complex.

Single and three letter abbreviations used throughout the specification are defined in Table 1.

TABLE 1

Single and three letter amino acid abbreviations

| Amino Acid | Three-letter Abbreviation | One-letter Symbol |
| --- | --- | --- |
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | The | T |
| Tryptophan | Trp | W |
| Tyrosine | Tyr | Y |

TABLE 1-continued

Single and three letter amino acid abbreviations

| Amino Acid | Three-letter Abbreviation | One-letter Symbol |
| --- | --- | --- |
| Valine | Val | V |
| Any residue | Xaa | X |

BRIEF DESCRIPTION OF THE DRAWINGS

FIG. 9 (i)–(iv) is a schematic representation of the sequence comparison of human sphingosine kinase with other known and putative sphingosine kinases. Comparison of the deduced human sphingosine kinase amino acid sequence with the amino acid sequences of the murine (mSK1a (SEQ ID NOs:9–16) and mSK1b (SEQ ID NOs:17–24); Kohama et al., 1998) and *S. cerevisiae* (LCB4 (SEQ ID NOs:25–32) and LCB5 (SEQ ID NOs:33–40); Nagiec et al., 1998) sphingosine kinases, and EST sequences of putative sphingosine kinases from *S. pombe* (SEQ ID NOs:41–48) and *C. elegans* (SEQ ID NOs:49–56) (Genbank™ accession numbers Z98762 and Z66494, respectively). Although the amino acid sequence similarity to human sphingosine kinase was high (36% identity), the A. thaliana putative sphingosine kinase sequence (Genbank™ accession number AL022603) gave relatively poor alignment and, for clarity, is not shown. The consensus sequence represents amino acids that are conserved in at least six of the seven aligned sequences, while conservation of structurally similar amino acids are denoted with an asterisk. Multiple sequence alignment was performed with CLUSTALW, and percentage identities to the human sphingosine kinase were determined using the GAP algorithm (Needleman & Wunsch, 1970). number AL022603) gave relativey poor alignment and, for clarity, is not shown. The consensus sequence represents amino acids that are conserved in at least six of the seven aligned sequences, while conservation of structurally similar amino acids are denoted with an asterisk. Multiple sequence alignment was performed with CLUSTALW, and percentage identities to the human sphingosine kinase were determined using the GAP algorithm (Needleman & Wunsch, 1970).

DETAILED DESCRIPTION OF THE INVENTION

Figure 1:
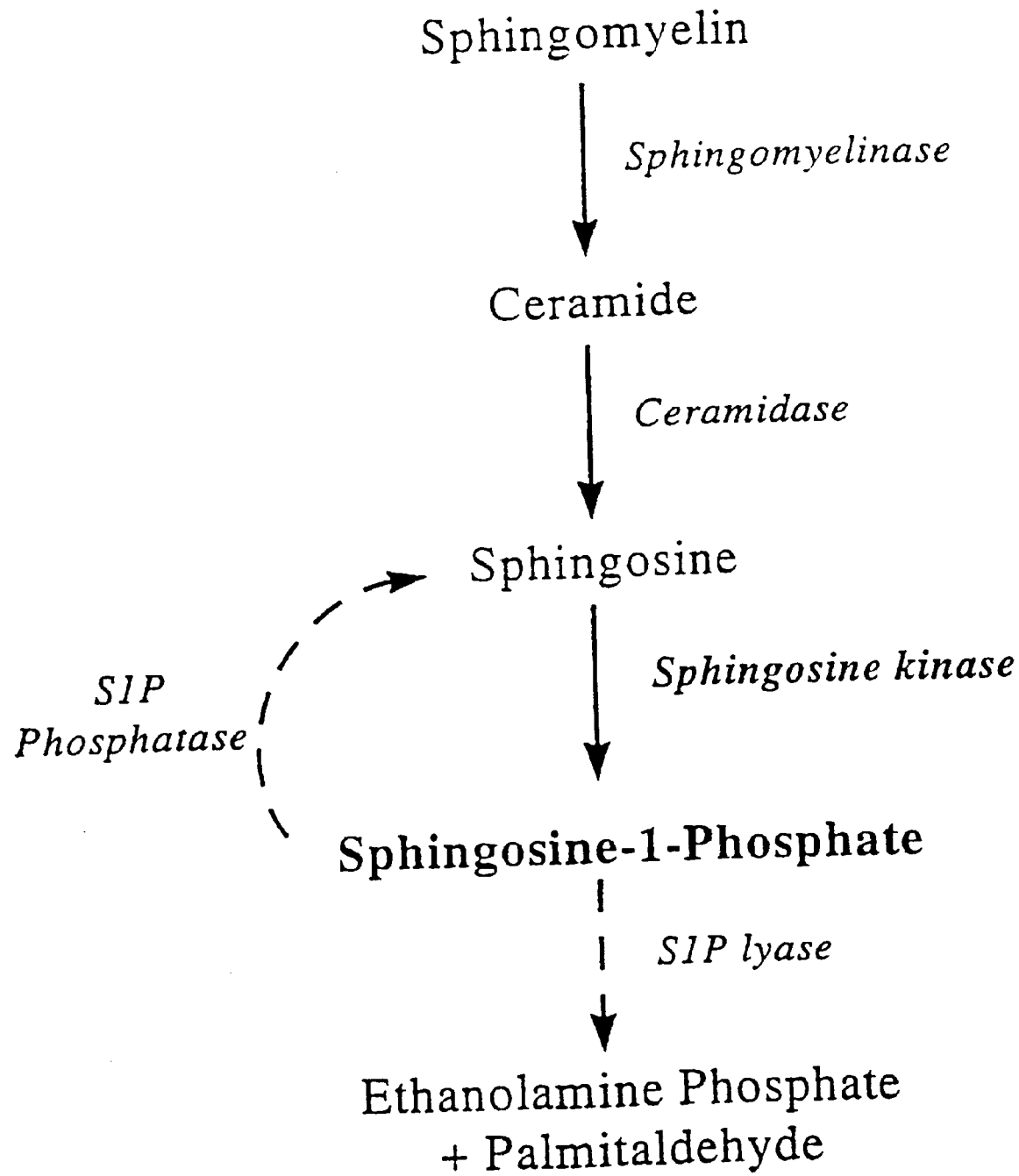
FIG. 1 is a schematic representation of the 'Sphingomyelin pathway'.

The present invention is predicated, in part, on the purification and cloning of a novel sphingosine kinase molecule. The identification of this novel molecule permits the identification and rational design of a range of products for use in therapy, diagnosis and antibody generation, for example for use in signal transduction. These therapeutic molecules may also act as either antagonists or agonists of sphingosine kinase function and will be useful, infer alia, in the modulation of cellular activation in the treatment of disease conditions characterised by unwanted cellular activity.

Accordingly, one aspect of the present invention provides an isolated nucleic acid molecule or derivative or analogue thereof comprising a nucleotide sequence encoding or complementary to a sequence encoding a novel sphingosine kinase protein or a derivative or mimetic of said sphingosine kinase protein.

Reference to "sphingosine kinase" should be understood as a reference to the molecule which is, inter alia, involved in the generation of sphingosine-1-phosphate during the activation of the sphingosine kinase signalling pathway. Reference to "sphingosine kinase" in italicised text should be understood as a reference to the sphingosine kinase nucleic acid molecule. Reference to "sphingosine kinase" in non-italicised text should be understood as a reference to the sphingosine kinase protein molecule.

More particularly, the present invention provides an isolated nucleic acid molecule or derivative or analogue thereof comprising a nucleotide sequence encoding of complementary to a sequence encoding a human sphingosine kinase protein or a derivative or mimetic of said sphingosine kinase protein.

In a preferred embodiment, the present invention provides a nucleic acid molecule or derivative or analogue thereof comprising a nucleotide sequence encoding, or a nucleotide sequence complementary to a nucleotide sequence encoding, an amino acid sequence substantially as set forth in SEQ ID NO:2 or a derivative or mimetic thereof or having at least about 45% or greater similarity to at least 10 contiguous amino acids in SEQ ID NO:2. substantially as set forth in <400>2 or a derivative or mimetic thereof or having at least about 45% or greater similarity to at least 10 contiguous amino acids in <400>2.

The term "similarity" as used herein includes exact identity between compared sequences at the nucleotide or amino acid level. Where there is non-identity at the nucleotide level, "similarity" includes differences between sequences which result in different amino acids that are nevertheless related to each other at the structural, functional, biochemical and/or conformational levels. Where there is non-identity at the amino acid level, "similarity" includes amino acids that are nevertheless related to each other at the structural, functional, biochemical and/or conformational levels. The percentage similarity may be greater than 50% such as at least 70% or at least 80% or at least 90% or at least 95% or higher.

Another aspect of the present invention contemplates a nucleic acid molecule or derivative or analogue thereof comprising a nucleotide sequence substantially as set forth in SEQ ID NO:1 or a derivative thereof, or capable of hybridising to SEQ ID NO:1 under low stringency conditions.

Reference herein to a low stringency includes and encompasses from at least about 0% v/v to at least about 15% v/v formamide and from at least about 1M to at least about 2M salt for hybridisation, and at least about 1M to at least about 2M salt for washing conditions. Alternative stringency conditions may be applied where necessary, such as medium stringency, which includes and encompasses from at least about 16% v/v to at least about 30% v/v formamide and from at least about 0.5M to at least about 0.9M salt for hybridisation, and at least about 0.5M to at least about 0.9M salt for washing conditions, or high stringency, which includes and encompasses from at least about 31% v/v to at least about 50% v/v formamide and from at least about 0.01M to at least about 0.15M salt for hybridisation, and at least about 0.01M to at least about 0.15M salt for washing conditions. Stringency may be measured using a range of temperature such as from about 40° C. to about 65° C. Particularly useful stringency conditions are at 42° C. In general, washing is carried out at $T_m=69.3+0.41$ (G+C)% [19]=−12° C. However, the $T_m$ of a duplex DNA decreases by 1° C. with every increase of 1% in the number of mismatched based pairs (Bonner et al (1973) *J.Mol.Biol*, 81:123).

Preferably, the present invention contemplates a nucleic acid molecule or derivative or analogue thereof comprising a nucleotide sequence substantially as set forth in SEQ ID NO:1 or a derivative thereof or capable of hybridising to SEQ ID NO:1 under low stringency conditions and which encodes an amino acid sequence corresponding to an amino acid sequence set forth in SEQ ID NO:2 or a sequence having at least about 45% similarity to at least 10 contiguous amino acids in SEQ ID NO:2.

More particularly, the present invention contemplates a nucleic acid molecule comprising a sequence of nucleotides substantially as set forth in SEQ ID NO:1.

The nucleic acid molecule according to this aspect of the present invention corresponds herein to human sphingosine kinase. Without limiting the present invention to any one theory or mode of action, the protein encoded by sphingosine kinase is a key element in the functioning of the sphingosine kinase signalling pathway. Sphingosine kinase acts to facilitate the generation of the second messenger, sphingosine-1-phosphate, and may be activated by:

(a) post-translational modifications such as phosphorylation or proteolytic cleavage;

(b) protein-protein interactions such as dimerisation, and G protein-coupled receptor mediated interactions;

(c) translocational events where the enzyme is targeted to an environment that increases catalytic activity or allows access to its substrate.

The expression product of the human sphingosine kinase nucleic acid molecule is human sphingosine kinase. Sphingosine kinase is defined by the amino acid sequence set forth in SEQ ID NO:2. The cDNA sequence for sphingosine kinase is defined by the nucleotide sequence set forth in SEQ ID NO:1. The nucleic acid molecule encoding sphingosine kinase is preferably a sequence of deoxyribonucleic acids such as a cDNA sequence or a genomic sequence. A genomic sequence may also comprise exons and introns. A genomic sequence may also include a promoter region or other regulatory regions.

Another aspect of the present invention contemplates a genomic nucleic acid molecule or derivative thereof capable of hybridising to SEQ ID NO:1 or a derivative thereof under low stringency conditions at 42° C.

Reference herein to sphingosine kinase and sphingosine kinase should be understood as a reference to all forms of human sphingosine kinase and sphingosine kinase, respectfully, including, for example, any peptide and cDNA isoformns which arise from alternative splicing of sphingosine kinase mRNA, mutants or polymorphic variants of sphingosine kinase or sphingosine kinase, the post-translation modified form of sphingosine kinase or the non-post-translation modified form of sphingosine kinase. To the extent that it is not specified, reference herein to sphingosine kinase and sphingosine kinase includes reference to derivatives, analogues, chemical equivalents and mimetics thereof.

The protein and/or gene is preferably from the human. However, the protein and/or gene may also be isolated from other animal or non-animal species.

Derivatives include fragments, parts, portions, mutants, variants and mimetics from natural, synthetic or recombinant sources including fusion proteins. Parts or fragments include, for example, active regions of sphingosine kinase. Derivatives may be derived from insertion, deletion or substitution of amino acids. Amino acid insertional derivatives include amino and/or carboxylic terminal fusions as well as intrasequence insertions of single or multiple amino acids. Insertional amino acid sequence variants are those in which one or more amino acid residues are introduced into a predetermined site in the protein although random insertion is also possible with suitable screening of the resulting product. Deletional variants are characterized by the removal of one or more amino acids from the sequence. Substitutional amino acid variants are those in which at least one residue in the sequence has been removed and a different residue inserted in its place. An example of substitutional amino acid variants are conservative amino acid substitutions. Conservative amino acid substitutions typically include substitutions within the following Groups: glycine and alanine; valine, isoleucine and leucine; aspartic acid and glutamic acid; asparagine and glutamine; serine and threonine; lysine and arginine; and phenylalanine and tyrosine. Additions to amino acid sequences including fusions with other peptides, polypeptides or proteins.

Chemical and functional equivalents of sphingosine kinase or sphingosine kinase should be understood as molecules exhibiting any one or more of the functional activities of sphingosine kinase or sphingosine kinase and may be derived from any source such as being chemically synthesized or identified via screening processes such as natural product screening.

The derivatives of sphingosine kinase include fragments having particular epitopes or parts of the entire sphingosine kinase protein fused to peptides, polypeptides or other proteinaceous or non-proteinaceous molecules.

Analogues of sphingosine kinase contemplated herein include, but are not limited to, modification to side chains, incorporating of unnatural amino acids and/or their derivatives during peptide, polypeptide or protein synthesis and the use of crosslinkers and other methods which impose conformational constraints on the proteinaceous molecules or their analogues.

Derivatives of nucleic acid sequences may similarly be derived from single or multiple nucleotide substitutions, deletions and/or additions including fusion with other nucleic acid molecules. The derivatives of the nucleic acid molecules of the present invention include oligonucleotides, PCR primers, antisense molecules, molecules suitable for use in cosuppression and fusion of nucleic acid molecules. Derivatives of nucleic acid sequences also include degenerate variants.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2, 4, 6-trinitrobenzene suiphonic acid (TNBS); acylation of amino groups with succinic anhydride and tetrahydrophthalic anhydride; and pyridoxylation of lysine with pyridoxal-5-phosphate followed by reduction with NaBH$_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides; Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carboethoxylation with diethylpyrocarbonate.

Examples of incorporating unnatural amino acids and derivatives during protein synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acid contemplated herein is show in Table 2.

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtnp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |

TABLE 2-continued

| Non-conventional amino acid | Code | Non-conventional amino acid | Code |
| --- | --- | --- | --- |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-2,2-diphenylethyl) carbamylmethyl)glycine | Nnbhm | N-(N-(3,3-diphenylpropyl) carbamylmethyl)glycine | Nnbhe |
| 1-carboxy-1-(2,2-diphenyl-ethylamino)cyclopropane | Nmbc | | |

Crosslinkers can be used, for example, to stabilise 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety.

The nucleic acid molecule of the present invention is preferably in isolated form or ligated to a vector, such as an expression vector. By "isolated" is meant a nucleic acid molecule having undergone at least one purification step and this is conveniently defined, for example, by a composition comprising at least about 10% subject nucleic acid molecule, preferably at least about 20%, more preferably at least about 30%, still more preferably at least about 40–50%, even still more preferably at least about 60–70%, yet even still more preferably 80–90% or greater of subject nucleic acid molecule relative to other components as determined by molecular weight, encoding activity, nucleotide sequence, base composition or other convenient means. The nucleic acid molecule of the present invention may also be considered, in a preferred embodiment, to be biologically pure.

The term "protein" should be understood to encompass peptides, polypeptides and proteins. The protein may be glycosylated or unglycosylated and/or may contain a range of other molecules fused, linked, bound or otherwise associated to the protein such as amino acids, lipids, carbohydrates or other peptides, polypeptides or proteins. Reference hereinafter to a "protein" includes a protein comprising a sequence of amino acids as well as a protein associated with other molecules such as amino acids, lipids, carbohydrates or other peptides, polypeptides or proteins.

In a particularly preferred embodiment, the nucleotide sequence corresponding to sphingosine kinase is a cDNA sequence comprising a sequence of nucleotides as set forth in SEQ ID NO:1 or a derivative or analogue thereof including a nucleotide sequence having similarity to SEQ ID NO:1.

A derivative of a nucleic acid molecule of the present invention also includes a nucleic acid molecule capable of hybridising to a nucleotide sequence as set forth in SEQ ID NO:1 under low stringency conditions. Preferably, low stringency is at 42° C.

The nucleic acid molecule may be ligated to an expression vector capable of expression in a prokaryotic cell (e.g. *E. coli*) or a eukaryotic cell (e.g. yeast cells, fungal cells, insect cells, mammalian cells or plant cells). The nucleic acid molecule may be ligated or fused or otherwise associated with a nucleic acid molecule encoding another entity such as, for example, a signal peptide. It may also comprise additional nucleotide sequence information fused, linked or otherwise associated with it either at the 3' or 5' terminal portions or at both the 3' and 5' terminal portions. The nucleic acid molecule may also be part of a vector, such as an expression vector. The latter embodiment facilitates production of recombinant forms of sphingosine kinase which forms are encompassed by the present invention.

The present invention extends to the expression product of the nucleic acid molecules as hereinbefore defined.

The expression product is sphingosine kinase having an amino acid sequence set forth in SEQ ID NO:2 or is a derivative, analogue or chemical equivalent or mimetic thereof as defined above or is a derivative or mimetic having an amino acid sequence of at least about 45% similarity to at least 10 contiguous amino acids in the amino acid sequence as set forth in <400>2 or a derivative or mimetic thereof.

Another aspect of the present invention is directed to an isolated protein selected from the list consisting of:

(i) A novel sphingosine kinase protein or a derivative, analogue, chemical equivalent or mimetic thereof.

(ii) A human sphingosine kinase protein or a derivative, analogue, chemical equivalent or mimetic thereof (iii) A protein having an amino acid sequence substantially as set forth in SEQ ID NO:2 or a derivative or mimetic thereof or a sequence having at least about 45% similarity to at least 10 contiguous amino acids in SEQ ID NO:2 or a derivative, analogue, chemical equivalent or mimetic of said protein.

(iv) A protein encoded by a nucleotide sequence substantially as set forth in SEQ ID NO:1 or a derivative or analogue thereof or a sequence encoding an amino acid sequence having at least about 45% similarity to at least 10 contiguous amino acids in SEQ ID NO:2 or a derivative, analogue, chemical equivalent or mimetic of said protein.

(v) A protein encoded by a nucleic acid molecule capable of hybridising to the nucleotide sequence as set forth in SEQ ID NO:1 or a derivative or analogue thereof under low stringency conditions and which encodes an amino acid sequence substantially as set forth in SEQ ID NO:2 or a derivative or mimetic thereof or an amino acid sequence having at least about 45% similarity to at least 10 contiguous amino acids in SEQ ID NO:2.

vi) A protein as defined in paragraphs (i) or (ii) or (iii) or (iv) or (v) in a homodimeric form.

vii) A protein as defined in paragraphs (i) or (ii) or (iii) or (iv) or (v) in a heterodimeric form.

The protein of the present invention is preferably in isolated form. By "isolated" is meant a protein having undergone at least one purification step and this is conveniently defined, for example, by a composition comprising at least about 10% subject protein, preferably at least about 20%, more preferably at least about 30%, still more preferably at least about 40–50%, even still more preferably at least about 60–70%, yet even still more preferably 80–90% or greater of subject protein relative to other components as determined by molecular weight, amino acid sequence or other convenient means. The protein of the present invention may also be considered, in a preferred embodiment, to be biologically pure.

The sphingosine kinase of the present invention may be in multimeric form meaning that two or more molecules are associated together. Where the same sphingosine kinase molecules are associated together the complex is a homomultimer. An example of a homomultimer is a homodimer. Where at least one sphingosine kinase is associated with at least one non-sphingosine kinase molecule, then the complex is a heteromultimer such as a heterodimer.

The ability to produce recombinant sphingosine kinase permits the large scale production of sphingosine kinase for commercial use. The sphingosine kinase may need to be produced as part of a large peptide, polypeptide or protein which may be used as is or may first need to be processed in order to remove the extraneous proteinaceous sequences. Such processing includes digestion with proteases, peptidases and amidases or a range of chemical, electrochemical, sonic or mechanical disruption techniques.

Notwithstanding that the present invention encompasses recombinant proteins, chemical synthetic techniques are also preferred in synthesis of sphingosine kinase.

Sphingosine kinase according to the present invention is conveniently synthesised based on molecules isolated from the human. Isolation of the human molecules may be accomplished by any suitable means such as by chromotographic separation, for example using CM-cellulose ion exchange chromatography followed by Sephadex (e.g. G-50 column) filtration. Many other techniques are available including HPLC, PAGE amongst others.

Sphingosine kinase may be synthesised by solid phase synthesis using F-moc chemistry as described by Carpino et al. (1991). Sphingosine kinase and fragments thereof may also be synthesised by alternative chemistries including, but not limited to, t-Boc chemistry as described in Stewart et al. (1985) or by classical methods of liquid phase peptide synthesis.

Without limiting the theory or mode of action of the present invention, sphingosine kinase is a key regulatory enzyme in the activity of the sphingosine kinase signalling pathway. By "sphingosine kinase signalling pathway" is meant a signalling pathway which utilises one or both of sphingosine kinase and/or sphingosine-1-phosphate. It is thought that a sphingosine kinase signalling pathway cascade which results in adhesion molecule expression may take the form of:

(i) the generation of ceramide from sphingomyelin via S.Mase activity, said ceramide being converted to sphingosine;

(ii) sphingosine-1-phosphate (referred to hereinafter as "Sph-1-P") generation by stimulation of sphingosine kinase; and (iii) the activation of MEK/ERK and nuclear translocation of NF-κB downstream from Sph-1-P generation.

The sphingosine kinase signalling pathway is known to regulate cellular activities such as those which lead to inflammation, apoptosis and cell proliferation. For example, upregulation of the production of inflammatory mediators such as cytokines, chemokines, eNOS and upregulation of adhesion molecule expression. Said upregulation may be induced by a number of stimuli including, for example, inflammatory cytokines such as tumor necrosis factor-α (TNF-α) and interleukin-1 (IL-1), endotoxin, oxidised or modified lipids, radiation or tissue injury.

The cloning and sequencing of this gene and its expression product now provides additional molecules for use in the prophylactic and therapeutic treatment of diseases characterised by unwanted cellular activity, which activity is either directly or indirectly modulated via the activity of the sphingosine kinase signalling pathway. Examples of diseases involving unwanted sphingosine kinase regulated cellular activity include rheumatoid arthritis, asthma, atherosclerosis, meningitis, multiple sclerosis and septic shock. Accordingly, the present invention contemplates therapeutic and prophylactic uses of sphingosine kinase amino acid and nucleic acid molecules, in addition to sphingosine kinase agonistic and antagonistic agents, for the regulation of cellular functional activity, such as for example, regulation of inflammation.

The present invention contemplates, therefore, a method for modulating expression of sphingosine kinase in a subject, said method comprising contacting the sphingosine kinase gene with an effective amount of an agent for a time and under conditions sufficient to up-regulate or down-regulate or otherwise modulate expression of sphingosine kinase. For example, sphingosine kinase antisense sequences such as oligonucleotides may be introduced into a cell to down-regulate one or more specific functional activities of that cell. Conversely, a nucleic acid molecule encoding sphingosine kinase or a derivative thereof may be introduced to up-regulate one or more specific functional activities of any cell not expressing the endogenous sphingosine kinase gene.

Another aspect of the present invention contemplates a method of modulating activity of sphingosine kinase in a mammal, said method comprising administering to said mammal a modulating effective amount of an agent for a time and under conditions sufficient to increase or decrease sphingosine kinase activity.

Modulation of said activity by the administration of an agent to a mammal can be achieved by one of several techniques, including but in no way limited to introducing into said mammal a proteinaceous or non-proteinaceous molecule which:

(i) modulates expression of sphingosine kinase;
(ii) functions as an antagonist of sphingosine kinase;
(iii) functions as an agonist of sphingosine kinase.

Said proteinaceous molecule may be derived from natural or recombinant sources including fusion proteins or following, for example, natural product screening. Said non-proteinaceous molecule may be, for example, a nucleic acid molecule or may be derived from natural sources, such as for example natural product screening or may be chemically synthesised. The present invention contemplates chemical analogs of sphingosine kinase or small molecules capable of acting as agonists or antagonists of sphingosine kinase. Chemical agonists may not necessarily be derived from sphingosine kinase but may share certain conformational similarities. Alternatively, chemical agonists may be specifically designed to mimic certain physiochemical properties of sphingosine kinase. Antagonists may be any compound capable of blocking, inhibiting or otherwise preventing sphingosine kinase from carrying out its normal biological functions. Antagonists include monoclonal antibodies specific for sphingosine kinase, or parts of sphingosine kinase, and antisense nucleic acids which prevent transcription or translation of sphingosine kinase genes or mRNA in mammalian cells. Modulation of sphingosine kinase expression may also be achieved utilizing antigens, RNA, ribosomes, DNAzymes, RNA aptamers or antibodies.

Said proteinaceous or non-proteinaceous molecule may act either directly or indirectly to modulate the expression of sphingosine kinase or the activity of sphingosine kinase. Said molecule acts directly if it associates with sphingosine kinase or sphingosine kinase to modulate the expression or activity of sphingosine kinase or sphingosine kinase. Said molecule acts indirectly if it associates with a molecule other than sphingosine kinase or sphingosine kinase which other molecule either directly or indirectly modulates the expression or activity of sphingosine kinase or sphingosine kinase. Accordingly, the method of the present invention encompasses the regulation of sphingosine kinase or sphingosine kinase expression or activity via the induction of a cascade of regulatory steps which lead to the regulation of sphingosine kinase or sphingosine kinase expression or activity.

Another aspect of the present invention contemplates a method of modulating cellular functional activity in a mammal said method comprising administering to said mammal an effective amount of an agent for a time and under conditions sufficient to modulate the expression of a nucleotide sequence encoding sphingosine kinase or sufficient to modulate the activity of sphingosine kinase.

Yet another aspect of the present invention contemplates a method of modulating cellular functional activity in a mammal said method comprising administering to said mammal an effective amount of sphingosine kinase or sphingosine kincase.

The sphingosine kinase, sphingosine kinase or agent used may also be linked to a targeting means such as a monoclonal antibody, which provides specific delivery of the sphingosine kinase, sphingosine kinase or agent to the target cells.

In a preferred embodiment of the present invention, the sphingosine kinase, sphingosine kinase or agent used in the method is linked to an antibody specific for said target cells to enable specific delivery to these cells.

Reference to "modulating cellular functional activity" is a reference to up-regulating, down-regulating or otherwise altering any one or more of the activities which a cell is capable of performing such as, but not limited to, one or more of chemokine production, cytokine production, nitric oxide synthesase, adhesion molecule expression and production of other inflammatory modulators.

Administration of the sphingosine kinase, sphingosine kinase or agent, in the form of a pharmaceutical composition, may be performed by any convenient means. Sphingosine kinase, sphingosine kinase or agent of the pharmaceutical composition are contemplated to exhibit therapeutic activity when administered in an amount which depends on the particular case. The variation depends, for example, on the human or animal and the sphingosine kinase, sphingosine kinase or agent chosen. A broad range of doses may be applicable. Considering a patient, for example, from about 0.1 mg to about 1 mg of sphingosine kinase or agent may be administered per kilogram of body weight per day. Dosage regimes may be adjusted to provide the optimum therapeutic response. For example, several divided doses may be administered daily, weekly, monthly or other suitable time intervals or the dose may be proportionally reduced as indicated by the exigencies of the situation. The sphingosine kinase or agent may be administered in a convenient manner such as by the oral, intravenous (where water soluble), intrannasal, intraperitoneal, intramuscular, subcutaneous, intradermal or suppository routes or implanting (e.g. using slow release molecules). With particular reference to use of sphingosine kinase or agent, these peptides may be administered in the form of pharmaceutically acceptable nontoxic salts, such as acid addition salts or metal complexes, e.g. with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. If the active ingredient is to be administered in tablet form, the tablet may contain a binder such as tragacanth, corn starch or gelatin; a disintegrating agent, such as alginic acid; and a lubricant, such as magnesium stearate.

A further aspect of the present invention relates to the use of the invention in relation to mammalian disease conditions. For example, the present invention is particularly useful, but in no way limited to, use in inflammatory diseases.

Accordingly, another aspect of the present invention relates to a method of treating a mammal said method comprising administering to said mammal an effective amount of an agent for a time and under conditions sufficient to modulate the expression of sphingosine kinase or sufficient to modulate the activity of sphingosine kinase wherein said modulation results in modulation of cellular functional activity.

In another aspect the present invention relates to a method of treating a mammal said method comprising administering to said mammal an effective amount of sphingosine kinase or sphingosine kinase for a time and under conditions sufficient to modulate cellular functional activity.

Yet another aspect of the present invention relates to the use of an agent capable of modulating the expression of sphingosine kinase or modulating the activity of sphingosine kinase in the manufacture of a medicament for the modulation of cellular functional activity.

A further aspect of the present invention relates to the use of sphingosine kinase or sphingosine kinase in the manufacture of a medicament for the modulation of cellular functional activity.

Still yet another aspect of the present invention relates to agents for use in modulating sphingosine kinase expression or sphingosine kinase activity wherein said modulation results in modulation of cellular functional activity.

Another aspect of the present invention relates to sphingosine kinase or sphingosine kinase for use in modulating cellular functional activity.

In a related aspect of the present invention, the mammal undergoing treatment may be a human or an animal in need of therapeutic or prophylactic treatment.

In yet another further aspect the present invention contemplates a pharmaceutical composition comprising sphingosine kinase, sphingosine kinase or an agent capable of modulating sphingosine kinase expression or sphingosine kinase activity together with one or more pharmaceutically acceptable carriers and/or diluents. Sphingosine kinase, sphingosine kinase or said agent are referred to as the active ingredients.

The pharmaceutical forms suitable for injectable use include sterile aqueous solutions (where water soluble) and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The preventions of the action of microorganisms can be brought about by various antibacterial and antifungal agents, for example, parabens, chlorobutanol, phenol, sorbic acid, thirmerosal and the like, In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When sphingosine kinase, sphingosine kinase and sphingosine kinase modulators are suitably protected they may be orally administered, for example, with an inert diluent or with an assimilable edible carrier, or they may be enclosed in hard or soft shell gelatin capsule, or they may be compressed into tablets, or they may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions in such that a suitable dosage will be obtained. Preferred compositions or preparations according to the present invention are prepared so that an oral dosage unit form contains between about 0.1 $\mu$g and 2000 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound may be incorporated into sustained-release preparations and formulations.

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired.

The principal active ingredient is compounded for convenient and effective administration in effective amounts with a suitable pharmaceutically acceptable carrier in dosage unit form as hereinbefore disclosed. A unit dosage form can, for example contain the principal active compound in amounts ranging from 0.5 $\mu$g to about 2000 mg. Expressed in proportions, the active compound is generally present in from about 0.5 $\mu$g to about 2000 mg/ml of carrier. In the case of compositions containing supplementary active ingredients, the dosages are determined by reference to the usual dose and manner of administration of the said ingredients.

The pharmaceutical composition may also comprise genetic molecules such as a vector capable of transfecting target cells where the vector carries a nucleic acid molecule capable of expressing sphingosine kinase, modulating sphingosine kinase expression or sphingosine kinase activity. The vector may, for example, be a viral vector.

Sphingosine kinase can also be utilised to create gene knockout models in either cells or animals, which knocked out gene is the sphingosine kinase gene expressed by said cells or animals. Accordingly in another aspect the present invention should be understood to extend to methods of creating sphingosine kinase gene cell or animal knockout models wherein sphingosine kinase has been utilised to facilitate knocking out of the endogenous sphingosine kinase gene of said cell or animal, and to the knockout models produced therefrom.

Still another aspect of the present invention is directed to antibodies to sphingosine kinase including catalytic antibodies. Such antibodies may be monoclonal or polyclonal and may be selected from naturally occurring antibodies to sphingosine kinase or may be specifically raised to sphingosine kinase. In the case of the latter, sphingosine kinase may first need to be associated with a carrier molecule. The antibodies and/or recombinant sphingosine kinase of the present invention are particularly useful as therapeutic or diagnostic agents.

Altenatively, fragments of antibodies may be used such as Fab fragments. Furthermore, the present invention extends to recombinant and synthetic antibodies and to antibody hybrids. A "synthetic antibody" is considered herein to include fragments and hybrids of antibodies. The antibodies of this aspect of the present invention are particularly useful for immunotherapy and may also be used as a diagnostic tool, for example, for monitoring the program of a therapeutic regime.

For example, sphingosine kinase can be used to screen for naturally occurring antibodies to sphingosine kinase. These may occur, for example in some inflammatory disorders.

For example, specific antibodies can be used to screen for sphingosine kinase proteins: The latter would be important, for example, as a means for screening for levels of sphingosine kinase in a cell extract or other biological fluid or purifying sphingosine kinase made by recombinant means from culture supernatant fluid. Techniques for the assays contemplated herein are known in the art and include, for example, sandwich assays, ELISA and flow cytometry.

It is within the scope of this invention to include any second antibodies (monoclonal, polyclonal or fragments of antibodies) directed to the first mentioned antibodies discussed above. Both the first and second antibodies may be used in detection assays or a first antibody may be used with a commercially available anti-immunoglobulin antibody. An antibody as contemplated herein includes any antibody specific to any region of sphingosine kinase.

Both polyclonal and monoclonal antibodies are obtainable by immunization with the protein or peptide derivatives and either type is utilizable for immunoassays. The methods of obtaining both types of sera are well known in the art. Polyclonal sera are less preferred but are relatively easily prepared by injection of a suitable laboratory animal with an effective amount of sphingosine kinase, or antigenic parts thereof, collecting serum from the animal, and isolating specific sera by any of the known immunoadsorbent techniques. Although antibodies produced by this method are utilizable in virtually any type of immunoassays, they are generally less favored because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art. (See, for example Douillard and Hoffman, Basic Facts about Hybridomas, in *Compendium of Immunology* Vol II, ed. by Schwartz, 1981: Kohler and Milstein, *Nature* 256: 495–499 1975; *European Journal of Immunology* 6: 511–519, 1976).

In another aspect of the present invention, the molecules of the present invention are also useful as screening targets for use in applications such as the diagnosis of disorders which are regulated by sphingosine kinase.

Yet another aspect of the present invention contemplates a method for detecting sphingosine kinase or sphingosine kinase mRNA in a biological sample from a subject said method comprising contacting said biological sample with an antibody specific for sphingosine kinase or sphingosine kinase mRNA or its derivatives or homologous for a time and under conditions sufficient for an antibody-sphingosine kinase or antibody-sphingosine kinase mRNA complex to form, and then detecting said complex.

The presence of sphingosine kinase may be determined in a number of ways such as by Western blotting, ELISA or flow cytometry procedures. Sphingosine kinase mRNA may be detected, for example, by in situ hybridization or Northern blotting. These, of course, include both single-site and two-site or "sandwich" assays of the non-competitive types, as well as in the traditional competitive binding assays. These assays also include direct binding of a labelled antibody to a target.

Sandwich assays are among the most useful and commonly used assays and are favoured for use in the present invention. A number of variations of the sandwich assay technique exist, and all are intended to be encompassed by the present invention. Briefly, in a typical forward assay, an unlabelled antibody is immobilized on a solid substrate and the sample to be tested brought into contact with the bound molecule. After a suitable period of incubation, for a period of time sufficient to allow formation of an antibody-antigen complex, a second antibody specific to the antigen, labelled with a reporter molecule capable of producing a detectable signal is then added and incubated, allowing time sufficient for the formation of another complex of antibody-antigen-labelled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of hapten. Variations on the forward assay include a simultaneous assay, in which both sample and labelled antibody are added simultaneously to the bound antibody. These techniques are well known to those skilled in the art, including any minor variations as will be readily apparent. In accordance with the present invention the sample is one which might contain sphingosine kinase including cell extract, tissue biopsy or possibly serum, saliva, mucosal secretions, lymph, tissue fluid and respiratory fluid. The sample is, therefore, generally a biological sample comprising biological fluid but also extends to fermentation fluid and supernatant fluid such as from a cell culture.

In the typical forward sandwich assay, a first antibody having specificity for the sphingosine kinase or antigenic parts thereof, is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2–40 minutes) and under suitable conditions (e.g. 25° C.) to allots binding of any sub unit present in the antibody. Following the incubation period, the antibody sub unit solid phase is washed and dried and incubated with a second antibody specific for a portion of the hapten. The second antibody is linked to a reporter molecule which is used to indicate the binding of the second antibody to the hapten.

An alternative method involves immobilizing the target molecules in the biological sample and then exposing the immobilized target to specific antibody which may or may not be labelled with a reponer molecule. Depending on the amount of target and the strength of the reporter molecule signal, a bound target may be detectable by direct labelling with the antibody. Alternatively, a second labelled antibody, specific to the first antibody is exposed to the target-first antibody complex to form a target-first antibody-second antibody tertiary complex. The complex is detected by the signal emitted by the reporter molecule.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e. radioisotopes) and chemiluminescent molecules.

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase and alkaline phosphatase, amongst others. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above. In all cases, the enzyme-labelled antibody is added to the first antibody hapten complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of hapten which was present in the sample. "Reporter molecule" also extends to use of cell agglutination or inhibition of agglutination such as red blood cells on latex beads, and the like.

Alternately, fluorescent compounds, such as fluorecein and rhodamine, may be chemically coupled to antibodies without altering their binding capacity. When activated by illumination with light of a particular wavelength, the fluorocrome-labelled antibody adsorbs the light energy, inducing a state to excitability in the molecule, followed by emission of the light at a characteristic color visually detectable with a light microscope. As in the EIA, the fluorescent labelled antibody is allowed to bind to the first antibody-hapten complex. After washing off the unbound reagent, the remaining tertiary complex is then exposed to the light of the appropriate wavelength the fluorescence observed indicates the presence of the hapten of interest. Immunofluorescene and EIA techniques are both very well established in the art and are particularly preferred for the present method. However, other reporter molecules, such as radioisotope, chemiluminescent or bioluminescent molecules, may also be employed.

The present invention also contemplates genetic assays such as involving PCR analysis to detect sphingosine kinase or its derivatives.

Further features of the present invention are more fully described in the following non-limiting examples.

EXAMPLE 1

Purification and Cloning of Human Sphingosine Kinase—Experimental Procedures

Materials

D-erythro-Sphingosine, D-erythro-dihydrosphingosine, DL-thieo-dihydrosphingosine, N,N-dimethylsphingosine, N-acetylsphingosine ($C_2$-ceramide). S1P and Fumosin B1 were purchased from Biomol Research Laboratories Inc. (Plymouth Meeting, Pa.). Phytosphingosine, L-α-phosphatidic acid. L-α-phosphatidylinositol, L-α-phosphatidylserine, L-α-phosphatidylcholine. L-α-phosphatidyldethanolamine. 1,2-dioctanoyl-sn-glycerol, 1,2-dioleoyl-sn-glycerol, ATP, calmodulin, glutathione and bovine serum albumin (BSA) were from Sigma. N,N,N-trimethylsphingosine and ADP were purchased from Calbiochem (Band Soden, Germany), [$\gamma^{32}$P]ATP from Geneworks (Adelaide, South Australia), TNFα from R&D Systems Inc. (Minneapolis, Minn.), and isopropyl-β-D-thiogalactoside (IPTG) from Promega (Madison, Wis.). Prepacked Mono-Q, Superose 75 and HiTrap-Q columns, Q Sepharose fast flow, calmodulin Sepharose 4B, glutathione Sepharose 4B, thrombin and gel filtration molecular mass protein standards were from Amersham Pharmacia Biotech. SDS-PAGE molecular mass protein standards, silver stain plus kit, Coomassie Brilliant Blue R250 and Coomassie protein reagent were from Bio-Rad. Centricon concentrators were purchased from Amicon Inc. (Beverly, Mass.) and BCA protein reagent was from Pierce Chemical Company (Rockford, Ill.).

Sphingosine Kinase Enzyme Assay

Sphingosine kinase activity was routinely determined using D-erythro-sphingosine and $[\gamma^{32}P]ATP$ as substrates, essentially as previously described (Olivera et al., 1998) with some modifications. Briefly, assays were performed by incubating samples at 37° C. for 30 min with sphingosine (100 μM stock dissolved in 5% Triton X-100) and $[\gamma^{-32}P]$ ATP (1 mM; 10 μCi/ml) in assay buffer containing 100 mM Tris/HCl (pH 7.4), 10 mM $MgCl_2$ 10% (v/v) glycerol, 1 mM dithiothreitol, 1 mM EGTA, 1 mM $Na_3VO_4$, 15 mM NaF, 0.5 mM 4-deoxypyridoxine in a total volume of 100 μl. Reactions were terminated and sphingosine-1-phosphate extracted by the addition of 700 μl of chloroform/methanol/HCl (100:200:1. v/v), followed by vigorous mixing, addition of 200 μp of chloroform and 200 μl of 2 M KCl, and phase separation by centrifugation. The labeled S1P in the organic phase was isolated by TLC on Silica Gel 60 with 1-butanol/ethanol/acetic acid/water (8:2:1:2, v/v) and quantitated by phosphorimager (Molecular Dynamics. Sunnyvale, Calif.). One unit (U) of activity is defined as 1pmol of S1P formed per minute.

Purification of Sphingosine Kiniase From Human Placenta

Sphingosine kinase was purified from 1240 g of human placenta (4 placentas), with all steps performed at 4° C. The placentas were diced, washed in buffer A (25 mM Tris/HCl buffer, pH 7.4 containing 10% (v/v) glycerol, 0.05% Triton X-100 and 1 mM dithiothreitol), transfered to 1.5 L of fresh buffer A containing a protease inhibitor cocktail (Complete™; Boehringer Mannheim) (buffer B), and minced in a Waring blender. The resultant homogenate was stored on ice for 30 min to enhance enzyme extraction, and the soluble fraction of the homogenate then isolated by centrifugation at 17 000 g for 60 min. This preparation was then fractionated by $(NH_4)_2SO_4$ precipitation by the addition of solid $(NH^4)^2SO^4$ at pH 7.4 and collection of the precipitated proteins by centrifugation (17 000 g, 30 min). The 25–35%-saturated $(NH_4)_2SO_4$ fraction was then redissolved in a buffer B, desalted by extensive dialysis against this same buffer, and centrifuged (17 000 g, 30 min) to remove insoluble material. All subsequent chomatographic steps were performed using a FPLC system (Pharmacia Biotech) at 4° C.

The dialysed $(NH_4)_2SO_4$ fraction was applied to a Q-Sepharose fast flow column (50 mm diameter, 250 ml bed volume) pre-equilibrated with buffer A at a flow rate of 7 ml/min. Sphingosine kinase activity was eluted with a NaCl gradient of 0 to 1 M in buffer A and collected in 10 ml fractions. Fractions containing highest SK1 activity were then combined, and $CaCl_2$ and NaCl added to give final concentrations of 4 mM and 250 mM, respectively. This pooled extract was then applied to a calmodulin-Sepharose 4B column (16 mm diameter, 10 ml bed volume), pre-equilibrated with buffer A containing 2 mM $CaCl_2$, at a flow rate of 1 ml/min. The column was then washed with several column volumes of equilibration buffer, followed by buffer A containing 4 mM EGTA, and then SB eluted with buffer A containing 4 mM EGTA and 1 M NaCl. The fractions containing highest sphingosine kinase activity were pooled, desalted on a Sephadex G-25 column, and applied at a flow rate of 1 ml/min to a Mono-Q column (5 mm diameter 1 ml bed volume) pre-equilibrated with buffer A. Sphingosine kinase activity was eluted with a NaCl gradient to 0 to 1M in buffer A. NaCl (to 500 mM) was immediately added to the fractions (1 ml) collected to stabilise enzyme activity. The Mono-Q fractions containing highest sphingosine kinase activity were combined and desalted on a Sephadex G-25 column. ATP and $MgCl_2$ were then added to the pooled fractions to a final concentrations of 1 mM and 5 mM, respectively, before reapplication at a flow rate of 1 ml/min to the Mono-Q column pre-equilibrated with buffer A containing 1 mM ATP and 5 mM $MgCl_2$. Sphingosine kinase activity was eluted with a NaCl gradient of 0 to 1M in the equilibration buffer. Again, NaCl (to 500 mM) was immediately added to the fractions (1 ml) collected to stabilise enzyme activity. The ATP-Mono-Q fractions containing highest sphingosine kinase activity were pooled and concentrated 10-fold to a final volume of 200 μl in a Centricon-10 concentrator and applied at a flow rate of 0.4 ml/min to a Superdex 75 column (10 mm diameter, 20 ml bed volume) pre-equilibrated with buffer A containing 500 mM NaCl. Sphingosine kinase activity was eluted with the same buffer and 0.4 ml fractions collected. The molecular mass of the enzyme was estimated from this column by comparison to the elution volumes of ribonuclease A, chymotrypsinogen A, ovalbumin and BSA.

Cloning of Human Sphingosine Kinase

The human sphingosine kinase (hSK) was amplified from a HUVEC λ Zap cDNA library using PCR primers derived from human EST sequences (GenBank access-ion numbers D31133, W63556, AA026479, AA232791, AA081152, AI769914 and AI769914) aligned to the murine sphingosine kinases (Olivera et al., 1998). These primers, spanning a central SacII site (P1, 5'-CGGAATTCCCAGTCGG CCGCGGTA-3' [SEQ ID NO:3] and P2, 5'-TAGAATTCTA CCGCGGCCGACTGGCT-3' [SEQ ID NO:4]), were used in combination with T3 and T7 primers to generate two overlapping PCR products of 669 bp and 550 bp that represented the 5' and 3' ends of hSK, respectively. These two PCR products were then separately cloned into pGEM4Z. A 584 bp SacII fragment from the 5' hSK PCR clone was then sub-cloned in the correct orientation into the SacII site of the 3' hSK PCR clone, to generate a 1130 bp partial hSK cDNA clone. A full length clone encoding hSK was then generated by sub-cloning a 120 bp EcoRI/StuI fragment from the 669 bp 5' hSK clone into this pGEM4Z-1130 bp clone digested with EcoRI/StuI. Sequencing the cDNA clone in both directions verified the integrity of the hSK cDNA sequence.

For mammalian cell expression the hSK cDNA was FLAG epitope tagged at the 3'-end by PFU polymerase PCR with oligonucleotide primers T7 and 5'-TAGAATTCAC TTGTCATCGTCGTCCTTGTAGTCTAAGGGCTCTTCT GGCGGT-3' [SEQ ID NO:5]. This FLAG-tagged hSK cDNA was then cloned into pcDNA3 by digestion with EcoRI. The orientation was determined by restriction analysis and sequencing verified the integrity of the hSK-FLAG cDNA sequence. For bacterial expression, the full length hSK cDNA was sub-cloned into pGEX4T2. The pGEM4Z-hSK clone was digested with BamHI and blunted with 3U PFU polymerase in 1×PFU buffer, 50 μM dNTP's at 72° C. for 30 minutes. The 1163 bp hSK cDNA was gel purified following digestion with SalI and the blunt/SalI fragment was then ligated to pGEX4T2 SmaI/XhoI.

Sphingosine Kinase Amino Acid Sequence Analysis

The human sphingosine kinase amino acid sequence was searched against non-redundant amino acid and nucleotide sequence databases at the Australian National Genome Information Service using the blastp and tblastn algorithms (Altschul et al., 1990).

Cell Culture

Human umbilical vein endothelial cells (HUVEC) were isolated as previously described (Wall et al., 1978) and cultured on gelatin-coated culture flasks in medium M199 with Earle's salts supplemented with 20% fetal calf serum, 25 µg/ml endothelial growth supplement (Collaborative Research) and 25 µg/ml heparin. The cells were passaged three times and grown to 80% confluency before treatment and harvesting. Human embryonic kidney cells (HEK293, ATCC CRL-1573) cells were cultured on Dulbecco's modified Eagle's medium containing 10% fetal calf serum, 2 mM glutamine, 0.2% (w/v) sodium bicarbonate, penicillin (1.2 mg/ml), and gentamycin (1.6 mg/ml). HEK293 cells were transiently transfected using the calcium phosphate precipitation method (Graham & van der Eb, 1973). Treatment of HUVEC and HEK293 cells with TNFα (1 ng/ml) was performed as previously described (Xia et al., 1998).

EXAMPLE 2

Expression and Isolation of Recombinant Human Sphingosine Kinase from *E. Coli*—Experimental Procedure The full length SPHK cDNA cloned into pGEX4T2 was transformed into *E. coli* BL21. Overnight cultures (100 ml) of transformed isolates were grown with shaking (200 rpm) at 30° C. in Superbroth (20 g/L glucose, 35 g/L tryptone, 20 g/L yeast extract, 5 g/L NaCl, pH 7.5) medium containing ampicillin (100 mg/L). The cultures were diluted 1:20 in fresh medium and grown at 30° C. with shaking to an $OD_{600}$ of 0.6–0.7. Expression of the glutathione-s-transferase (GST)-coupled sphingosine kinase (GST-SK) was then induced by addition of 0.1 mM isopropyl-β-D-thiogalactoside and further incubation of the cultures at 30° C. for 3 h. After this time the bacterial cells were then harvested by centrifugation at 6,000 g for 20 min at 4° C. and resuspended in 20 ml of buffer B containing 250 mM NaCl. the cells were then lysed with lysozyme at a final concentration of 0.3 mg/ml for 15 min at 25° C. followed by sonication, consisting of three cycles of 20 s ultrasonic pulses followed by one minute cooling. The lysate was then clarified by centrifugation at 50,000 g for 45 min at 4° C., followed by filtrating through 0.22 µm filters. To be filtered supernatant was then incubated with 0.2 volumes of 50% (w/v) glutathione-Sepharose 4B (Pharmacia) that was washed and pro-equilibrated with buffer B, for 60 min at 4° C. with constant mixing. After this time the mixture was poured into a glass chromatography column (10 mm diam.) and the beads (with bound GST-SK) washed with 10 column volumes of buffer B at 4° C. The GST-SK was then eluted from the column in 10 ml of buffer B containing 10 mM reduced glutathione. Cleavage of the GST away from sphingosine kinase was then performed by incubation with 20 µg (30 N.I.H. units) thrombin (Pharmacia) for 3 h at 25° C. The released sphingosine kinase was then purified by application of the cleavage mix to a calmodulin-Sepharose column and then a Mono-Q anion exchange column for the purification of the sphingosine kinase from human placenta. These columns resulted in purification of the recombinant sphingosine kinase to homogeneity.

EXAMPLE 3

Characterization of Sphingosine Kinases— Experimental Procedures

The effect of pH on the activity of the isolated sphingosine kinases was determined over the pH range 4.0 to 11.0 in 50 mM buffers (sodium acetate, pH 4.0–5.0; Mes, pH 6.0–7.0; Hepes, pH 7.0–8.2; Tris/HCl, pH 8.2–10.0: Caps, pH 10.0–11.0) at 37° C. pH stability was determined by assaying the residual activity after pre-incubation of the enzymes in the same buffers for 5 h at 4° C. Similarly, thermal stabilities were determined by assaying the residual activity after pre-incubation of the enzymes at various temperatures (4–80° C.) for 30 min at pH 7.4 (50 mM Tris/HCl containing 10% glycerol, 0.5 M NaCl and 0.05% Triton X-100). Substrate kinetics were analysed using Michaelis-Menten kinetics with a weighted non-linear regression program (Easterby, 1996). Since sphingosine and its analogues were added to the enzyme assays in mixed micelles with Triton X-100, where they exibit surface dilution kinetics (Buehrer and Bell. 1992), all K, and KC values obtained for these molecules were expressed as mol % of Triton X-100, rather than as bulk solution concentrations. For assays to determine the effect of calcium/calmodulin on sphingosine kinase activity, calcium and calmodulin were added to the standard assay mixtures containing 20 nM of isolated sphingosine kinase at final concentrations of 4 mM and 0.6 µM, respectively.

EXAMPLE 4

Other Analytical Methods

Protein was determined using either the Coomassie Brilliant Blue (Bradford-et al., 1976) or Bicinchoninic acid (Smith et al., 1985) reagents using BSA as standard. In some cases protein estimations were performed after concentration and removal of detergent by precipitation (Wessel and Flügge, 1984) to increase the sensitivity and accuracy of the determinations. SDS-PAGE was performed according to the method of Laemmli (1970) using 12% acrylamide gels. Protein bands on gels were visualised with either Coomassie Brilliant Blue R250 or silver staining. Molecular mass was estimated by comparison to the electophoritic mobility of myosin, β-galactosidase, BSA, ovalburninm, carbonic anhydrase soybean trypsin inhibitor, lysozyme and aprotinin.

EXAMPLE 5

Purification of Human Sphingosine Kinase— Results

Figure 2:
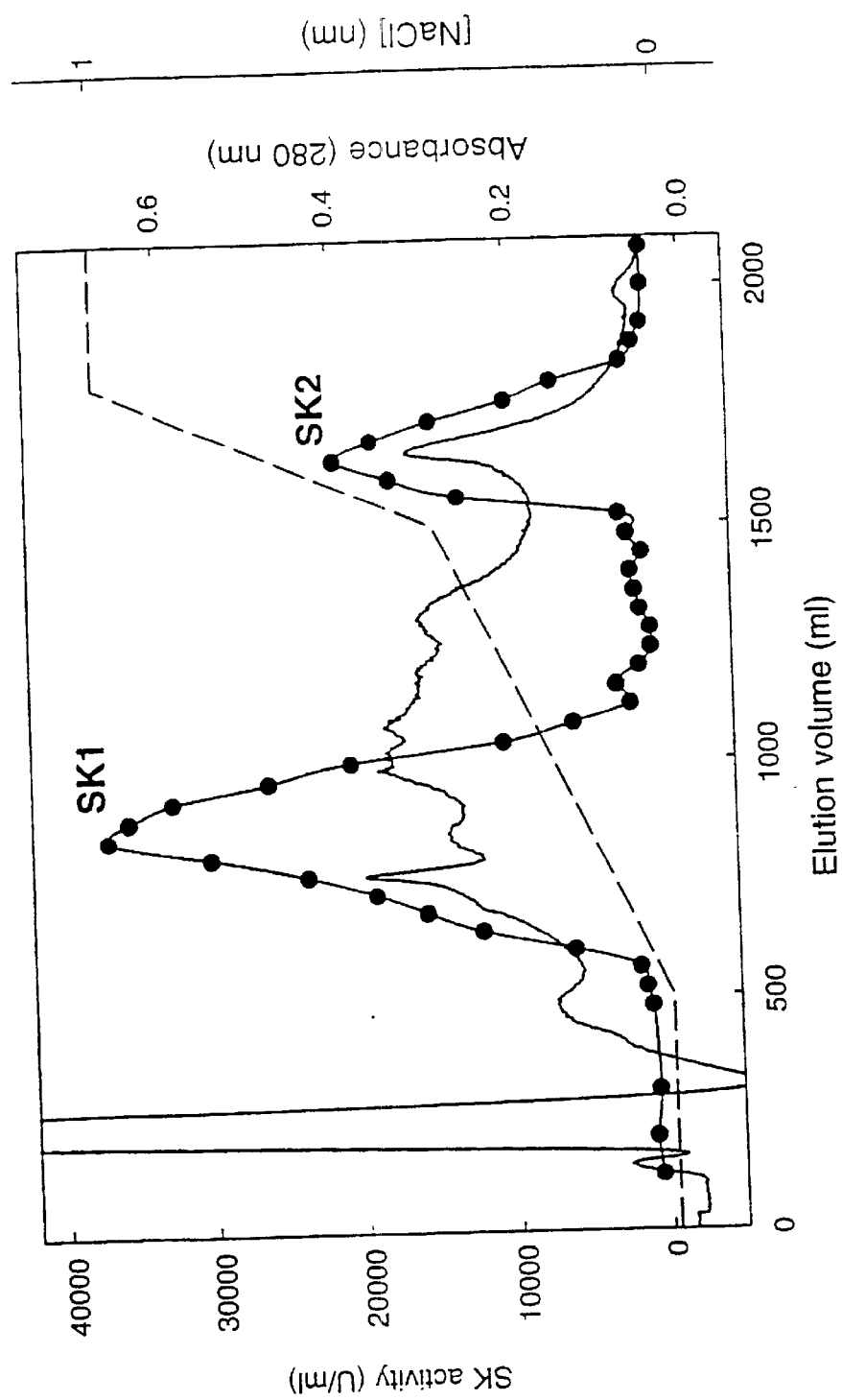
FIG. 2 is a graphical representation of anion exchange chromatography of human sphingosine kinase. A, Anion exchange chromatography with Q Sepharose fast flow of the $(NH_4)_2SO_4$ precipitated fraction of the human placenta extract showing two peaks of sphingosine kinase activity. Extracts were applied in buffer A and sphingosine kinase activity (●) was eluted with a NaCl gradient of 0 to 1M (----). Protein eluted was followed by absorbance at 280 nm (—).

Just over half of the total sphingosine kinase activity in human placenta was present in the cytosol after tissue homogenisation (Table 3). The purification of sphingosine kinase from human placenta is summarised in Table 4. The soluble fraction from the homogenate of four human placentae was initially subjected to ammonium sulphate precipitation. This resulted in a remarkably good purification of sphingosine kinase (33-fold), which precipitated in the 25–35% saturated ammonium sulphate fraction. For anion exchange chromatography the ammonium sulphate fraction was rapidly desalted through the use of Sephadex G25 column and the desalted fraction loaded immediately onto a Q Sepharose FF column. The speed of this desalting step appeared critical since the sphingosine kinase activity appeared very unstable at NaCl concentrations below about 0.2 M, meaning slower desalting steps, such as dialysis, resulted in substantial losses of enzyme activity. Application of a NaCl gradient of 0 to 1 M to the Q Sepharose FF column resulted in two peaks of sphingosine kinase activity, eluting at approximately 0.15 M and 0.6 M NaCl, and designated SK1 and SK2, respectively (FIG. 2). For this study SK1 was selected for further purification due to its greater abundance and stability; SK2 activity appeared very unstable and, unlike SK1, could not be stabilised by the addition of 0.5M NaCl, 10% glycerol and 0.05% Triton X-100. SK1 was also chosen since it appeared to be the isoform present in HUVEC, as discussed later.

Figure 3:
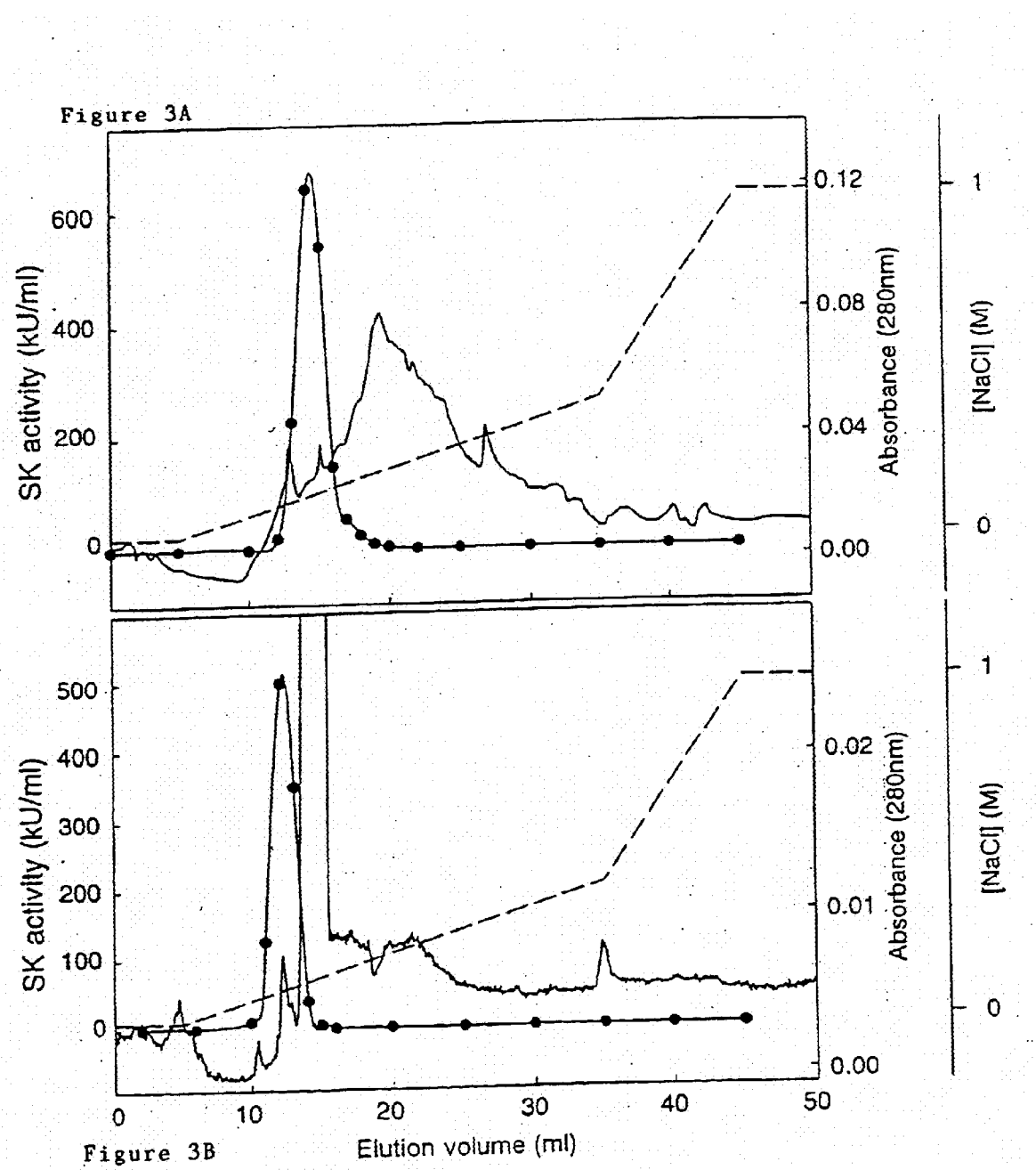
FIG. 3 is a graphical representation of the purification of human placenta SK1 by anion exchange chromatography. Purification on a Mono-Q column is enhanced by reapplication and elution from the same column in the presence of ATP. A, The fractions from the calmodulin-Sepharose 4b column containing sphingosine kinase activity were pooled, desalted and applied to the Mono-Q column in buffer A. B, Active fractions from the Mono-Q column were desalted and reapplied to the Mono-Q column in buffer A with: 1 mM ATP and 4 mM $MgCl_2$. In both cases sphingosine kinase activity (●) was eluted with a NaCl gradient of 0 to 1M(----), with protein elution followed by absorbance at 280 nm (—).
Figure 4:
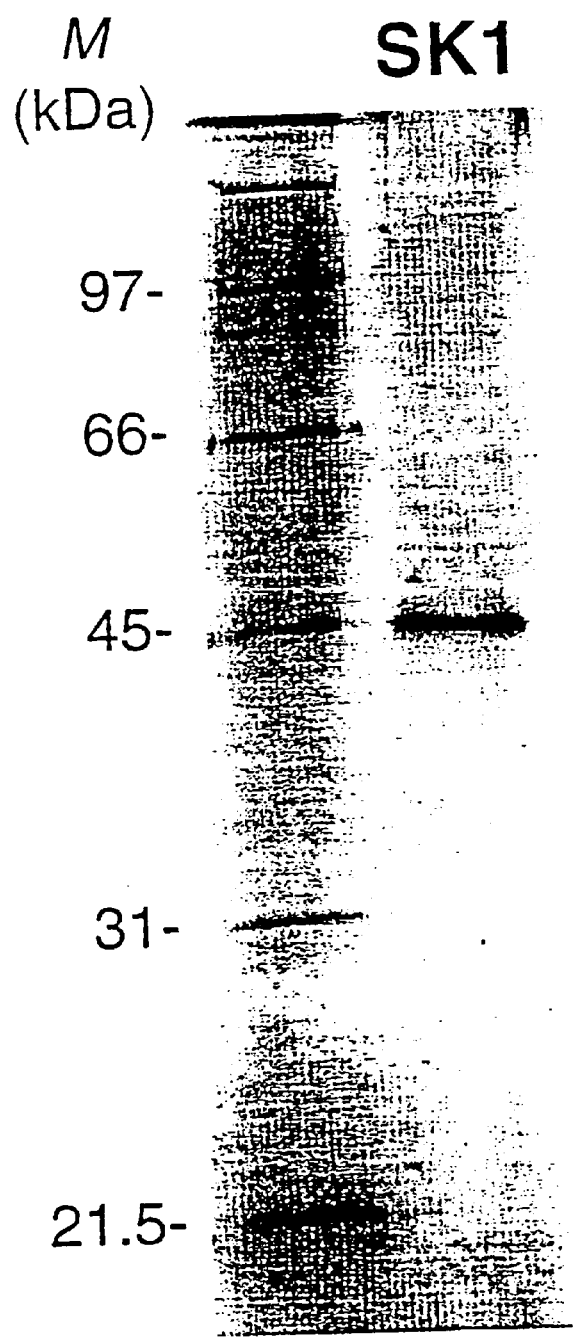
FIG. 4 is an image of SDS-PAGE of purified human placenta sphingosine kinase. The fraction from the Superdex 75 column containing the highest sphingosine kinase activity was applied to SDS-PAGE with silver staining, yielding a single band of 45 kDa.

Fractions from Q Sepharose FF column containing SK1 were then affinity purified by application to a calmodulin-Sepharose 4B column in the presence of 4 mM $CaCl_2$, and elution of SK1 performed with EGTA and NaCl, resulting in further substantial purification (38-fold) and high enzyme yields. SK1 could not be eluted from the calmodulin Sepharose 4B column with EGTA alone, indicating an unusual association of the enzyme with this affinity matrix. The active fractions that eluted from the calmodulin Sepharose 4B column were then desalted and applied to two subsequent steps of analystical anion exchange chromatography on a Mono Q column, with the second step performed in the presence of 1 mM ATP and 5 mM $MgCl_2$ (FIG. 3). The active fractions resulting from these anion exchange steps were then applied to gel filtration chromatography with a Superdex 75 column as a final purification step. SK1 eluted from this column as a single peak with a molecule mass corresponding to 44 kDa. Analysis of the active fraction from this final column by SDS-PAGE with silver staining (FIG. 4) revealed a single band of molecular mass 45 kDa, indicating a homogenous protein that has been purified over a million-fold from the original placenta extract with remarkably good yield of 7% of the original sphingosine kinase activity (Table 4). This is the first sphingosine kinase to be purified to homogeneity from a human source.

EXAMPLE 6

Sphingosine Kinase Isoforms in HUVEC—Results

Figure 5:
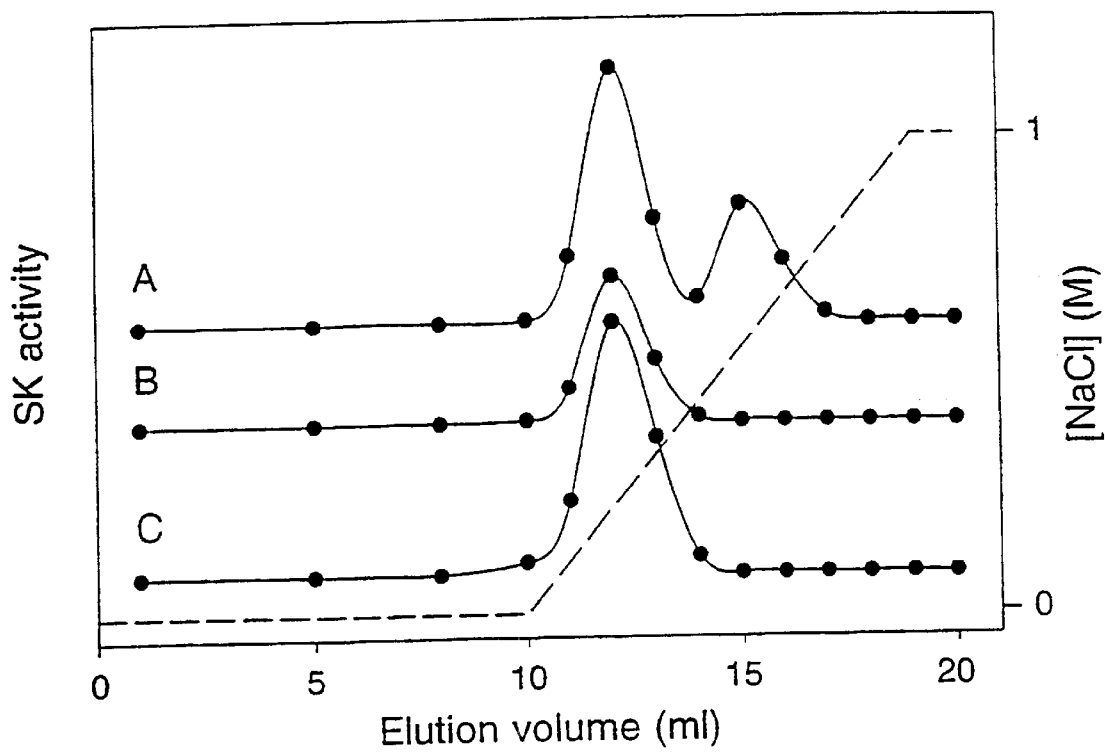
FIG. 5 is a graphical representation of preparative anion exchange chromatography. Only a single chromatographically identified sphingosine kinase isoform is present in HUVEC. Preparative anion exchange chromatography with HiTrap-Q columns of human placenta, HUVEC and TNFα treated HUVEC extracts showing, in HUVEC, the presence of a single sphingosine kinase peak that increases in activity following treatment of cells with TNFα. Cells were harvested, lysed and the soluble extracts applied to the HiTrap-Q column in buffer A. Total sphingosine kinase activity in human placenta, HUVEC and TNFα treated HUVEC extracts were 51, 78 and 136 U/mg proteins respectively Sphingosine kinase activity (□) was eluted with a NaCl gradient of 0 to 1M (----).

Since two sphingosine kinase activities were identified in human placenta (FIG. 2) we examined the multiplicity of this enzyme activity in HUVEC by the use of preparative anion exchange columns. In contrast to other human tissues and cells, application of HUVEC extracts to these columns resulted in the appearance of only a single sphingosine kinase peak that eluted at the same point as the human placenta SK1 (FIG. 5). 7 Similarly, only a single sphingosine kinase peak eluted after application of HUVEC extracts in which sphingosine kinase activity had been stimulated by 10 min treatment of HUVEC with TNFα (Xia el al., 1999). These results would indicate that SK1, the human placenta sphingosine kinase isolated in this study, is probably the main isoform found in HUVEC, and that TNFα treatment results in an increase in the activity of this enzyme, rather than the activation of another, otherwise latent, isoform.

EXAMPLE 7

Figure 6:
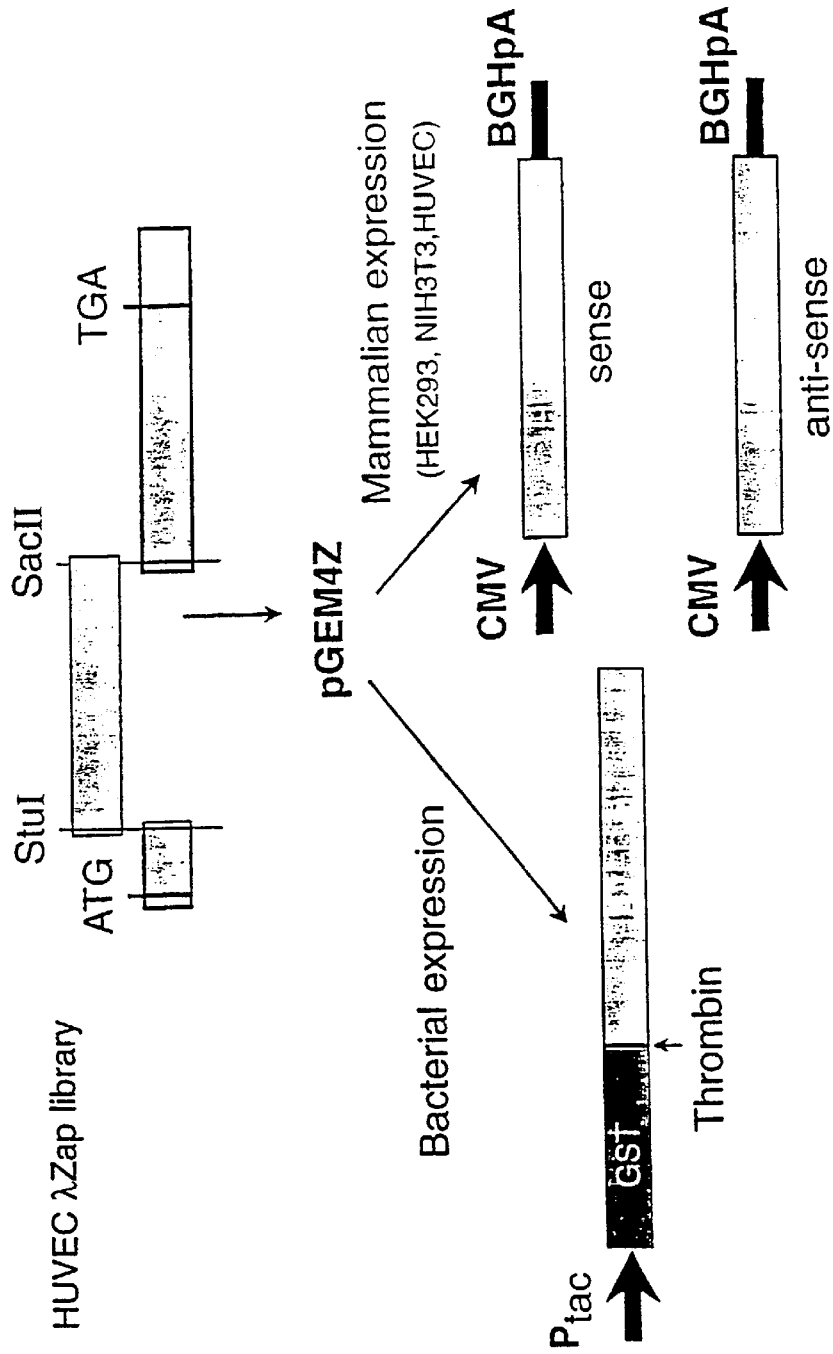
FIG. 6 is a schematic representation of the strategy used to clone sphingosine kinase (SPHK) from HUVEC.

Cloning of Human Sphingosine Kinase and Transient Expression in HEK293 Cells—Results A human sphingosine kinase cDNA was generated from a HUVEC λ Zap library using primers designed from human ESTs aligned with the published murine sphingosine kinase sequence (Kohama et al., 1998). The cloning strategy is shown in FIG. 6 (prov). The cDNA has an apparent open reading frame coding for 384 amino acids (FIG. 7), it should be noted that the sequence lacked a recognisable Kozak consensus motif raising the possibility that the actual initiation sequence may not be included in this cDNA. The sphingosine kinase cDNA encodes for a protein (hSK) with a predicted isoelectric point of 6.64 and a molecular mass of 42,550 kDa, consistent with the molecular mass determined for the purified human placenta sphingosine kinase (SK1). Subcloning into pcDNA3 and transient expression of hSK in HEK293 cells resulted in a 3200-fold increase in sphingosine kinase activity in these cells (FIG. 8), compared with untransfected HEK293 cells or HEK293 cells transfected with empty vector, indicating that the generated hSK cDNA encodes a genuine sphingosine kinase. Interestingly, although hSK-transfected HEK293 cells had 3200-fold higher levels of sphingosine kinase activity, treatment of these cells with TNFα resulted in a rapid (10 min) increase in sphingosine kinase activity by a similar proportion (approximately 2-fold) to that seen in untransfected HEK293 cells (FIG. 8) (Xia et al., 1998). This indicates the high levels of over-expressed sphingosine kinase are not saturating the TNFα mediated activation mechanism in these cells.

EXAMPLE 8

Human Sphingosine Kinase Analysis—Results

A search of the database shown hSK has a high amino acid sequence similarity (28 to 36% identity) to two recently identified Saccharomyces cerevisiae sphirigosine kinases (Nagiec et al., 1998) and several other ESTs encoding putative sphingosine kinase proteins from *Schizosaccharomyces pombe, Caenorhabditis elegans* and *Arabidopis thaliana*. Multiple sequence alignment of hSK with these homologues (FIG. 9) revealed several regions of highly conserved amino acids throuaht the protein, but particularly towards the N-terminus.

Figure 7B:
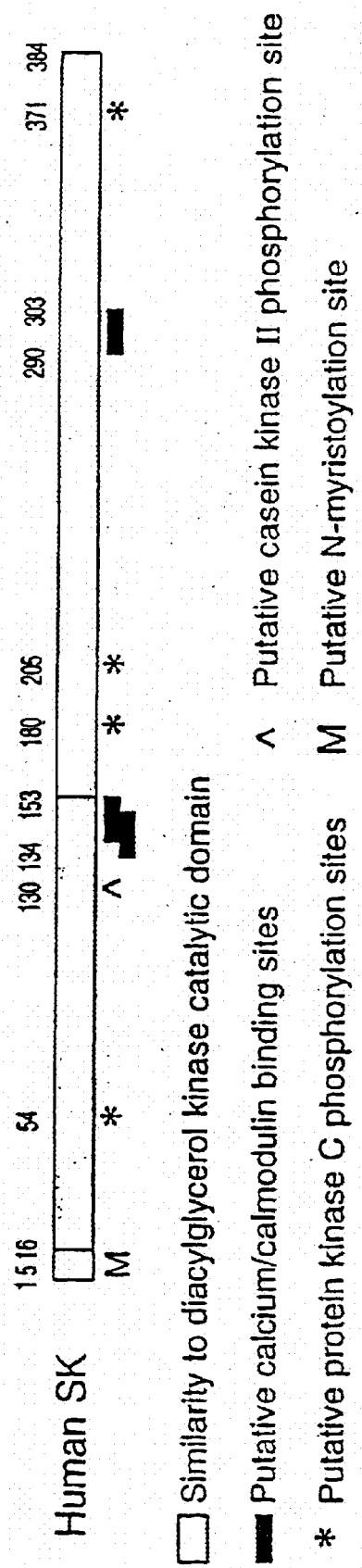
FIG. 7 is a schematic representation of the nucleotide (nucleotides 15-1187 of SEQ ID NO:1) and deduced amino acid (SEQ ID NO:2) sequences and putative domain structure of human sphingosine kinase, a(i)–a(ii), cDNA nucleic acid sequence and the deduced amino acid sequence of hSK. Amino acids are numbered from the first methionine residue. The stop codon is indicated by an asterisk. The sphingosine kinase coding region is in capital letters (nucleotides 33-1187), while lower case letters denote untranslated and vector sequence. b, Schematic representation of human sphingosine kinase showing locations of the putative PKC and CKII phosphorylation sites, a possible N-myristoylation site, calcium/calmodulin binding motifs and the region with similarity to the putative DGK catalytic domain.
Figure 8:
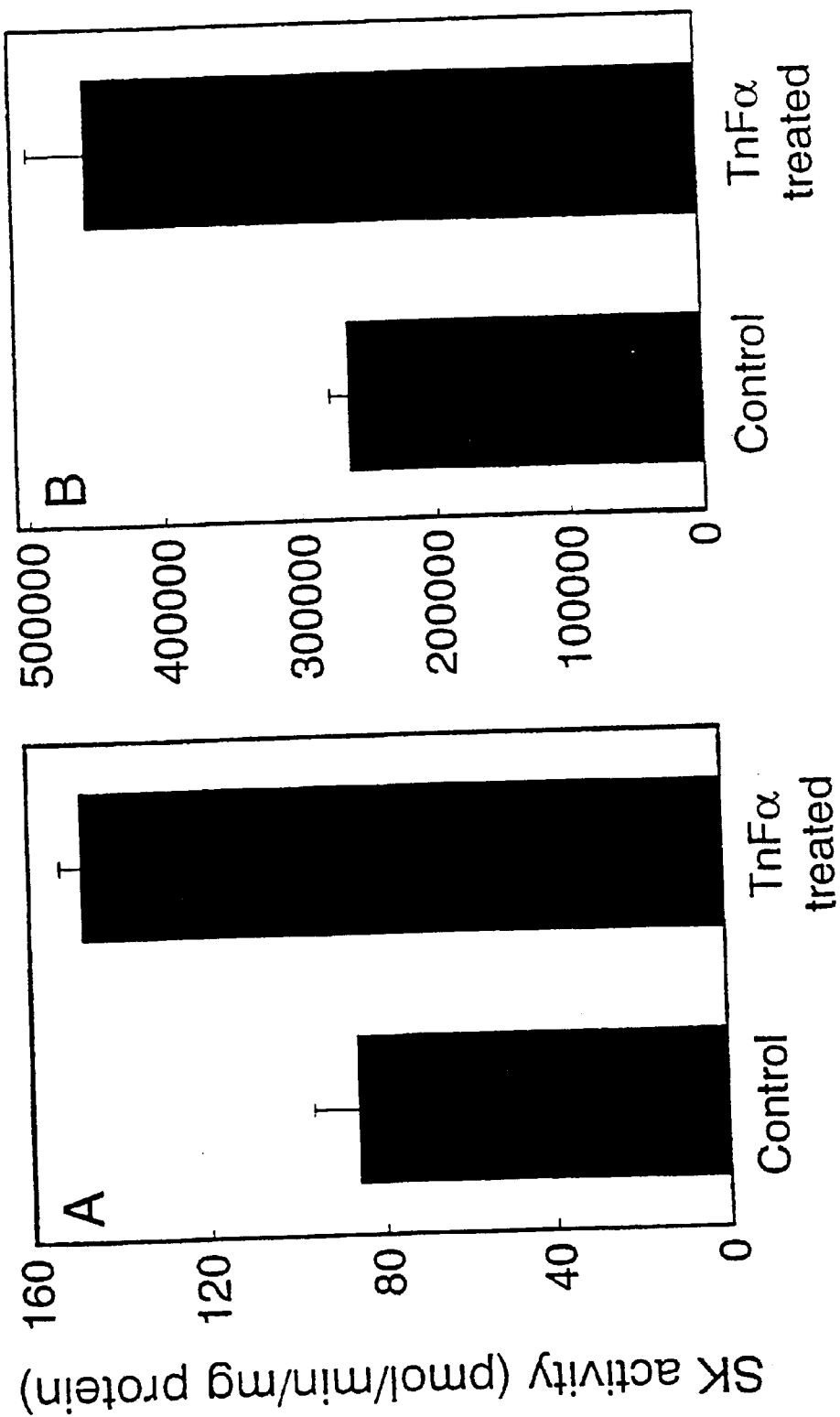
FIG. 8 is a graphical representation of the expression and TNFα stimulation of human sphingosine kinase activity in HEK293 cells. HEK293 cells transiently transfected with either empty pcDNA expression vector alone (A) or pcDNA containing human sphingosine kinase cDNA (B). Transfected cells were either untreated or treated with TNFα for 10 min, harvested and sphingosine kinase activity in cell lysates determined. Data are means of duplicates and are representative of three independent experiments.

A search of the domain structures of hSK sequence revealed three calcium/calmodulin binding motifs (Rhoads & Friedberg, 1997), one of the 1–8 14 type A ([FILVW] xxx{FAILVW]xx[FAILVW]xxxxx{FILVW] (SEQ ID NO:6) with net charge of +3 to +6) spanning residues 290 to 303, and two of the 1–8 14 type B ([FILVW] xxxxx{FAILVW]xxxxx[FILVW] (SEQ ID NO:7) with net charge of +2 to +4) that overlap between residues 134 to 153. Further analysis of the hSK sequence revealed a possible N-myristoylation site close to the N-terminus (at $Gly^5$) that may be applicable if the protein is subject to proteolytic cleavage. Also identified were one putative casein kinase II (CKII) phosphorylation site (at $Ser^{130}$) and four putative PKC phosphorylation sites (at $Thr^{54}$, $Ser^{180}$, $Thr^{205}$ and $Ser^{371}$). (FIG. 7). These putative phosphorylation sites are also found in both murine sphingosine kinase isoforms, although the mouse enzymes also display six more possible phosphorylation sites; four for PKC, and one each for CKII and protein kinase A, that do not occur in hSK.

A search of signalling domain sequences using the SMART search tool (Schultz et al., 1998; Ponting et al., 1999) revealed similarity in residues 16 to 153 of hSK to the putative diacylglycerol kinase (DGK) catalytic domain. hSK showed an overall 36% identity to the consensus sequence of the DGK catalytic domain family, and possessed 17 of the 24 very highly conserved amino acids of this domain. hSK, however, showed no homology with the proposed ATP binding motif of this domain (GxGxxGX$_n$K) (SEQ ID NO:8), although it should be noted that the applicability of this protein kinase ATP-binding site motif (Hanks et al., 1988) to DGKs remains contentious (Schaap et al., 1994); Sakane et al., 1996; Masai et al., 1993). Further sequence analysis of the human sphingosine kinases also failed to find regions showing any marked similarity to the proposed nucleotide-binding motifs found in other protein families (Saraste et al., 1990; Walker et al., 1982). Apart from the similarity to the DGK catalytic domain, hSK shows no similarity to other lipid binding enzymes, and does not appear to have any recognizable lipid binding domains, like PKC C2 or pleckstrin homology domains. There are also no other obvious regulatory domains, with the possible exception of a proline-rich region at the C-terminus which has some similarity to SH3 binding domains (Ren et al., 1993; Yu et al., 1994).

EXAMPLE 9

Expression in *E. Coli* and Isolation of Recombinant Sphingosine Kinase—Results

Figure 10A:
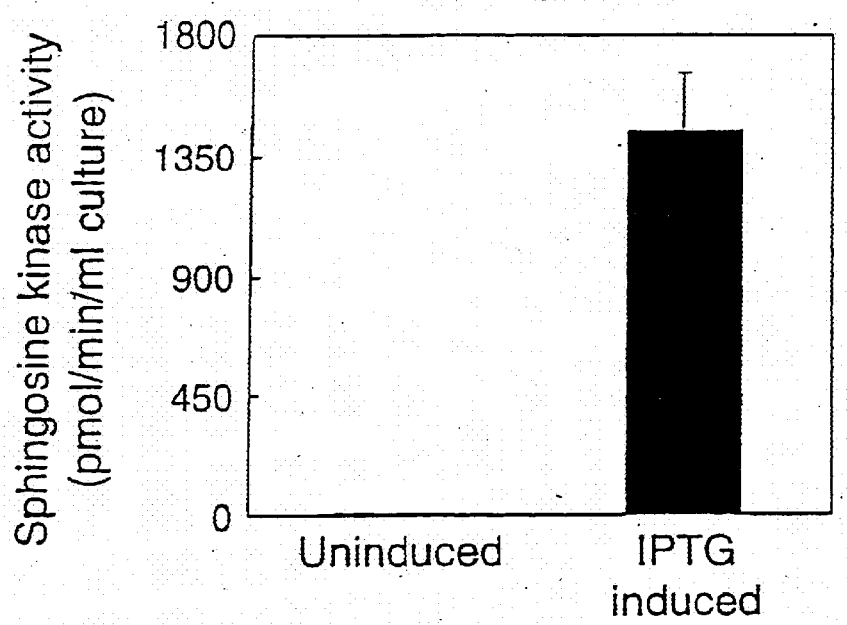
FIG. 10 is an image of the expression of recombinant human sphingosine kinase in *E. coli* BL21. *E. coli* BL21 was transformed with the pGEX4-2T human sphingosine kinase expression construct and expression of the GST-SK fusion protein analysed after induction with 100 μM IPTG. A, Sphingosine kinase activity in uninduced and IPTG induced *E. coli* BL21 cell extracts. B, Coomassie stained SDS-PAGE gel showing GST-SK fusion protein expression in *E. coli* cell lysates. C, Purity of the isolated recombinant human sphingosine kinase. The fraction from the Mono-Q column containing sphingosine kinase activity was applied to SDS-PAGE with silver staining yielding a single band of 45 kDa.
Figure 10B:
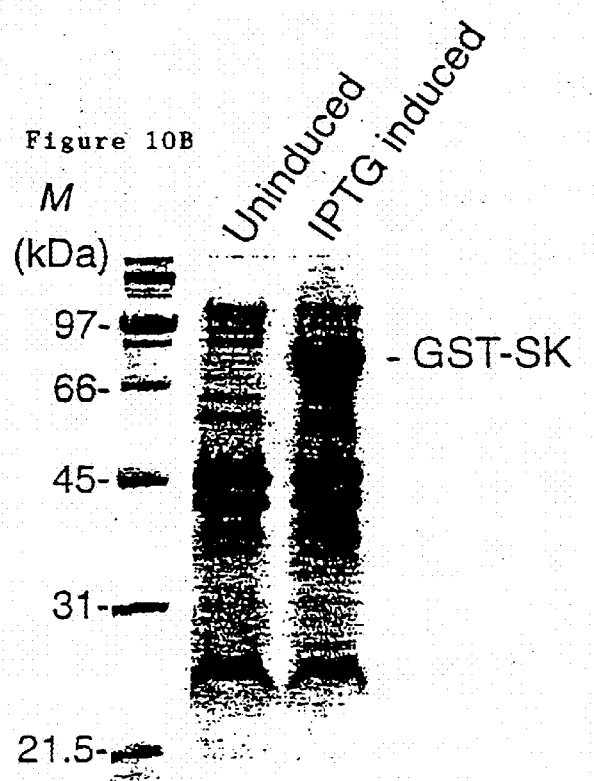
Figure 10C:
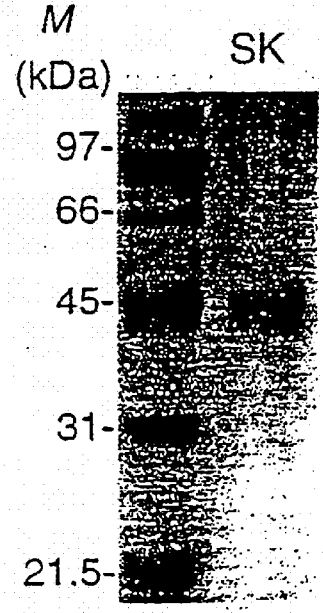
Figure 11:
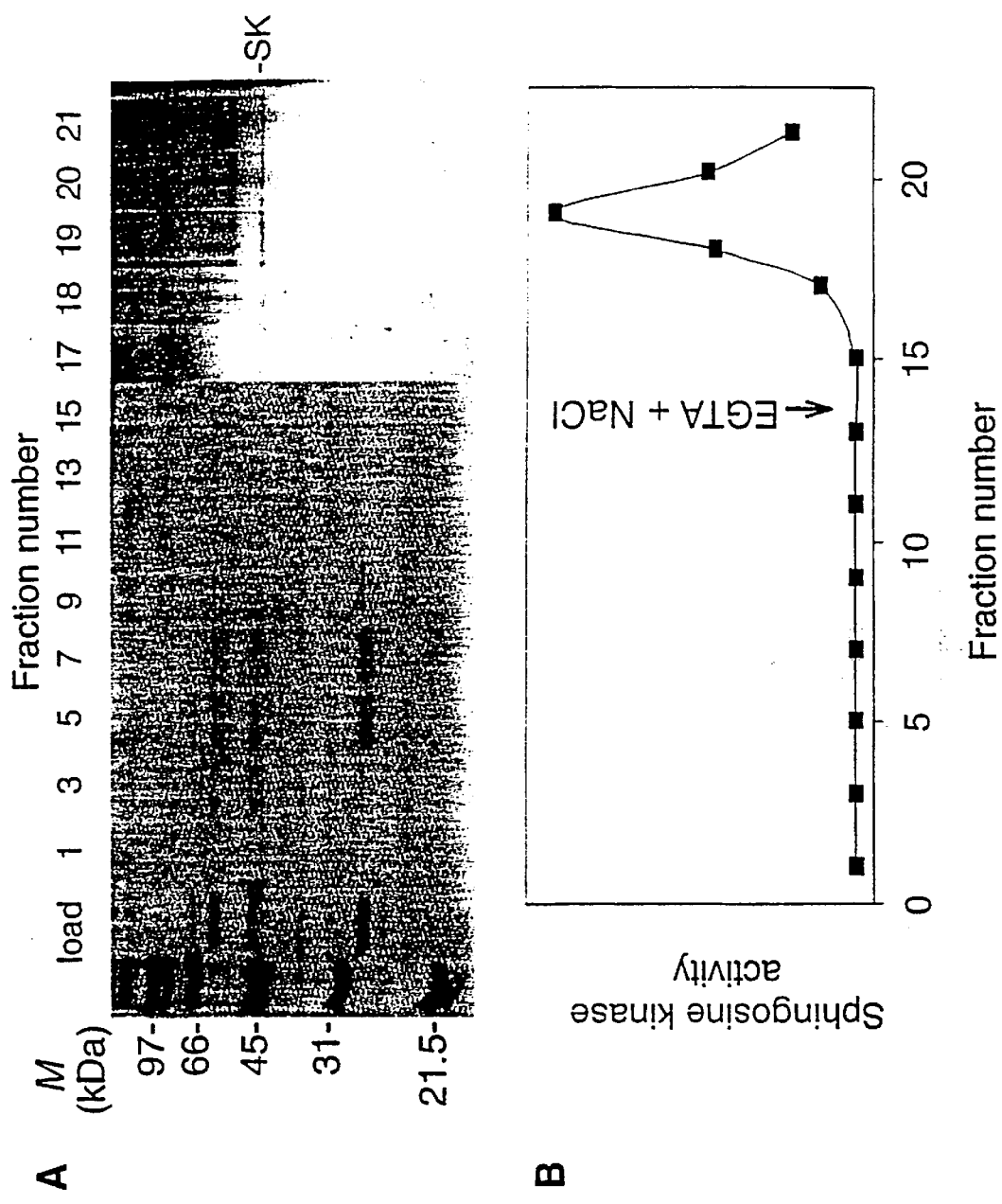
FIG. 11 is an image of the purification of recombinant human sphingosine kinase. Calmodulin Sepharose 4B allows the separation of active and inactive enzyme. The GST-SK fusion protein was partially purified using glutathione-Sepharose 4B, cleaved by thrombin and applied to the calmodulin-Sepharose 4B column in Buffer B containing 4 mM $CaCl_2$. Elution (1) of the active sphingosine kinase bound to the column was performed with Buffer A containing 2 mM EGTA and 1 M NaCl. A, SDS-PAGE analysis of fractions eluted from the calmodulin-Sepharose 4B column. B, Sphingosine kinase activity (|) in column fractions showing most of the recombinant human sphingosine kinase protein did not bind to the column and displayed no catalytic activity.

The hSK cDNA was subcloned into the pGEX 4T-2 plasmid and hSK expressed as a glutathione s-transferase (GST) fusion protein in *E. coli* BL21 by IPTG induction (FIG. 10). After the GST-hSK fusion protein was partially purified using glutathione Sepharose 4B, and the GST removed by thrombin cleavage, the hSK was further purified by subsequent elutions from calmodulin Sepharose and Mono-Q anion exchange columns. This resulted in high recovery of sphingosine kinase activity (greater than 70% of the originally induced activity), and an electrophoretically pure sphingosine kinase (FIG. 10). However, only low protein yields of the recombinant enzyme could be obtained since a large proportion of the IPTG induced, thrombin-cleaved hSK protein did not bind to the calmodulin Sepharose column (FIG. 11). This non-binding form of hSK had no demonstrable catalytic activity, suggesting that it was incorrectly folded.

EXAMPLE 10

Post-translational Modification Requirement for Sphingosine Kinase Fuctional Activity To determine if post-translational modifications are required for activity of the native sphingosine kinase, the native molecule has been compared to the recombinant enzyme produced in *E. coli* where such modifications would not occur. Specifically, the enzymes have been examined for differences in substrate affinity and accessibility. The premise for this study was that post-translational modifications may cause conformational changes in the structure of sphingosine kinase which may result in detectable changes in the physico-chemical or catalytic properties of the enzyme. In summary, it was determined that recombinantly produced sphingosine kinase retains its functional activity even in the absence of post-translational modification.

METHODS

Substrate Specificity of the Native and Recombinant Sphingosinie Kiniases

Relative rates of phosphorylation of sphingosine by the native and recombinant sphingosine kinases were arbitrarily set at 100% and correspond to 2.65 kU and 7.43 kU of the native and recombinant sphingosine kinases, respective. The substrates examined were added to a final concentration of 100 $\mu$M in 0.25% (w/v) Triton X-100, and assayed under the standard assay conditions outlined earlier.

Substrate and Inhibitor Kinetics of the Native and Recombinant Sphingosine Kinases Substrate kinetics were determined by supplying substrates over the concentration range of 0.5 to 200 $\mu$M for sphingosine analogues, and 5 to 1000 $\mu$M for ATP. Inhibition kinetics were determined by the use of inhibitors over a concentration range of 2 to 50 $\mu$M (Table 5). In both cases the data were analysed by non-linear regression.

Thermal Stabilities of the Native and Recombinant Sphingosine Kinases

Thermal stabilities of the native and recombinant sphingosine kinases were determined by assaying the residual activity remaining after preincubation of the enzymes at various temperatures (4 to 80° C.) for 30 min at pH 7.4 (50 mM Tris/HCl containing 10% glycerol, 0.5M NaCl and 0.05% Triton X-100). The original activities of the native and recombinant sphingosine kinases were arbitrarily set at 100% and correspond to 2.65 kU and 7.43 kU, respectively.

pH Stabilities of the Native and Recombinant Sphingosine Kinases pH stabilities of the native and recombinant sphingosine kinases were determined by assaying the residual activity remaining after preincubation of the enzymes at various pH's at 4° C. for 5 hr. The original activities of the native and recombinant sphingosine kinases were arbitrarily set at 100% and correspond to 2.65 kU and 7.43 kU, respectively.

The Effect of pH on Activity of the Native and Recombiant Sphingosine Kinases

The effect of pH on the activity of the native and recombinant sphingosine kinases were determined by assaying the activity over the pH range of 4 to 1 in 50 mM buffers (sodium acetate, pH 4.0–5.0; Mes, pH 6.0–7.0; Hepes, pH 7.0–8.2; Tris, pH 8.2–10.0; Caps. pH 10.0–11.0). The maximum activities of the native and recombinant sphingosine kinases were arbitrarily set at 100% and correspond to 2.65 kU and 7.43 kU, respectively.

Effect of Metal Ions on the Activity of the Native and Recombinant Sphingosine Kinases The effect of metal ions on the activity of the native and recombinant sphingosine kinases were determined by assaying the activity under standard conditions in the presence of various metal ions or EDTA at 10 mM. The maximum activities of the native and recombinant sphingosine kinases were arbitrarily set at 100% and correspond to 2.65 kU and 7.43 kU, respectively.

Effect of Phospholipids on the Activity of the Native and Recombinant Sphingosine Kinases The effect of various phospolipids on the activity of the native and recombinant sphingosine kinases were determined by assaying the activity under standard conditions in the presence of these phospholipids at 10 mol% of Triton X-100. The activities of the native and recombinant sphingosine kinases in the absence of phospholipids were arbitrarily set at 100% and correspond to 2.65 kU and 7.43 kU, respectively. PC, phosphatidylcholine; PS phosphatidylserine; PE, phosphatidyldethanolamine; PI, phosphatidylinositol.

RESULTS

Figures 12A, 12B, 12C, 12D:
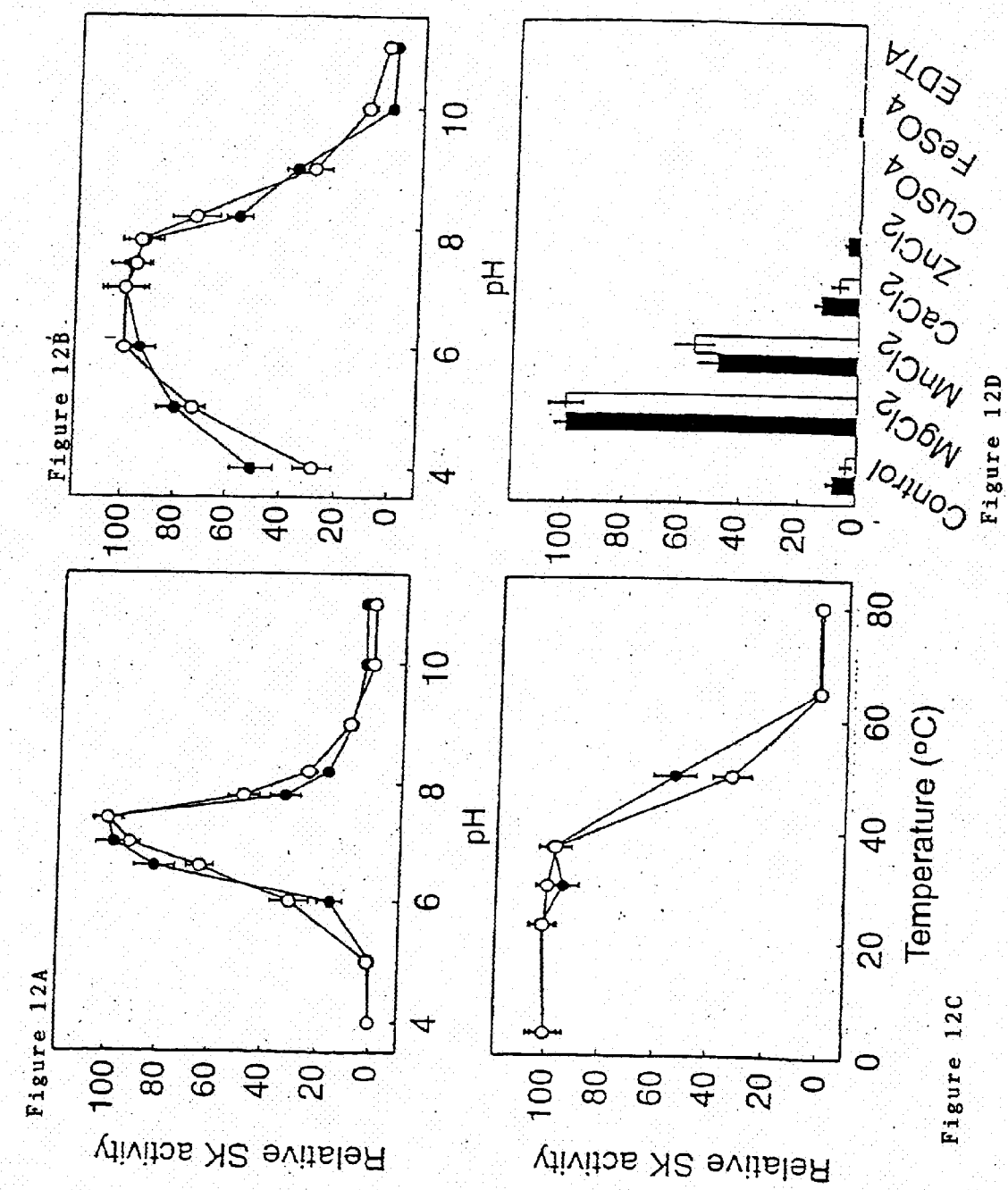
FIG. 12 is a graphical representation of the physicochemical properties of the native and recombinant sphingosine kinases. A, pH optima. The effect of pH on SK activity was determined by assaying the activity over the pH range of 4 to 11 in 50 mM buffers (sodium acetate, pH 4.0–5.0; Mes, pH 6.0–7.0; Hepes, pH 7.0–8.2; Tris/HCl, pH 8.2–10.0; Caps, 10.0–11.0). B, pH stability. Data shown is the SK activity remaining after preincubation of the enzymes at various pH at 4° C. for 5h. C. Temperature stability. Data shown is the SK activity remaining after preincubation of the enzymes at various temperatures (4 to 80° C.) for 30 min at pH 7.4 (50 mM Tris/HCl containing 10% glycerol. 0.5 M NaCl and 0.05% Triton X-100). D, Metal ion requirement. The various metal ions or EDTA were supplied in the assay mixture at a final concentration of 10 mM. In all cases the maximum activities of the native (□ and filled bars) and recombinant (□ and open bars) sphingosine kinases were arbitrarily set at 100% and correspond to 2.65 kU and 7.43 kU, respectively. Data are means ±S.D.

Maximum activity of the native and recombinant sphingosine kinases were observed at pH 7.4, with both enzymes showing greater than 60% of maximum activity in the pH range 6.8 to 7.4 (FIG. 12). Both sphingosine kinases retained more than 90% of the original activity after 5 h incubation at 4° C. in the pH range 6 to 7.8 (FIG. 12), and at pH 7.4 in the presence of 10% glycerol, 0.5M NaCl and 0.05% Triton X-100, both enzymes were stable for 30 min at temperatures up to 37° C. (FIG. 12). The enzymes were much less stable in buffers lacking glycerol. NaCl and Triton X-100 (data not shown), consistent with previous observations of the bovine brain and rat kidney sphingosine kinases (Louie et al., 1976; Olivera et al., 1998). Both human sphingosine kinases showed a requirment for divalent metal ions since the presence of EDTA in assays elimated activity (FIG. 12). Like other sphingosine kinases examined (Louie et al., 1976; Buelirer & Bell. 1992; 1993; Olivera et al., 1998; Nagiec et al., 1998), both human enzymes showed highest activity with $Mg^{2+}$, somewhat lower activity with $Mn^{2-}$, and only very low activity with $Ca^{2+}$. Other divalent metal ions examined, including $ZN^{2-}$, $Cu^{2-}$ and $Fe^{2+}$, did not support sphingosine kinase activity (FIG. 12).

Figures 13A, 13B, 13C:
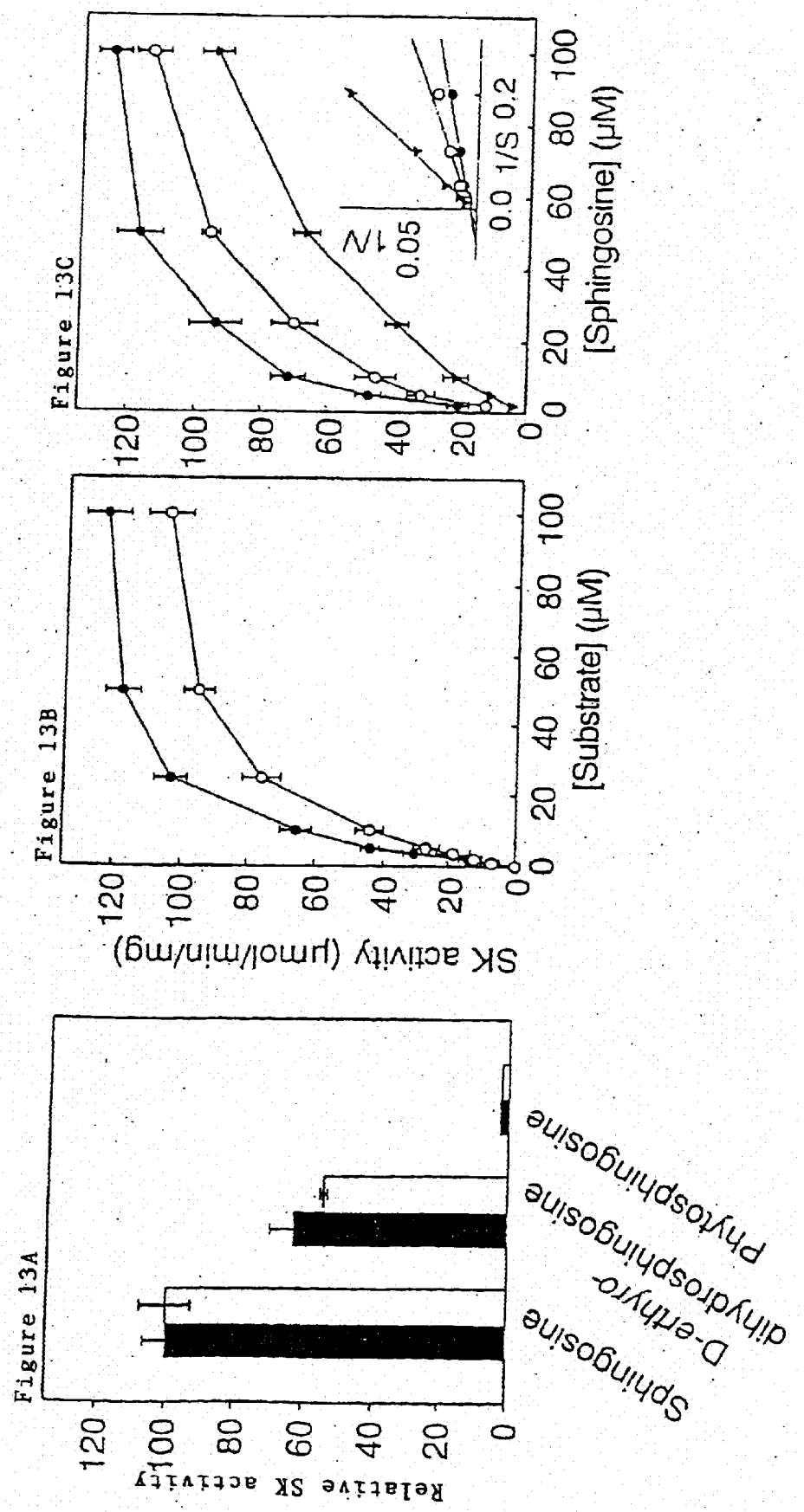
FIG. 13 is a graphical representation of the substrate specificity and kinetics of the native and recombinant sphingosine kinases. A. Substrate specificity of the native (filled bars) and recombinant (open bars) sphingosine kinases with sphingosine analogues and other lipids supplied at 100 µM in 0.25% Triton X-100. The rates of phosphorylation of sphingosine by the native and recombinant Sks were arbitrarily set at 100% and correspond to 2.65 kU and 7.43 kU, respectively. Activity against other potential substrates were expressed relative to the activity against sphingosine. No phosphorylation was observed with DL-threo-dihydrosphingosine, N,N-dimethylsphingosine, N,N,N,-trimethylsphingosinei N-acetylsphingosine ($C_2$-ceramide), diacylglycerol (1,2-dioctanoyl-sn-glycerol and 1,2-dioleoyl-sn-glycerol), and phosphatidylinositol. B, Substrate kinetics of the recombinant human sphingosine kinase with sphingosine (□) and D-erythro-dihydrosphingosine (□) as substrates. C, Kinetics if inhibition of the recombinant human sphingosine kinase with N,N,N-trimethylsphingosine at 5 µM (□) and 25 µM (□), and in the absence of N,N,N-trimethylsphingosine (□). Inset: Lineweaver-Burk plot. Data are means ±S.D.

The native and recombinant sphingosine kinases have very similar, and narrow, substrate specificites (FIG. 13), with both showing greatest activity with the naturally occurring mammalian substrate D-erythro-sphingosine as well as D-erhthro-dihydrosphingosine. Low activity was also detected for both enzymes against phytosphingosine, while a range of other sphingosine derivatives and related molecules where not phosphorylated. These included DL-threo-dihydrosphingosine, N,N-dimethylsphingosine, N,N,N-trimethylsphingosine, N-acetylsphingosine ($C_2$-ceramide), diacylglycerol (1,2-dioctanoyl-sn-glycerol and 1,2-dioleoyl-sn-glycerol), and phosphatidylinositol. Further analysis of the human sphingosine kinases with D-erythro-sphingosine as well as D-erhthro-dihydrosphingosine revealed Michaelis-Menten kinetics over the concentration range used (FIG. 13), with both isolated native and recombinant sphingosine kinases showing very similar kinetic properties and slightly higher affinity for D-erythro-sphingosine as well as D-erhthro-dihydrosphingosine (Table 5). Both enzymes also displayed similar kinetics when sphingosine was supplied as a sphingosine-BSA complex, although presentation of the substrate in this manner resulted in a lower $k_{cat}$ values for both enzymes (28 $s^{-1}$ and 39 $s^{-1}$ for the native and recombinant sphingosine kinases, respectively) compared to its presentation in Triton X-100 mixed micelles, as used for all the other assays performed in this study. Sphingosine supplied as a BSA complex $K_m$ values of 16±4 mM and 17±2 mM for the native and recombinant sphingosine kinases, respectively. Both the native and recombinant sphingosine kinases had the same affinity for ATP ($K_m$ of approx. 80 mM (Table 5).

Both the native and recombinant sphinqosine kinase were inhibited by DL-threo-dihydrosplhingosine, N,N-dimethylsphingosine and N,N,N-trimethylsphingosine (FIG. 13). with all three of these molecules displaying competitive inhibition with respect to sphingosine. Although the inhibition constants for these molecules were quite similar, N,N,N-trimethylsphingosine gave slightly more efficient inhibition than DL-threo-dihydrosphingosine, which was a marginally more efficient inhibitor than N,N-dimethylsphingosine (Table 5).

ADP also showed weak competitive inhibition, with respect to ATP (Table 5). In all cases remarkably similar inhibition constants were observed for the native and recombinant sphingosine kinases (Table 5). No inhibition was seen with N-acetylsphingosine or Fumosin B1, a ceramide synthase inhibitor.

The effect of calcium/calmodulin on sphingosine kinase activity was examined. Under the assay conditions used, calcium/calmodulin had no effect on the activity of either the native or recombinant human sphingosine kinases (data not shown). While this result indicates a lack of sphingosine kinase activity regulation by calmodulin, the possibility remains that calmodulin may be involved in some other function with sphingosine kinase, such as regulating ists subcellular localisation.

Figure 14:
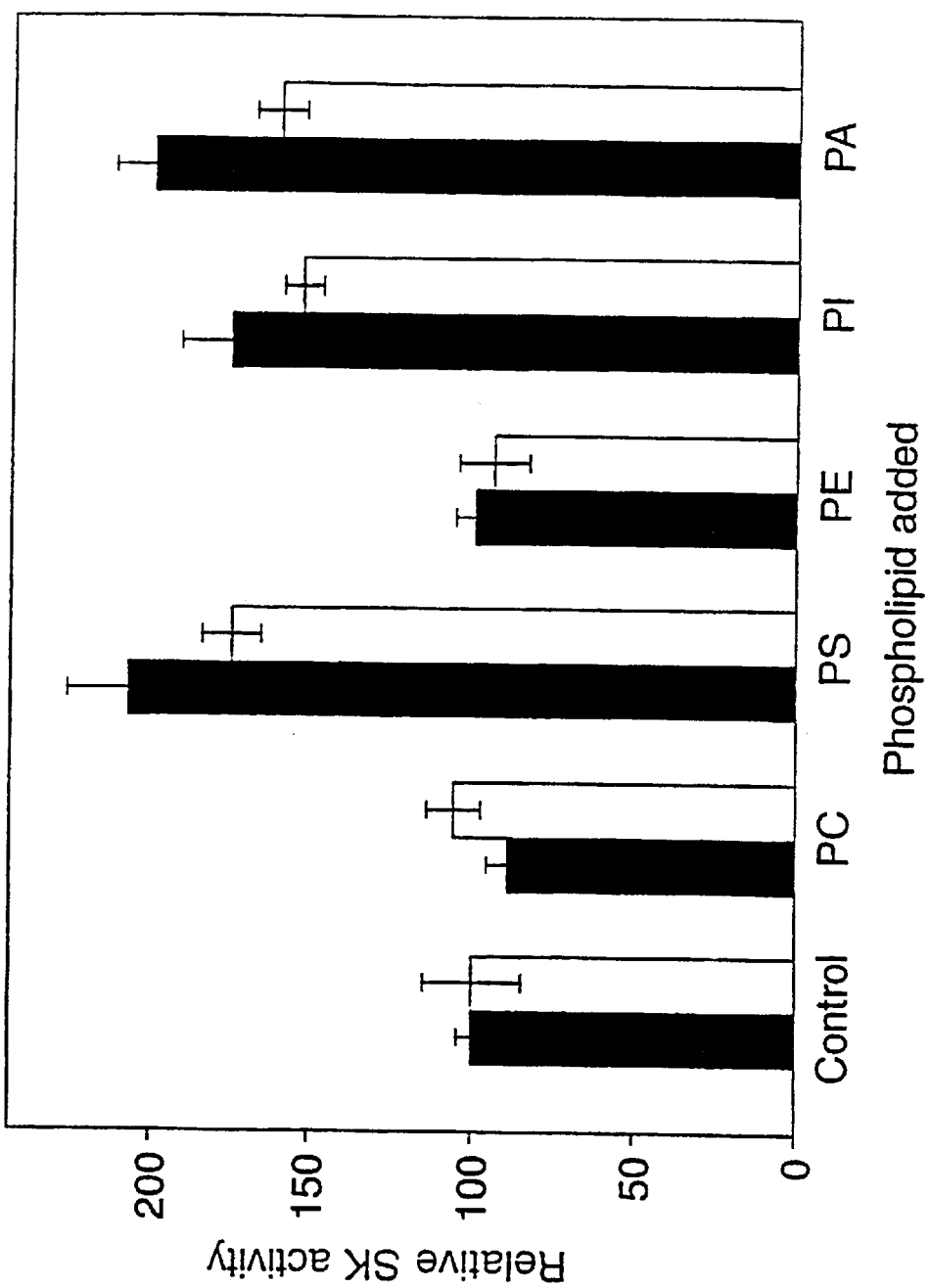
FIG. 14 is a graphical representation of the acidic phospholipids which stimulate the activity of the native and recombinant sphingosine kinases. The effect of various phospholipids on the activity of the native and recombinant sphingosine kinases were determined by assaying the activity under standard conditions in the presence if these phospholipids at 10 mol% of Triton X-100. The activities of the native (filled bars) and recombinant (open bars) sphingosine kinases in the absence of phospholipids were arbitrarily set at 100% and correspond to 2.65 kU and 7.43 kU, respectively. PC, phosphatidylcholine; PS, phosphatidyiserine; PE, phosphatidylethanolamine: PI phosphatidylinositol; PA, phosphatidic acid. Data are means=S.D.

Stimulation of sphingosine kinase activity by acidic phospholipids was examined. The addition of the neutral phospholipids phosphatidylcholine and phosphatidyldethanolamine to the enzyme assay mixture did not result in any detectable differences in human sphingosine kinase activity, however, marked increases in activity (1.6 to 2-fold) were observed with the acidic phospholipids phosphatidylserine, phosphatidylinositol and phosphatidic acid (FIG. 14). Both the native and recombinant sphingosine kinases were activated in a similar manner by these acidic phospholipids, with kinetic analyses revealing that all three phospholipids caused an increase in the enzymes $K_{cat}$, while the $K_m$ values remained unchanged.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 3

Comparison of sphingosine kinase activity in human placenta with various animal tissues Fresh animal tissues were washed and homogenized as described for the human placenta. The proportion of cytosolic sphingosine kinase activity was determined by comparison of the total activity in the homogenate to that from the ultracentrifugation supernatant (100,000 × g. 60 min). The specific activity of sphingosine kinase is expressed as pmol of SIP formed per minute (U) per g tissue.

|  | Specific activity (U/g tissue) | Cytosolic (%) |
| --- | --- | --- |
| Human placenta | 13 | 51 |
| Rat kidney | 28 | 63 |
| Rat liver | 19 | 37 |
| Rat brain | 13 | 52 |
| Sheep kidney | 38 | 58 |
| Sheep liver | 17 | 31 |
| Sheep brain | 16 | 63 |
| Sheep spleen | 9 | 34 |

TABLE 4

Purification of sphingosine kinase from human placenta
Sphingosine kinase was purified from 1240 g of fresh human placenta (4 placentas). One unit (U) of sphingosine kinase activity is defined as 1 pmol of SIP formed from sphingosine and ATP per minute.

| Step | Activity (U × 10³) | Protein (mg) | Specific Activity (U/mg) | Recovery (%) | Purification Fold |
|---|---|---|---|---|---|
| Soluble fraction of homogenate | 7943 | 123600 | 58 | 100 | |
| Ammonium sulphate (25–35%) | 7723 | 3527 | 1966 | 97 | 33 |
| Q Sepharose anion exchange | 4048 | 1098 | 4597 | 63 | 79 |
| Calmodulin Sepharose | 3197 | 18.23 | $1.75 \times 10^5$ | 40 | $3.0 \times 10^3$ |
| Mono Q anion exchange | 1706 | 2.921 | $5.84 \times 10^5$ | 21.5 | $1.0 \times 10^4$ |
| ATP-Mono Q anion exchange | 1133 | 0.419 | $2.70 \times 10^6$ | 14.3 | $4.6 \times 10^4$ |
| Superdex 75 gel filtration | 549 | 0.008 | $6.64 \times 10^7$ | 6.9 | $1.1 \times 10^6$ |

TABLE 5

Substrate and inhibition kinetics of the native and recombinant sphingosine kinases
Substrate kinetics were determined by supplying substrates over the concentration range of 0.5 to 200 $\mu$M (0.0125 to 5 mol %) for sphingosine analogues. and 5 to 1000 $\mu$M for ATP. Inhibition kinetics were determined by the use of inhibitors over a concentration range of 2 to 50 $\mu$M (0.05 to 1.25 mol %) for sphingosine analogues and 0.1 to 5 mM for ADP. For comparison to previous studies, all $K_m$ and $K_i$ values for sphingosine and its derivatives are expressed as both bulk solution concentrations and mol % of Triton X-100, where Triton X-100 was present in all assays at a final concentration of 0.25% (w/v). All kinetic values and standard errors (Duggleby, 1981) were obtained from non-linear regression analysis (Easterby, 1996).

| | Native SK | Recombinant SK |
|---|---|---|
| SUBSTRATE KINETICS: | | |
| Sphingosine | | |
| $K_m$ (mol %) | 0.35 ± 0.05 | 0.30 ± 0.07 |
| $K_m$ ($\mu$M) | 14 ± 2 | 12 ± 3 |
| $k_{cat}$ (S$^{-1}$) | 50 | 85 |
| $k_{cat}/K_m$ (10$^{-5}$ s$^{-1}$ · M$^{-1}$) | 36 | 71 |
| Dihydrosphingosine | | |
| $K_m$ (mol %) | 0.50 ± 0.05 | 0.48 ± 0.05 |
| $K_m$ ($\mu$M) | 20 ± 2 | 19 ± 2 |
| $k_{cat}$ (S$^{-1}$) | 35 | 76 |
| $k_{cat}/K_m$ (10$^{-5}$ s$^{-1}$ · M$^{-1}$) | 18 | 39 |
| ATP | | |
| $K_m$ ($\mu$M) | 77 ± 11 | 86 ± 12 |
| INHIBITOR KINETICS: | | |
| N,N-dimethylsphingosine | | |
| $K_i$ (mol %) | 0.20 ± 0.03 | 0.19 ± 0.02 |
| $K_i$ ($\mu$M) | 7.8 ± 1 | 7.5 ± 1 |
| DL-threo-dihydrosphingosine | | |
| $K_i$ (mol %) | 0.15 ± 0.02 | 0.14 ± 0.03 |
| $K_i$ ($\mu$M) | 5.9 ± 1 | 5.7 ± 1 |
| N,N,N-trimethylsphingosine | | |
| $K_i$ (mol %) | 0.12 ± 0.03 | 0.10 ± 0.02 |
| $K_i$ ($\mu$M) | 4.6 ± 1 | 3.8 ± 1 |
| ADP | | |
| $K_i$ (mM) | 1.1 ± 0.3 | 0.9 ± 0.2 |

BIBLIOGRAPHY

Altschul, S. F., Gish. W., Miller, W., Meyer, E. W., and Lipman, D. J., (1990) *J. Mol. Biol.* 215:403–410

Alessenko, A. V., (1998) *Biochermistry* 63:62–68

Bonner et al., (1973) *J. Mol. Biol.* 81:123

Bradford, M. M., (1976) *Anal. Biochem.* 72:248–254

Buehrer, B. M., and Bell, R. M., (1992) *J. Biol Chem.* 267:3154–3159

Buefhrer, B. M., and Bell, R. M., (1993) *Adv. Lipid Res.* 26:59–67

Buehrer, B. M., Bardes, E. S., and Bell. R. M., (1996) *Biochimn. Biophys. Acta* 1303:233–242

Culliver, O., Pirianov, G., Kleuser. B., Vanek, P. G., Coso, O. A., Gutkind, J. S., and Spiegel, S., (1996) *Nature* 381:800–803

Douillard and Hoffman, Basic facts about hybridomas in Compendium of Immunology, Vol II ed. Schwartz (1981)

Duggleby, R. G., (1981) *Anal Biochem.* 110:9–18

Easterby, J. S., (1996) Hyper 1.1s: Hyperbolic Regression Analysis of Enzyme Kinetic Data. Liverpool University, Liverpool Graham, F. L., and van der Eb, A. J. (1973) *Virology* 54:536–539

Hanks, S. K., Quinn, A. M., and Hunter, T., (1988) *Science* 241:42–52

Igarashi. Y., (1997) *J. Biochem.* 122:1080–1087

Kohama. T., Olivera, A., Edsall. L., Naiec. M. M., Dickson. R. and Spiegel, S., (1998) *J Biol. Chem.* 273:23722–23728

Kohler and Milstein., (1975) *Nature* 256:495–499

Laemmli, U. K., (1970) *Nature* 227:680–685

Louie, D. D., Kisic. A., and Schroepfer. G. J., (1976) *J. Biol. Chem.* 251:4557–4564

Masai, I., Okazaki, A., Hosoya, T., and Hotta, Y., (1993) *Proc. Natl. Acad. Sci. USA* 90:11157–11161

Melendez, A., Floto, R. A., Gillooly, D. J., Hamett, M. M. and Allen, J. M., (1998) *J. Biol Chem.* 273:9393–9402

Meyer zu Heringdorf, D., van Koppen. C. J. and Jakobs, K. H., (1997) *FEBS Lett* 410:34–38

Nagiec, M. M., Skrzypek, M., Nagiec, E. E., Lester, R. L., and Dickson, R. C., (1998) *J Biol. Chem.* 273:19437–19442

Olivera, A. and Spiegel, S., (1993) *Nature* 365:557–560

Olivera, A., Kohama, T., Tu, Z., Milstein, S., and Spiegel, S., (1998) *J Biol. Chem.* 273:12576–12583

Ponting, C. P., Schultz, J., Milpetz., and Bork, P., (1999) *Nucleic Acids Res.* 27:229–232

Ren, R., Mayer, B. J., Cicchetti, P., and Baltimore, D., (1993) *Science* 259:1157–1161

Rhoads. A. R., and Friedberg. F., (1997) *FASEB J.* 11:331–340

Sakane. F., Lai. M., Wada I., Imai. S., and Kohoh. H., (1996) *Biochem J.* 318:583–590

Saraste, M., Sibbald, P. R. and Wittinghofer, A., (1990) *Trentds Biochem. Sci.* 15:430–434

Schaap, D., van der Wal, J., and van Blitterswijk, W., (1994) *Biochem. J.* 304:661–662

Schultz, J., Milpetz, F., Bork, P., and Ponting. C. P., (1998) *Proc. Natl, Acad. Sci. USA* 95:5857–5864

Smith, P. K., Krohn, R. I., Hermanson. G. T., Mallia, A. K., Gartner, F. H., Provenzano, M.D., Fujimoto, E. K., Goeke, N. M., Olson. B. J., and Kienk, D. C., (1985) *Anal. Biochem.* 150:76–85

Spiegel, S., Culliver, O., Edsall, L., Kohama, T. Menzeleev, R., Olivera, A., Thomas, D., Tu, Z., Van Brooklyn, J. and Wang, F., (1998). *Biochemistry (Mosc)* 63:69–73

Walker, J. E., Saraste, M., Runswick. M. J., and Gray, N. J., (1982) *EMBO J.* 8:945–951

Wall, R. T., Harker, L. A., Quadracci. L. J., and Striker. G. E., (1978) *J. Cell. Physiol.* 96:203–213

Wessel, D., and Flugge, U. I., (1984) *Anal. Biochemn.* 138:141–143

Xia, P., Gamble, J. R., Rye, K.-A., Wang, L., Hii. C. S. T., Cockerill, P., Khew-Goodall, Y., Bert, A. G., Barter, P. J., and Vadas, M. A., (1998) *Proc. Natl Acad. Sci. USA* 95:14196–14201

Yu, H., Chen, J. K., Feng, S., Dalgamo, D. C., Brauer, A. W., and Schreiber, S. L., (1994) *Cell* 76:933–945

---

The claims defining the invention are as follows:

1. An isolated polynucleotide encoding a sphingosine kinase, the polyinucleotide comprising (1) the sequence of SEQ ID NO:1, (2) a sequence at least 90% identical to SEQ ID NO:1, (3) a nucleotide sequence that hybridizes to the nucleotide sequence of (1) or (2) under high stringency conditions of about 65° C. and about 50% v/v formamide and about 0.15M salt, (4) a nucleotide sequence encoding a polypeptide having the sequence of SEQ ID NO:2, or (5) a nucleotide sequence complementary to the nucleotide sequence of any one of (1) to (4).

2. An isolated polynucleotide according to claim 1, the polynucleotide comprising a sequence at least 95% identical to SEQ ID NO:1.

3. An isolated polynucleotide sequence that hybridizes to the nucleotide sequence of claim 2 stringency conditions of about 65° C. and about 50% v/v formamide and about 0.15M salt.

4. An isolated polynucleotide according to claim 1, the polynucleotide encoding a polypeptide having the sequence of SEQ ID NO:2.

5. An isolated polynucleotide according to claim 1, the polynucleotide comprising the sequence of SEQ ID NO:1.

6. An expression system comprising a polynucleotide according to claim 1.

7. An expression system according to claim 6 capable of producing a sphingosine kinase comprising the polypeptide sequence of SEQ ID NO:2 when the expression system is in a compatible host cell.

8. A recombinant host cell, the host cell comprising the expression system according to claim 7.

9. A method of modulating expression of sphingosine kinase, in a subject, said method comprising contacting the sphingosine kinase encoding gene with an effective amount of an agent for a time and under conditions sufficient to modulate expression of sphingosine kinase, said agent comprising an isolated polynucleotide according to claim 1.

* * * * *

SEQUENCE LISTING

```
<160> NUMBER OF SEQ ID NOS: 56

<210> SEQ ID NO 1
<211> LENGTH: 1205
<212> TYPE: DNA
<213> ORGANISM: Homo sapiens
<220> FEATURE:
<221> NAME/KEY: CDS
<222> LOCATION: (33)..(1184)
<223> OTHER INFORMATION:

<400> SEQUENCE: 1
gaattcggca cgaggagccg cgggtcgagg tt atg gat cca gcg ggc ggc ccc         53
                                    Met Asp Pro Ala Gly Gly Pro
                                     1               5 cgg ggc gtg ctc ccg cgg ccc tgc cgc gtg ctg gtg ctg ctg aac ccg        101
Arg Gly Val Leu Pro Arg Pro Cys Arg Val Leu Val Leu Leu Asn Pro
         10                  15                  20 cgc ggc ggc aag ggc aag gcc ttg cag ctc ttc cgg agt cac gtg cag        149
Arg Gly Gly Lys Gly Lys Ala Leu Gln Leu Phe Arg Ser His Val Gln
     25                  30                  35 ccc ctt ttg gct gag gct gaa atc tcc ttc acg ctg atg ctc act gag        197
Pro Leu Leu Ala Glu Ala Glu Ile Ser Phe Thr Leu Met Leu Thr Glu
 40                  45                  50                  55 cgg cgg aac cac gcg cgg gag ctg gtg cgg tcg gag gag ctg ggc cgc        245
Arg Arg Asn His Ala Arg Glu Leu Val Arg Ser Glu Glu Leu Gly Arg
                 60                  65                  70 tgg gac gct ctg gtg gtc atg tct gga gac ggg ctg atg cac gag gtg        293
Trp Asp Ala Leu Val Val Met Ser Gly Asp Gly Leu Met His Glu Val
             75                  80                  85 gtg aac ggg ctc atg gag cgg cct gac tgg gag acc gcc atc cag aag        341
Val Asn Gly Leu Met Glu Arg Pro Asp Trp Glu Thr Ala Ile Gln Lys
         90                  95                 100 ccc ctg tgt agc ctc cca gca ggc tct ggc aac gcg ctg gca gct tcc        389
Pro Leu Cys Ser Leu Pro Ala Gly Ser Gly Asn Ala Leu Ala Ala Ser
        105                 110                 115 ttg aac cat tat gct ggc tat gag cag gtc acc aat gaa gac ctc ctg        437
Leu Asn His Tyr Ala Gly Tyr Glu Gln Val Thr Asn Glu Asp Leu Leu
120                 125                 130                 135 acc aac tgc acg cta ttg ctg tgc cgc cgg ctg ctg tca ccc atg aac        485
Thr Asn Cys Thr Leu Leu Leu Cys Arg Arg Leu Leu Ser Pro Met Asn
                140                 145                 150 ctg ctg tct ctg cac acg gct tcg ggg ctg cgc ctc ttc tct gtg ctc        533
Leu Leu Ser Leu His Thr Ala Ser Gly Leu Arg Leu Phe Ser Val Leu
            155                 160                 165 agc ctg gcc tgg ggc ttc att gct gat gtg gac cta gag agt gag aag        581
Ser Leu Ala Trp Gly Phe Ile Ala Asp Val Asp Leu Glu Ser Glu Lys
        170                 175                 180
```

-continued

| | |
|---|---|
| tat cgg cgt ctg ggg gag atg cgc ttc act ctg ggc act ttc ctg cgt<br>Tyr Arg Arg Leu Gly Glu Met Arg Phe Thr Leu Gly Thr Phe Leu Arg<br>185                             190                           195 | 629 |
| ctg gca gcc ttg cgc act tac cgc ggc cga ctg gct tac ctc cct gta<br>Leu Ala Ala Leu Arg Thr Tyr Arg Gly Arg Leu Ala Tyr Leu Pro Val<br>200                           205                        210                    215 | 677 |
| gga aga gtg ggt tcc aag aca cct gcc tcc ccc gtt gtg gtc cag cag<br>Gly Arg Val Gly Ser Lys Thr Pro Ala Ser Pro Val Val Val Gln Gln<br>                   220                        225                       230 | 725 |
| ggc ccg gta gat gca cac ctt gtg cca ctg gag gag cca gtg ccc tct<br>Gly Pro Val Asp Ala His Leu Val Pro Leu Glu Glu Pro Val Pro Ser<br>              235                       240                      245 | 773 |
| cac tgg aca gtg gtg ccc gac gag gac ttt gtg cta gtc ctg gca ctg<br>His Trp Thr Val Val Pro Asp Glu Asp Phe Val Leu Val Leu Ala Leu<br>        250                       255                       260 | 821 |
| ctg cac tcg cac ctg ggc agt gag atg ttt gct gca ccc atg ggc cgc<br>Leu His Ser His Leu Gly Ser Glu Met Phe Ala Ala Pro Met Gly Arg<br>        265                       270                       275 | 869 |
| tgt gca gct ggc gtc atg cat ctg ttc tac gtg cgg gcg gga gtg tct<br>Cys Ala Ala Gly Val Met His Leu Phe Tyr Val Arg Ala Gly Val Ser<br>280                           285                        290                    295 | 917 |
| cgt gcc atg ctg ctg cgc ctc ttc ctg gcc atg gag aag ggc agg cat<br>Arg Ala Met Leu Leu Arg Leu Phe Leu Ala Met Glu Lys Gly Arg His<br>                   300                        305                       310 | 965 |
| atg gag tat gaa tgc ccc tac ttg gta tat gtg ccc gtg gtc gcc ttc<br>Met Glu Tyr Glu Cys Pro Tyr Leu Val Tyr Val Pro Val Val Ala Phe<br>              315                       320                      325 | 1013 |
| cgc ttg gag ccc aag gat ggg aaa ggt atg ttt gca gtg gat ggg gaa<br>Arg Leu Glu Pro Lys Asp Gly Lys Gly Met Phe Ala Val Asp Gly Glu<br>        330                       335                       340 | 1061 |
| ttg atg gtt agc gag gcc gtg cag ggc cag gtg cac cca aac tac ttc<br>Leu Met Val Ser Glu Ala Val Gln Gly Gln Val His Pro Asn Tyr Phe<br>345                           350                        355 | 1109 |
| tgg atg gtc agc ggt tgc gtg gag ccc ccg ccc agc tgg aag ccc cag<br>Trp Met Val Ser Gly Cys Val Glu Pro Pro Pro Ser Trp Lys Pro Gln<br>360                           365                       370                   375 | 1157 |
| cag atg cca ccg cca gaa gag ccc tta tgatctagag tcgacctgca g<br>Gln Met Pro Pro Pro Glu Glu Pro Leu<br>              380 | 1205 |

<210> SEQ ID NO 2
<211> LENGTH: 384
<212> TYPE: PRT
<213> ORGANISM: Homo sapiens

<400> SEQUENCE: 2

Met Asp Pro Ala Gly Gly Pro Arg Gly Val Leu Pro Arg Pro Cys Arg
1                   5                       10                      15

Val Leu Val Leu Leu Asn Pro Arg Gly Gly Lys Gly Lys Ala Leu Gln
                 20                       25                       30

Leu Phe Arg Ser His Val Gln Pro Leu Leu Ala Glu Ala Glu Ile Ser
                       35                       40                       45

Phe Thr Leu Met Leu Thr Glu Arg Arg Asn His Ala Arg Glu Leu Val
        50                       55                       60

Arg Ser Glu Glu Leu Gly Arg Trp Asp Ala Leu Val Val Met Ser Gly
65                   70                       75                       80

Asp Gly Leu Met His Glu Val Val Asn Gly Leu Met Glu Arg Pro Asp
                       85                       90                       95

Trp Glu Thr Ala Ile Gln Lys Pro Leu Cys Ser Leu Pro Ala Gly Ser

```
            100                 105                 110
Gly Asn Ala Leu Ala Ala Ser Leu Asn His Tyr Ala Gly Tyr Glu Gln
            115                 120                 125

Val Thr Asn Glu Asp Leu Leu Thr Asn Cys Thr Leu Leu Cys Arg
    130                 135                 140

Arg Leu Leu Ser Pro Met Asn Leu Leu Ser Leu His Thr Ala Ser Gly
145                 150                 155                 160

Leu Arg Leu Phe Ser Val Leu Ser Leu Ala Trp Gly Phe Ile Ala Asp
                165                 170                 175

Val Asp Leu Glu Ser Glu Lys Tyr Arg Arg Leu Gly Glu Met Arg Phe
                180                 185                 190

Thr Leu Gly Thr Phe Leu Arg Leu Ala Ala Leu Arg Thr Tyr Arg Gly
            195                 200                 205

Arg Leu Ala Tyr Leu Pro Val Gly Arg Val Gly Ser Lys Thr Pro Ala
210                 215                 220

Ser Pro Val Val Gln Gln Gly Pro Val Asp Ala His Leu Val Pro
225                 230                 235                 240

Leu Glu Glu Pro Val Pro Ser His Trp Thr Val Val Pro Asp Glu Asp
                245                 250                 255

Phe Val Leu Val Leu Ala Leu Leu His Ser His Leu Gly Ser Glu Met
                260                 265                 270

Phe Ala Ala Pro Met Gly Arg Cys Ala Ala Gly Val Met His Leu Phe
                275                 280                 285

Tyr Val Arg Ala Gly Val Ser Arg Ala Met Leu Leu Arg Leu Phe Leu
            290                 295                 300

Ala Met Glu Lys Gly Arg His Met Glu Tyr Glu Cys Pro Tyr Leu Val
305                 310                 315                 320

Tyr Val Pro Val Val Ala Phe Arg Leu Glu Pro Lys Asp Gly Lys Gly
                325                 330                 335

Met Phe Ala Val Asp Gly Glu Leu Met Val Ser Glu Ala Val Gln Gly
                340                 345                 350

Gln Val His Pro Asn Tyr Phe Trp Met Val Ser Gly Cys Val Glu Pro
            355                 360                 365

Pro Pro Ser Trp Lys Pro Gln Gln Met Pro Pro Glu Glu Pro Leu
    370                 375                 380

<210> SEQ ID NO 3
<211> LENGTH: 24
<212> TYPE: DNA
<213> ORGANISM: Artificial Sequence
<220> FEATURE:
<223> OTHER INFORMATION: primer

<400> SEQUENCE: 3
cggaattccc agtcggccgc ggta                                          24

<210> SEQ ID NO 4
<211> LENGTH: 26
<212> TYPE: DNA
<213> ORGANISM: Artificial Sequence
<220> FEATURE:
<223> OTHER INFORMATION: primer

<400> SEQUENCE: 4
tagaattcta ccgcggccga ctggct                                        26

<210> SEQ ID NO 5
```

```
<211> LENGTH: 52
<212> TYPE: DNA
<213> ORGANISM: Artificial Sequence
<220> FEATURE:
<223> OTHER INFORMATION: primer

<400> SEQUENCE: 5
tagaattcac ttgtcatcgt cgtccttgta gtctaagggc tcttctggcg gt         52

<210> SEQ ID NO 6
<211> LENGTH: 32
<212> TYPE: PRT
<213> ORGANISM: Artificial Sequence
<220> FEATURE:
<223> OTHER INFORMATION: unknown
<221> NAME/KEY: misc_feature
<222> LOCATION: (6)..(6)
<223> OTHER INFORMATION: Xaa is unknown
<221> NAME/KEY: misc_feature
<222> LOCATION: (7)..(7)
<223> OTHER INFORMATION: Xaa is unknown
<221> NAME/KEY: misc_feature
<222> LOCATION: (8)..(8)
<223> OTHER INFORMATION: Xaa is unknown
<221> NAME/KEY: misc_feature
<222> LOCATION: (15)..(15)
<223> OTHER INFORMATION: Xaa is unknown
<221> NAME/KEY: misc_feature
<222> LOCATION: (16)..(16)
<223> OTHER INFORMATION: Xaa is unknown
<221> NAME/KEY: misc_feature
<222> LOCATION: (23)..(23)
<223> OTHER INFORMATION: Xaa is unknown
<221> NAME/KEY: misc_feature
<222> LOCATION: (24)..(24)
<223> OTHER INFORMATION: Xaa is unknown
<221> NAME/KEY: misc_feature
<222> LOCATION: (25)..(25)
<223> OTHER INFORMATION: Xaa is unknown
<221> NAME/KEY: misc_feature
<222> LOCATION: (26)..(26)
<223> OTHER INFORMATION: Xaa is unknown
<221> NAME/KEY: misc_feature
<222> LOCATION: (27)..(27)
<223> OTHER INFORMATION: Xaa is unknown

<400> SEQUENCE: 6

Phe Ile Leu Val Trp Xaa Xaa Xaa Phe Ala Ile Leu Val Trp Xaa Xaa
1               5                   10                  15

Phe Ala Ile Leu Val Trp Xaa Xaa Xaa Xaa Xaa Phe Ile Leu Val Trp
            20                  25                  30

<210> SEQ ID NO 7
<211> LENGTH: 26
<212> TYPE: PRT
<213> ORGANISM: Artificial Sequence
<220> FEATURE:
<223> OTHER INFORMATION: unknown
<221> NAME/KEY: misc_feature
<222> LOCATION: (6)..(6)
<223> OTHER INFORMATION: Xaa is unknown
<221> NAME/KEY: misc_feature
<222> LOCATION: (7)..(7)
<223> OTHER INFORMATION: Xaa is unknown
<221> NAME/KEY: misc_feature
<222> LOCATION: (8)..(8)
<223> OTHER INFORMATION: Xaa is unknown
<221> NAME/KEY: misc_feature
<222> LOCATION: (9)..(9)
<223> OTHER INFORMATION: Xaa is unknown
<221> NAME/KEY: misc_feature
<222> LOCATION: (10)..(10)
<223> OTHER INFORMATION: Xaa is unknown
<221> NAME/KEY: misc_feature
```

```
<222> LOCATION: (17)..(17)
<223> OTHER INFORMATION: Xaa is unknown
<221> NAME/KEY: misc_feature
<222> LOCATION: (18)..(18)
<223> OTHER INFORMATION: Xaa is unknown
<221> NAME/KEY: misc_feature
<222> LOCATION: (19)..(19)
<223> OTHER INFORMATION: Xaa is unknown
<221> NAME/KEY: misc_feature
<222> LOCATION: (20)..(20)
<223> OTHER INFORMATION: Xaa is unknown
<221> NAME/KEY: misc_feature
<222> LOCATION: (21)..(21)
<223> OTHER INFORMATION: Xaa is unknown

<400> SEQUENCE: 7

Phe Ile Leu Val Trp Xaa Xaa Xaa Xaa Xaa Phe Ala Ile Leu Val Trp
1               5                   10                  15

Xaa Xaa Xaa Xaa Xaa Phe Ile Leu Val Trp
            20                  25

<210> SEQ ID NO 8
<211> LENGTH: 8
<212> TYPE: PRT
<213> ORGANISM: Artificial Sequence
<220> FEATURE:
<223> OTHER INFORMATION: unknown
<221> NAME/KEY: misc_feature
<222> LOCATION: (2)..(2)
<223> OTHER INFORMATION: Xaa is unknown
<221> NAME/KEY: misc_feature
<222> LOCATION: (4)..(4)
<223> OTHER INFORMATION: Xaa is unknown
<221> NAME/KEY: misc_feature
<222> LOCATION: (5)..(5)
<223> OTHER INFORMATION: Xaa is unknown
<221> NAME/KEY: misc_feature
<222> LOCATION: (7)..(7)
<223> OTHER INFORMATION: Xaa is unknown

<400> SEQUENCE: 8

Gly Xaa Gly Xaa Xaa Gly Xaa Lys
1               5

<210> SEQ ID NO 9
<211> LENGTH: 47
<212> TYPE: PRT
<213> ORGANISM: Mus musculus

<400> SEQUENCE: 9

Met Glu Pro Glu Cys Pro Arg Gly Leu Leu Pro Arg Pro Cys Arg Val
1               5                   10                  15

Leu Val Leu Leu Asn Pro Gln Gly Gly Lys Gly Lys Ala Leu Gln Leu
            20                  25                  30

Phe Gln Ser Arg Val Gln Pro Phe Leu Glu Glu Ala Glu Ile Thr
        35                  40                  45

<210> SEQ ID NO 10
<211> LENGTH: 52
<212> TYPE: PRT
<213> ORGANISM: Mus musculus

<400> SEQUENCE: 10

Ser Gly Asn Ala Leu Ala Ala Ser Val Asn His Tyr Ala Gly Tyr Glu
1               5                   10                  15

Gln Val Thr Asn Glu Asp Leu Leu Ile Asn Cys Thr Leu Leu Leu Cys
            20                  25                  30
```

-continued

Arg Arg Arg Leu Ser Pro Met Asn Leu Leu Ser Leu His Thr Ala Ser
            35                  40                  45

Gly Leu Arg Leu
        50

<210> SEQ ID NO 11
<211> LENGTH: 69
<212> TYPE: PRT
<213> ORGANISM: Mus musculus

<400> SEQUENCE: 11

Ala Tyr Leu Pro Val Gly Thr Val Ala Ser Lys Arg Pro Ala Ser Thr
1               5                   10                  15

Leu Val Gln Lys Gly Pro Val Asp Thr His Leu Val Leu Glu Glu Pro
            20                  25                  30

Val Pro Ser His Trp Thr Val Val Pro Glu Gln Asp Phe Val Leu Val
        35                  40                  45

Leu Val Leu His Thr His Leu Ser Ser Glu Leu Phe Ala Ala Pro
    50                  55                  60

Met Gly Arg Cys Glu
65

<210> SEQ ID NO 12
<211> LENGTH: 53
<212> TYPE: PRT
<213> ORGANISM: Mus musculus

<400> SEQUENCE: 12

Ala Gly Val Met His Leu Phe Tyr Val Arg Ala Gly Val Ser Arg Ala
1               5                   10                  15

Ala Leu Leu Arg Leu Phe Leu Ala Met Gln Lys Gly Lys His Met Glu
            20                  25                  30

Leu Asp Cys Pro Tyr Leu Val His Val Pro Val Val Ala Phe Arg Leu
        35                  40                  45

Glu Pro Arg Ser Gln
        50

<210> SEQ ID NO 13
<211> LENGTH: 63
<212> TYPE: PRT
<213> ORGANISM: Mus musculus

<400> SEQUENCE: 13

Phe Lys Leu Ile Leu Thr Glu Arg Lys Asn His Ala Arg Glu Leu Val
1               5                   10                  15

Cys Ala Glu Glu Leu Gly His Trp Asp Ala Leu Ala Val Met Ser Gly
            20                  25                  30

Asp Gly Leu Met His Glu Val Val Asn Gly Leu Met Glu Arg Pro Asp
        35                  40                  45

Trp Glu Thr Ala Ile Gln Lys Pro Leu Cys Ser Leu Pro Gly Gly
    50                  55                  60

<210> SEQ ID NO 14
<211> LENGTH: 47
<212> TYPE: PRT
<213> ORGANISM: Mus musculus

<400> SEQUENCE: 14

Tyr Ser Val Leu Ser Leu Ser Trp Gly Phe Val Ala Asp Val Asp Leu
1               5                   10                  15

Glu Ser Glu Lys Tyr Arg Arg Leu Gly Glu Ile Arg Phe Thr Val Gly
                20                  25                  30

Thr Phe Phe Arg Leu Ala Ser Leu Arg Ile Tyr Gln Gly Gln Leu
            35                  40                  45

<210> SEQ ID NO 15
<211> LENGTH: 46
<212> TYPE: PRT
<213> ORGANISM: Mus musculus

<400> SEQUENCE: 15

Thr His Leu Val Pro Leu Glu Pro Val Pro Ser His Trp Thr Val
1               5                   10                  15

Val Pro Glu Gln Asp Phe Val Leu Val Leu Val Leu His Thr His
                20                  25                  30

Leu Ser Ser Glu Leu Phe Ala Ala Pro Met Gly Arg Cys Glu
            35                  40                  45

<210> SEQ ID NO 16
<211> LENGTH: 49
<212> TYPE: PRT
<213> ORGANISM: Mus musculus

<400> SEQUENCE: 16

Arg Gly Val Phe Ser Val Asp Gly Glu Leu Met Val Cys Glu Ala Val
1               5                   10                  15

Gln Gly Gln Val His Pro Asn Tyr Leu Trp Met Val Cys Gly Ser Arg
                20                  25                  30

Asp Ala Pro Ser Gly Arg Asp Ser Arg Arg Gly Pro Pro Pro Glu Glu
            35                  40                  45

Pro

<210> SEQ ID NO 17
<211> LENGTH: 54
<212> TYPE: PRT
<213> ORGANISM: Mus musculus

<400> SEQUENCE: 17

Met Trp Trp Cys Cys Val Leu Phe Val Val Glu Cys Pro Arg Gly Leu
1               5                   10                  15

Leu Pro Arg Pro Cys Arg Val Leu Val Leu Leu Asn Pro Gln Gly Gly
                20                  25                  30

Lys Gly Lys Ala Leu Gln Leu Phe Gln Ser Arg Val Gln Pro Phe Leu
            35                  40                  45

Glu Glu Ala Glu Ile Thr
    50

<210> SEQ ID NO 18
<211> LENGTH: 52
<212> TYPE: PRT
<213> ORGANISM: Mus musculus

<400> SEQUENCE: 18

Ser Gly Asn Ala Leu Ala Ala Ser Val Asn His Tyr Ala Gly Tyr Glu
1               5                   10                  15

Gln Val Thr Asn Glu Asp Leu Leu Ile Asn Cys Thr Leu Leu Leu Cys
                20                  25                  30

Arg Arg Arg Leu Ser Pro Met Asn Leu Leu Ser Leu His Thr Ala Ser
            35                  40                  45

Gly Leu Arg Leu
    50

<210> SEQ ID NO 19
<211> LENGTH: 24
<212> TYPE: PRT
<213> ORGANISM: Mus musculus

<400> SEQUENCE: 19

Ala Tyr Leu Pro Val Gly Thr Val Ala Ser Lys Arg Pro Ala Ser Thr
1               5                   10                  15

Leu Val Gln Lys Gly Pro Val Asp
            20

<210> SEQ ID NO 20
<211> LENGTH: 53
<212> TYPE: PRT
<213> ORGANISM: Mus musculus

<400> SEQUENCE: 20

Ala Gly Val Met His Leu Phe Tyr Val Arg Ala Gly Val Ser Arg Ala
1               5                   10                  15

Ala Leu Leu Arg Leu Phe Leu Ala Met Gln Lys Gly Lys His Met Glu
            20                  25                  30

Leu Asp Cys Pro Tyr Leu Val His Val Pro Val Val Ala Phe Arg Leu
        35                  40                  45

Glu Pro Arg Ser Gln
    50

<210> SEQ ID NO 21
<211> LENGTH: 63
<212> TYPE: PRT
<213> ORGANISM: Mus musculus

<400> SEQUENCE: 21

Phe Lys Leu Ile Leu Thr Glu Arg Lys Asn His Ala Arg Glu Leu Val
1               5                   10                  15

Cys Ala Glu Glu Leu Gly His Trp Asp Ala Leu Ala Val Met Ser Gly
            20                  25                  30

Asp Gly Leu Met His Glu Val Val Asn Gly Leu Met Glu Arg Pro Asp
        35                  40                  45

Trp Glu Thr Ala Ile Gln Lys Pro Leu Cys Ser Leu Pro Gly Gly
    50                  55                  60

<210> SEQ ID NO 22
<211> LENGTH: 47
<212> TYPE: PRT
<213> ORGANISM: Mus musculus

<400> SEQUENCE: 22

Tyr Ser Val Leu Ser Leu Ser Trp Gly Phe Val Ala Asp Val Asp Leu
1               5                   10                  15

Glu Ser Glu Lys Tyr Arg Arg Leu Gly Glu Ile Arg Phe Thr Val Gly
            20                  25                  30

Thr Phe Phe Arg Leu Ala Ser Leu Arg Ile Tyr Gln Gly Gln Leu
        35                  40                  45

<210> SEQ ID NO 23
<211> LENGTH: 46
<212> TYPE: PRT

<213> ORGANISM: Mus musculus

<400> SEQUENCE: 23

Thr His Leu Val Pro Leu Glu Glu Pro Val Pro Ser His Trp Thr Val
1               5                   10                  15

Val Pro Glu Gln Asp Phe Val Leu Val Leu Val Leu Leu His Thr His
            20                  25                  30

Leu Ser Ser Glu Leu Phe Ala Ala Pro Met Gly Arg Cys Glu
        35                  40                  45

<210> SEQ ID NO 24
<211> LENGTH: 49
<212> TYPE: PRT
<213> ORGANISM: Mus musculus

<400> SEQUENCE: 24

Arg Gly Val Phe Ser Val Asp Gly Glu Leu Met Val Cys Glu Ala Val
1               5                   10                  15

Gln Gly Gln Val His Pro Asn Tyr Leu Trp Met Val Cys Gly Ser Arg
            20                  25                  30

Asp Ala Pro Ser Gly Arg Asp Ser Arg Arg Gly Pro Pro Glu Glu
        35                  40                  45

Pro

<210> SEQ ID NO 25
<211> LENGTH: 55
<212> TYPE: PRT
<213> ORGANISM: Saccharomyces cerevisiae

<400> SEQUENCE: 25

Asn Ile Ser Ser Gly Thr Val Glu Glu Ile Leu Glu Lys Ser Tyr Glu
1               5                   10                  15

Asn Ser Lys Arg Asn Arg Ser Ile Leu Val Ile Ile Asn Pro His Gly
            20                  25                  30

Gly Lys Gly Thr Ala Lys Asn Leu Phe Leu Thr Lys Ala Arg Pro Ile
        35                  40                  45

Leu Val Glu Ser Gly Cys Lys
    50                  55

<210> SEQ ID NO 26
<211> LENGTH: 46
<212> TYPE: PRT
<213> ORGANISM: Saccharomyces cerevisiae

<400> SEQUENCE: 26

Ser Gly Asn Ala Met Ser Ile Ser Cys His Trp Thr Asn Asn Pro Ser
1               5                   10                  15

Tyr Ala Ala Leu Cys Leu Val Lys Ser Ile Glu Thr Arg Ile Asp Leu
            20                  25                  30

Met Cys Cys Ser Gln Pro Ser Tyr Met Asn Glu Trp Pro Arg
        35                  40                  45

SEQ ID NO 27
LENGTH: 37
<212> TYPE: PRT
<213> ORGANISM: Saccharomyces cerevisiae

<400> SEQUENCE: 27

```
Glu Asn Lys Asp Lys Asn Lys Gly Cys Leu Thr Phe Glu Pro Asn Pro
1               5                   10                  15

Ser Pro Asn Ser Ser Pro Asp Leu Leu Ser Lys Asn Asn Ile Asn Asn
            20                  25                  30

Ser Thr Lys Asp Glu
            35
```

SEQ ID NO 28
LENGTH: 51
<212> TYPE: PRT
<213> ORGANISM: Saccharomyces cerevisiae

<400> SEQUENCE: 28

```
Asp Gly Thr Ile Asp Leu Val Ile Thr Asp Ala Arg Ile Pro Val Thr
1               5                   10                  15

Arg Met Thr Pro Ile Leu Leu Ser Leu Asp Lys Gly Ser His Val Leu
            20                  25                  30

Glu Pro Glu Val Ile His Ser Lys Ile Leu Ala Tyr Lys Ile Ile Pro
            35                  40                  45

Lys Val Glu
        50
```

<210> SEQ ID NO 29
<211> LENGTH: 64
<212> TYPE: PRT
<213> ORGANISM: Saccharomyces cerevisiae

<400> SEQUENCE: 29

```
Ile Glu Ile Ala Tyr Thr Lys Tyr Ala Arg His Ala Ile Asp Ile Ala
1               5                   10                  15

Lys Asp Leu Asp Ile Ser Lys Tyr Asp Thr Ile Ala Cys Ala Ser Gly
            20                  25                  30

Asp Gly Ile Pro Tyr Glu Val Ile Asn Gly Leu Tyr Arg Arg Pro Asp
            35                  40                  45

Arg Val Asp Ala Phe Asn Lys Leu Ala Val Thr Gln Leu Pro Cys Gly
        50                  55                  60
```

<210> SEQ ID NO 30
<211> LENGTH: 64
<212> TYPE: PRT
<213> ORGANISM: Saccharomyces cerevisiae

<400> SEQUENCE: 30

```
Leu Ser Phe Leu Ser Gln Thr Tyr Gly Val Ile Ala Glu Ser Asp Ile
1               5                   10                  15

Asn Thr Glu Phe Ile Arg Trp Met Gly Pro Val Arg Phe Asn Leu Gly
            20                  25                  30

Val Ala Phe Asn Ile Ile Gln Gly Lys Lys Tyr Pro Cys Glu Val Phe
            35                  40                  45

Val Lys Tyr Ala Ala Lys Ser Lys Lys Glu Leu Lys Val His Phe Leu
        50                  55                  60
```

<210> SEQ ID NO 31
<211> LENGTH: 60
<212> TYPE: PRT
<213> ORGANISM: Saccharomyces cerevisiae

<400> SEQUENCE: 31

-continued

```
Leu Ser Pro Asn Phe Leu Asn Glu Asp Asn Phe Lys Leu Lys Tyr Pro
1               5                   10                  15

Met Thr Glu Pro Val Pro Arg Asp Trp Glu Lys Met Asp Ser Glu Leu
                20                  25                  30

Thr Asp Asn Leu Thr Ile Phe Tyr Thr Gly Lys Met Pro Tyr Ile Ala
            35                  40                  45

Lys Asp Thr Lys Phe Phe Pro Ala Ala Leu Pro Ala
        50                  55                  60
```

<210> SEQ ID NO 32
<211> LENGTH: 42
<212> TYPE: PRT
<213> ORGANISM: Saccharomyces cerevisiae

<400> SEQUENCE: 32

```
Ser Gly Leu Phe Ser Val Asp Gly Glu Lys Phe Pro Leu Glu Pro Leu
1               5                   10                  15

Gln Val Glu Ile Met Pro Met Leu Cys Lys Thr Leu Leu Arg Asn Gly
                20                  25                  30

Arg Tyr Ile Asp Thr Glu Phe Glu Ser Met
            35                  40
```

<210> SEQ ID NO 33
<211> LENGTH: 51
<212> TYPE: PRT
<213> ORGANISM: Saccharomyces cerevisiae

<400> SEQUENCE: 33

```
Asp Leu Val Glu Glu Ile Leu Lys Arg Ser Tyr Lys Asn Thr Arg Arg
1               5                   10                  15

Asn Lys Ser Ile Phe Val Ile Asn Pro Phe Gly Gly Lys Gly Lys
                20                  25                  30

Ala Lys Lys Leu Phe Met Thr Lys Ala Lys Pro Leu Leu Leu Ala Ser
            35                  40                  45

Arg Cys Ser
    50
```

<210> SEQ ID NO 34
<211> LENGTH: 46
<212> TYPE: PRT
<213> ORGANISM: Saccharomyces cerevisiae

<400> SEQUENCE: 34

```
Ser Gly Asn Ala Met Ser Val Ser Cys His Trp Thr Asn Asn Pro Ser
1               5                   10                  15

Tyr Ser Thr Leu Cys Leu Ile Lys Ser Ile Glu Thr Arg Ile Asp Leu
                20                  25                  30

Met Cys Cys Ser Gln Pro Ser Tyr Ala Arg Glu His Pro Lys
            35                  40                  45
```

<210> SEQ ID NO 35
<211> LENGTH: 53
<212> TYPE: PRT
<213> ORGANISM: Saccharomyces cerevisiae

<400> SEQUENCE: 35

```
Glu His Lys Asn Lys Gly Ser Leu Glu Phe Gln His Ile Thr Met Asn
1               5                   10                  15

Lys Asp Asn Glu Asp Cys Asp Asn Tyr Asn Tyr Glu Asn Glu Tyr Glu
                20                  25                  30
```

```
Thr Glu Asn Glu Asp Glu Asp Ala Asp Ala Asp Glu Asp
        35                  40                  45

Ser His Leu Ile Ser
    50
```

<210> SEQ ID NO 36
<211> LENGTH: 51
<212> TYPE: PRT
<213> ORGANISM: Saccharomyces cerevisiae

<400> SEQUENCE: 36

```
Asp Gly Thr Met Asp Met Val Ile Thr Asp Ala Arg Thr Ser Leu Thr
1               5                   10                  15

Arg Met Ala Pro Ile Leu Leu Gly Leu Asp Lys Gly Ser His Val Leu
            20                  25                  30

Gln Pro Glu Val Leu His Ser Lys Ile Leu Ala Tyr Lys Ile Ile Pro
        35                  40                  45

Lys Leu Gly
    50
```

<210> SEQ ID NO 37
<211> LENGTH: 64
<212> TYPE: PRT
<213> ORGANISM: Saccharomyces cerevisiae

<400> SEQUENCE: 37

```
Ile Glu Val Val Tyr Thr Lys Tyr Pro Gly His Ala Ile Glu Ile Ala
1               5                   10                  15

Arg Glu Met Asp Ile Asp Lys Tyr Asp Thr Ile Ala Cys Ala Ser Gly
            20                  25                  30

Asp Gly Ile Pro His Glu Val Ile Asn Gly Leu Tyr Gln Arg Pro Asp
        35                  40                  45

His Val Lys Ala Phe Asn Asn Ile Ala Ile Thr Glu Ile Pro Cys Gly
    50                  55                  60
```

<210> SEQ ID NO 38
<211> LENGTH: 64
<212> TYPE: PRT
<213> ORGANISM: Saccharomyces cerevisiae

<400> SEQUENCE: 38

```
Leu Ser Phe Leu Ser Gln Thr Tyr Gly Leu Ile Ala Glu Thr Asp Ile
1               5                   10                  15

Asn Thr Glu Phe Ile Arg Trp Met Gly Pro Ala Arg Phe Glu Leu Gly
            20                  25                  30

Val Ala Phe Asn Ile Ile Gln Lys Lys Lys Tyr Pro Cys Glu Ile Tyr
        35                  40                  45

Val Lys Tyr Ala Ala Lys Ser Lys Asn Glu Leu Lys Asn His Tyr Leu
    50                  55                  60
```

<210> SEQ ID NO 39
<211> LENGTH: 65
<212> TYPE: PRT
<213> ORGANISM: Saccharomyces cerevisiae

<400> SEQUENCE: 39

```
Arg Asp Leu Ala Asp Ser Ser Ala Asp Gln Ile Lys Glu Glu Asp Phe
1               5                   10                  15

Lys Ile Lys Tyr Pro Leu Asp Glu Gly Ile Pro Ser Asp Trp Glu Arg
```

```
            20                  25                  30
Leu Asp Pro Asn Ile Ser Asn Asn Leu Gly Ile Phe Tyr Thr Gly Lys
        35                  40                  45
Met Pro Tyr Val Ala Ala Asp Thr Lys Phe Phe Pro Ala Ala Leu Pro
    50                  55                  60
Ser
65

<210> SEQ ID NO 40
<211> LENGTH: 42
<212> TYPE: PRT
<213> ORGANISM: Saccharomyces cerevisiae

<400> SEQUENCE: 40

Asn Gly Leu Phe Ser Val Asp Gly Glu Lys Phe Pro Leu Glu Pro Leu
1               5                   10                  15
Gln Val Glu Ile Met Pro Arg Leu Cys Lys Thr Leu Leu Arg Asn Gly
            20                  25                  30
Arg Tyr Val Asp Thr Asp Phe Asp Ser Met
        35                  40

<210> SEQ ID NO 41
<211> LENGTH: 50
<212> TYPE: PRT
<213> ORGANISM: Schizosaccharomyces pombe

<400> SEQUENCE: 41

Phe Cys Glu Tyr Leu Leu Asp Val Ala Tyr Lys Gly Ile Lys Arg Ser
1               5                   10                  15
Arg Arg Phe Ile Val Phe Ile Asn Pro His Gly Gly Lys Gly Lys Ala
            20                  25                  30
Lys His Ile Trp Glu Ser Glu Ala Glu Pro Val Phe Ser Ser Ala His
        35                  40                  45
Ser Ile
    50

<210> SEQ ID NO 42
<211> LENGTH: 42
<212> TYPE: PRT
<213> ORGANISM: Schizosaccharomyces pombe

<400> SEQUENCE: 42

Ser Gly Asn Ala Phe Ser Tyr Asn Ala Thr Gly Gln Leu Lys Pro Ala
1               5                   10                  15
Leu Thr Ala Leu Glu Ile Leu Lys Gly Arg Pro Thr Ser Phe Asp Leu
            20                  25                  30
Met Thr Phe Glu Gln Lys Gly Lys Ala
        35                  40

<210> SEQ ID NO 43
<211> LENGTH: 17
<212> TYPE: PRT
<213> ORGANISM: Schizosaccharomyces pombe

<400> SEQUENCE: 43

Glu Lys Ser Lys Asn Leu Ala Pro Met Ser Glu Ser Ser Asp Ser Asp
1               5                   10                  15
Lys
```

-continued

<210> SEQ ID NO 44
<211> LENGTH: 51
<212> TYPE: PRT
<213> ORGANISM: Schizosaccharomyces pombe

<400> SEQUENCE: 44

Asp Gly Leu Ile Asp Val Val Ile Val Tyr Ser Lys Gln Phe Arg Lys
1               5                   10                  15

Ser Leu Leu Ser Met Phe Thr Gln Leu Asp Asn Gly Gly Phe Tyr Tyr
            20                  25                  30

Ser Lys His Leu Asn Tyr Tyr Lys Val Arg Ser Phe Arg Phe Thr Pro
        35                  40                  45

Val Asn Thr
    50

<210> SEQ ID NO 45
<211> LENGTH: 63
<212> TYPE: PRT
<213> ORGANISM: Schizosaccharomyces pombe

<400> SEQUENCE: 45

Cys Glu Val Val Leu Thr Arg Arg Lys Asp His Ala Lys Ser Ile Ala
1               5                   10                  15

Lys Asn Leu Asp Val Gly Ser Tyr Asp Gly Ile Leu Ser Val Gly Gly
            20                  25                  30

Asp Gly Leu Phe His Glu Val Ile Asn Gly Leu Gly Glu Arg Asp Asp
        35                  40                  45

Tyr Leu Glu Ala Phe Lys Leu Pro Val Cys Met Ile Pro Gly Gly
    50                  55                  60

<210> SEQ ID NO 46
<211> LENGTH: 63
<212> TYPE: PRT
<213> ORGANISM: Schizosaccharomyces pombe

<400> SEQUENCE: 46

Tyr Ser Phe Leu Thr Ala Asn Tyr Gly Ile Ile Ala Asp Cys Asp Ile
1               5                   10                  15

Gly Thr Glu Asn Trp Arg Phe Met Gly Glu Asn Arg Ala Tyr Leu Gly
            20                  25                  30

Phe Phe Leu Arg Leu Phe Gln Lys Pro Asp Trp Lys Cys Ser Ile Glu
        35                  40                  45

Met Asp Val Val Ser Ser Asp Arg Thr Glu Ile Lys His Met Tyr
    50                  55                  60

<210> SEQ ID NO 47
<211> LENGTH: 42
<212> TYPE: PRT
<213> ORGANISM: Schizosaccharomyces pombe

<400> SEQUENCE: 47

Thr Val Ser Thr Ser Pro Glu Ser His Leu Leu Thr Phe Glu Ile Asn
1               5                   10                  15

Asp Leu Ser Ile Phe Cys Ala Gly Leu Leu Pro Tyr Ile Ala Pro Asp
            20                  25                  30

Ala Lys Met Phe Pro Ala Ala Ser Asn Asp
        35                  40

<210> SEQ ID NO 48
<211> LENGTH: 41

```
<212> TYPE: PRT
<213> ORGANISM: Schizosaccharomyces pombe

<400> SEQUENCE: 48

Gly Lys Arg His Tyr Phe Ala Leu Asp Gly Glu Ser Tyr Pro Leu Glu
1               5                   10                  15

Pro Phe Glu Cys Arg Val Ala Pro Lys Leu Gly Thr Thr Leu Ser Pro
            20                  25                  30

Val Ala Gly Phe Gln Leu Leu Asp Ile
        35                  40

<210> SEQ ID NO 49
<211> LENGTH: 55
<212> TYPE: PRT
<213> ORGANISM: Caenorhabditis elegans

<400> SEQUENCE: 49

Glu Asn Glu Gln Leu Thr Ser Val Ile Leu Ser Arg Lys Pro Pro Pro
1               5                   10                  15

Gln Glu Gln Cys Arg Gly Asn Leu Leu Val Phe Ile Asn Pro Asn Ser
            20                  25                  30

Gly Thr Gly Lys Ser Leu Glu Thr Phe Ala Asn Thr Val Gly Pro Lys
        35                  40                  45

Leu Asp Lys Ser Leu Ile Arg
    50                  55

<210> SEQ ID NO 50
<211> LENGTH: 52
<212> TYPE: PRT
<213> ORGANISM: Caenorhabditis elegans

<400> SEQUENCE: 50

Ser Gly Asn Gly Leu Leu Cys Ser Val Leu Ser Lys Tyr Gly Thr Lys
1               5                   10                  15

Met Asn Glu Lys Ser Val Met Glu Arg Ala Leu Glu Ile Ala Thr Ser
            20                  25                  30

Pro Thr Ala Lys Ala Glu Ser Val Ala Leu Tyr Ser Val Lys Thr Asp
        35                  40                  45

Asn Gln Ser Tyr
    50

<210> SEQ ID NO 51
<211> LENGTH: 48
<212> TYPE: PRT
<213> ORGANISM: Caenorhabditis elegans

<400> SEQUENCE: 51

Thr Tyr Arg Pro Tyr Lys Pro Lys Gly Phe His Pro Ser Ser Asn Val
1               5                   10                  15

Phe Ser Val Tyr Glu Lys Thr Thr Gln Gln Arg Ile Asp Asp Ser Lys
            20                  25                  30

Val Lys Thr Asn Gly Ser Val Ser Asp Ser Glu Glu Thr Met Glu
        35                  40                  45

<210> SEQ ID NO 52
<211> LENGTH: 53
<212> TYPE: PRT
<213> ORGANISM: Caenorhabditis elegans

<400> SEQUENCE: 52
```

```
Asp Asn Arg Ile His Leu Ser Tyr Ile Leu Trp Lys Asp Ile Gly Thr
1               5                   10                  15

Arg Val Asn Ile Ala Lys Tyr Leu Leu Ala Ile Glu His Glu Thr His
            20                  25                  30

Leu Asp Leu Pro Phe Val Lys His Val Glu Val Ser Ser Met Lys Leu
        35                  40                  45

Glu Val Ile Ser Glu
    50
```

<210> SEQ ID NO 53
<211> LENGTH: 65
<212> TYPE: PRT
<213> ORGANISM: Caenorhabditis elegans

<400> SEQUENCE: 53

```
Tyr Glu Val Val Val Thr Thr Gly Pro Asn His Ala Arg Asn Val Leu
1               5                   10                  15

Met Thr Lys Ala Asp Leu Gly Lys Phe Asn Gly Val Leu Ile Leu Ser
            20                  25                  30

Gly Asp Gly Leu Val Phe Glu Ala Leu Asn Gly Ile Leu Cys Arg Glu
        35                  40                  45

Asp Ala Phe Arg Ile Phe Pro Thr Leu Pro Ile Gly Ile Val Pro Ser
    50                  55                  60

Gly
65
```

<210> SEQ ID NO 54
<211> LENGTH: 48
<212> TYPE: PRT
<213> ORGANISM: Caenorhabditis elegans

<400> SEQUENCE: 54

```
Ala Ser Phe Leu Ser Ile Gly Trp Gly Leu Met Ala Asp Ile Asp Ile
1               5                   10                  15

Asp Ser Glu Lys Trp Arg Lys Ser Leu Gly His His Arg Phe Thr Val
            20                  25                  30

Met Gly Phe Ile Arg Ser Cys Asn Leu Arg Ser Tyr Lys Gly Arg Leu
        35                  40                  45
```

<210> SEQ ID NO 55
<211> LENGTH: 56
<212> TYPE: PRT
<213> ORGANISM: Caenorhabditis elegans

<400> SEQUENCE: 55

```
Thr Lys Phe Gln Asn Trp Thr Leu Pro Asp Ser Asp Glu Thr Leu Ala
1               5                   10                  15

Val Gly Ser Ser Asp Leu Glu Glu Thr Val Val Ile Glu Asp Asn Phe
            20                  25                  30

Val Asn Ile Tyr Ala Val Thr Leu Ser His Ile Ala Ala Asp Gly Pro
        35                  40                  45

Phe Ala Pro Ser Ala Lys Leu Glu
    50                  55
```

<210> SEQ ID NO 56
<211> LENGTH: 32
<212> TYPE: PRT
<213> ORGANISM: Caenorhabditis elegans

<400> SEQUENCE: 56

-continued

```
Gly Ser His Val Val Leu Asp Gly Glu Val Val Asp Thr Lys Thr Ile
1               5                   10                  15

Glu Val Ala Ser Thr Lys Asn His Ile Ser Val Phe Ser Ser Thr Ala
            20                  25                  30
```